(12) United States Patent
Hirono et al.

(10) Patent No.: US 9,013,569 B2
(45) Date of Patent: Apr. 21, 2015

(54) CONVEYING DEVICE, CONVEYING METHOD AND MICROSCOPE SYSTEM

(75) Inventors: Yu Hirono, Tokyo (JP); Fumiyasu Suzuki, Saitama (JP); Yuichi Machida, Kanagawa (JP)

(73) Assignee: Sony Corporation, Tokyo (JP)

( * ) Notice: Subject to any disclaimer, the term of this patent is extended or adjusted under 35 U.S.C. 154(b) by 950 days.

(21) Appl. No.: 13/167,990

(22) Filed: Jun. 24, 2011

(65) Prior Publication Data
US 2012/0003065 A1   Jan. 5, 2012

(30) Foreign Application Priority Data

Jun. 30, 2010 (JP) ................ P2010-150528

(51) Int. Cl.
*H04N 9/47* (2006.01)
*H04N 7/18* (2006.01)
*G02B 21/34* (2006.01)
*G02B 21/26* (2006.01)

(52) U.S. Cl.
CPC .............. *G02B 21/34* (2013.01); *G02B 21/26* (2013.01)

(58) Field of Classification Search
CPC ....... G02B 21/24; G02B 21/26; G02B 21/364
USPC ....................... 348/79; 414/222.02
See application file for complete search history.

(56) References Cited

U.S. PATENT DOCUMENTS 6,847,481 B1 *   1/2005   Ludl et al. .................. 359/391
6,951,663 B1 * 10/2005   Edwards ..................... 427/2.11

FOREIGN PATENT DOCUMENTS

CN       1336266        2/2002
WO    2006-098442       3/2006

OTHER PUBLICATIONS

State Intellectual Property Office of the People's Republic of China, Notification of the First Office Action issued in connection with Chinese Patent Application No. 201110171703.7, dated Oct. 31, 2013. (21 pages).

* cited by examiner

*Primary Examiner* — Thai Tran
*Assistant Examiner* — Girumsew Wendmagegn
(74) *Attorney, Agent, or Firm* — K&L Gates LLP

(57) ABSTRACT

A conveying device including: a storage unit storing two or more sheets of slide glasses to be subjected to a predetermined treatment; a stage holding only one sheet of slide glass to be subjected to the treatment; a supply arm by which one sheet of slide glass to be subjected to the treatment is picked up from the storage unit and supplied onto the stage; a discharge arm by which the slide glass mounted on the stage is picked up and discharged in the storage unit; a moving unit operable to move the supply arm and the discharge arm in an integral manner so as to bring the supply arm or the discharge arm into proximity to each of the storage unit and the stage; and a control unit operable to control the supply arm, the discharge arm and the moving unit.

12 Claims, 44 Drawing Sheets

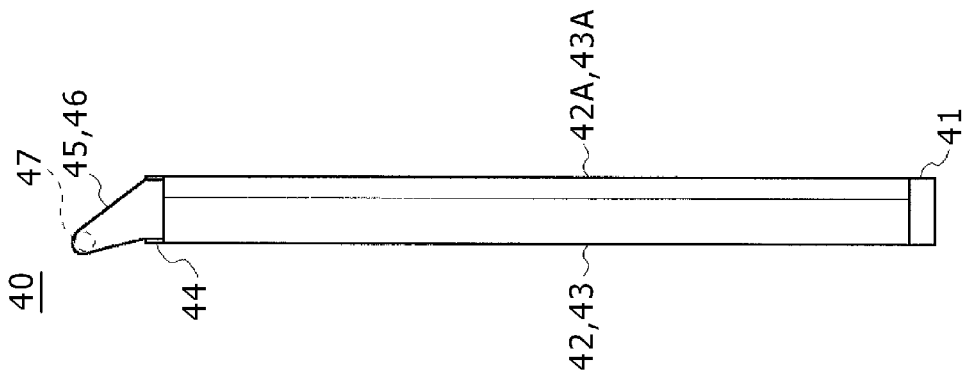
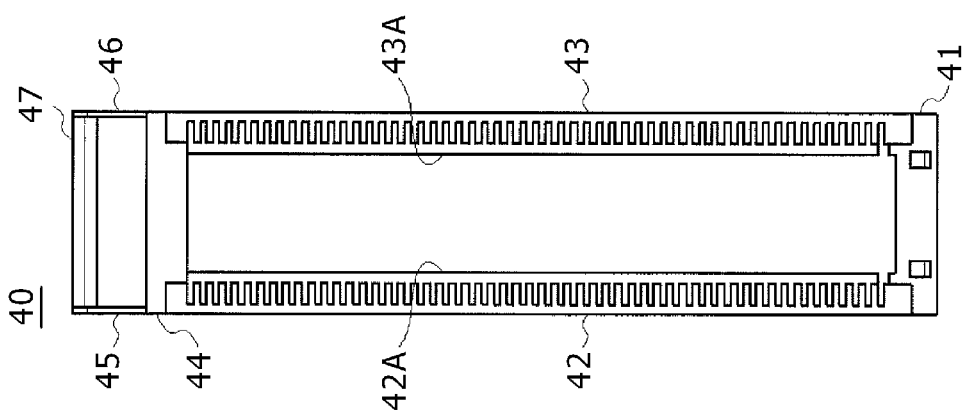
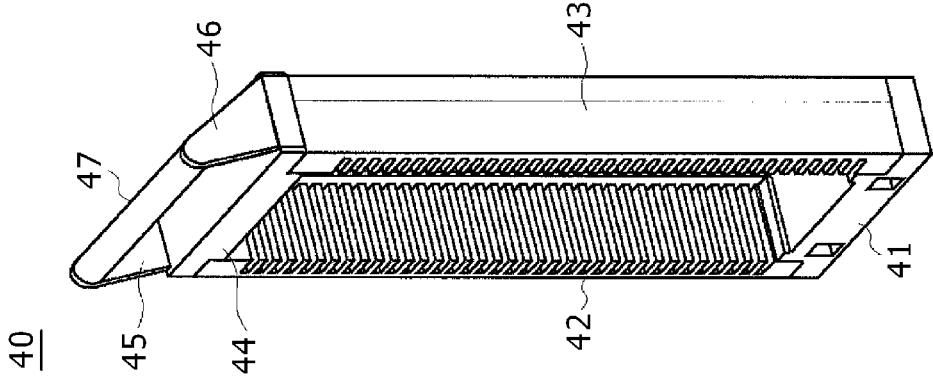

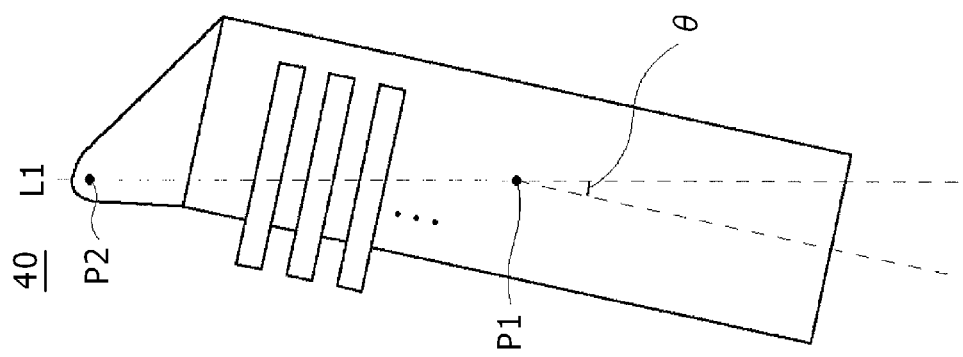
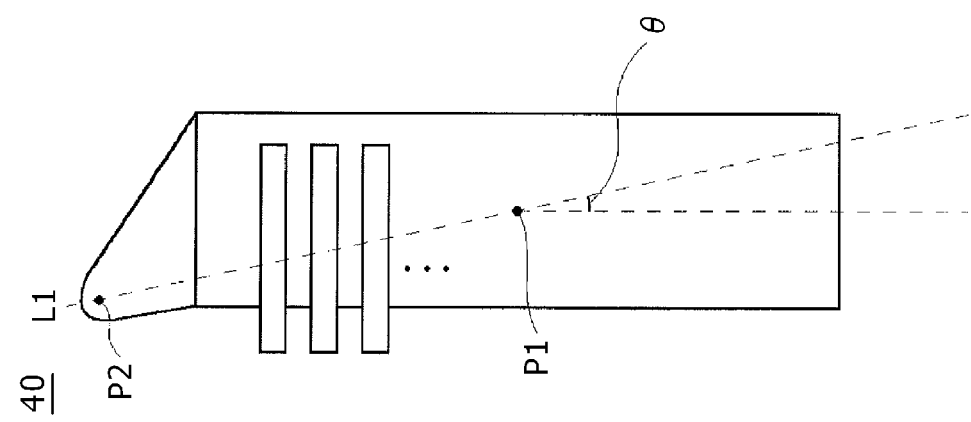

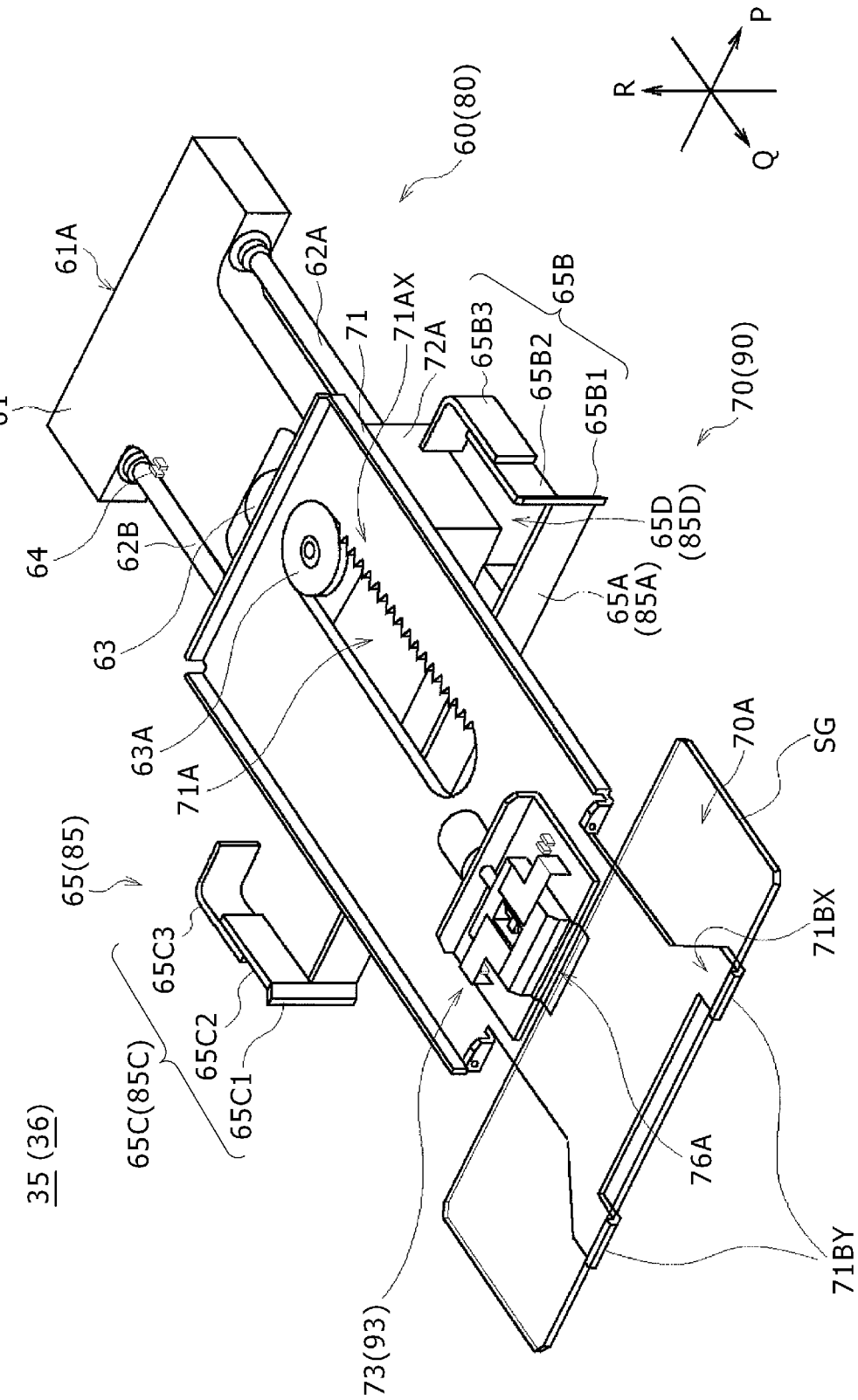

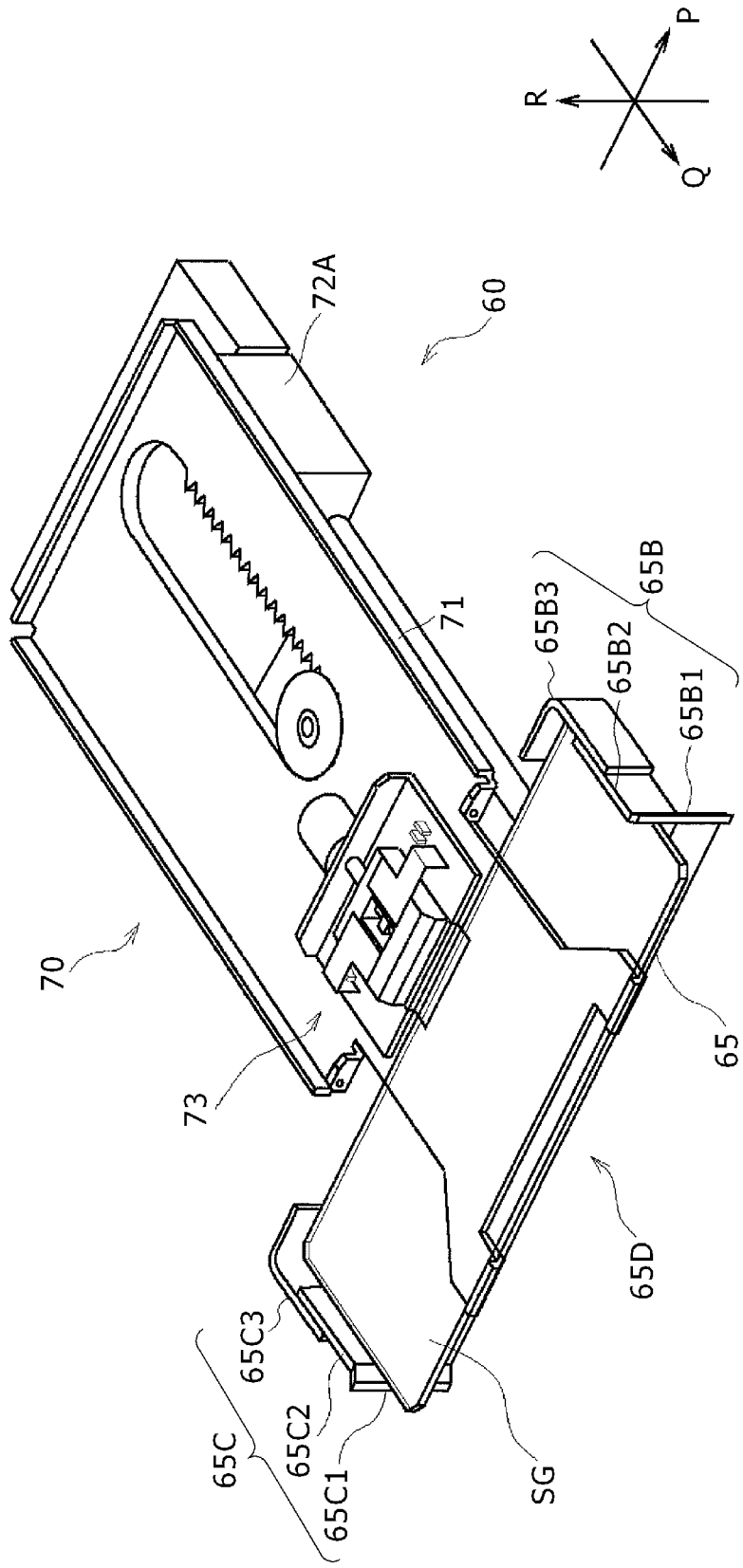

CONVEYING DEVICE, CONVEYING METHOD AND MICROSCOPE SYSTEM

CROSS REFERENCES TO RELATED APPLICATIONS

The present application contains subject matter related to that disclosed in Japanese Priority Patent Application JP 2010-150528 filed in the Japan Patent Office on Jun. 30, 2010, the entire content of which is hereby incorporated by reference.

BACKGROUND

The present application relates to a conveying device, a conveying method and a microscope system, and is suitable for application, for example, to the field of observing a biological sample (living body sample) through magnification.

Heretofore, as a technique of observing a biological sample, there has been widely used a technique in which the biological sample is placed on a stage of a microscope and is observed by the observer's naked eye.

On the other hand, in recent years, there has been proposed a microscope system corresponding to the so-called virtual slide system in which an image sensing element is disposed at the focal position of an ocular of a microscope, namely, at a location corresponding to the observer's eye, and image data representing a biological sample in a magnified form is formed.

The thus formed image data has various advantages in that the image data can be presented to the observer in the state of being displayed on a display unit of a computer system or the like, the image data is excellent in storage properties and reproducibility, the image data can be easily transmitted to a remote place, and so on.

Particularly, in the case where it is desired to form multiple pieces of image data of biological samples, it may be necessary in the microscope system to repeat a replacing treatment of preliminarily preparing a multiplicity of slide glasses, supplying one sheet of the slide glass onto a stage, performing a photographing treatment (image pick-up treatment) and then replacing the slide glass.

In view of this, examples of the microscope systems which have been proposed include one in which, in order to automate the replacing treatment, one sheet of slide glass at a time is taken out from a cassette in which a plurality of rows of stacks each having slide glasses stacked at a predetermined interval are contained, and the thus taken-out slide glass is conveyed along a rectilinear direction, to be sequentially set onto a stage one by one (see, for example, PCT Patent Publication No. WO2006/098442 (FIGS. 1 and 3), hereinafter referred to as Patent Document 1).

SUMMARY

In such a microscope system as above-mentioned, however, there has been the problem that the time required for replacement of the slide glass is prolonged as the distance between the containing site for the slide glass in the cassette and the stage increases.

Thus, there is a need for a proposal of a conveying device, a conveying method and a microscope system such that replacement of a slide glass can be carried out in a short time.

According to one embodiment, there is provided a conveying device including: a storage unit storing two or more sheets of slide glasses to be subjected to a predetermined treatment; a stage holding only one sheet of slide glass to be subjected to the treatment; a supply arm by which one sheet of slide glass to be subjected to the treatment is picked up from the storage unit and supplied onto the stage; a discharge arm by which the slide glass mounted on the stage is picked up and discharged in the storage unit; a moving unit operable to move the supply arm and the discharge arm in an integral manner so as to bring the supply arm or the discharge arm into proximity to the storage unit or the stage; and a control unit operable to control the supply arm, the discharge arm and the moving unit. In the conveying device, the control unit performs such a control that a second one of the slide glasses to be subjected to the treatment subsequently to a first one of the slide glasses mounted on the stage is picked up by the supply arm, thereafter the first slide glass is picked up from the stage by the discharge arm brought into proximity to the stage by the moving unit, and then the second slide glass is mounted onto the stage by the supply arm.

The conveying device ensures that when the treatment of the first slide glass is finished, the first slide glass can be discharged by the discharge arm having been in a stand-by state in the vicinity of the stage, and, subsequently, the second slide glass can be supplied by the supply arm. Thus, the conveying device ensures that the treatment of the second slide glass can immediately be started, while only requiring a little replacing time, after the treatment of the first slide glass is finished.

According to another embodiment, there is provided a conveying method including: a first step in which a supply arm operable to pick up one sheet of slide glass from a storage unit storing two or more sheets of slide glasses to be subjected to a predetermined treatment and operable to supply the one sheet of slide glass onto a stage for holding only one sheet of slide glass thereon and a discharge arm operable to pick up the slide glass mounted on the stage and discharge the slide glass into the storage unit are brought into proximity to the storage unit by a rotating section operable to rotate the supply arm and the discharge arm as one body about a predetermined rotation axis so as to bring the supply arm and the discharge arm into proximity to the storage unit or the stage; a second step of picking up a second slide glass from the storage unit by the supply arm; a third step of bringing the supply arm and the discharge arm into proximity to the stage by the rotating section; a fourth step of picking up a first slide glass from the stage by the discharge arm; a fifth step of mounting the second slide glass onto the stage by the supply arm; a sixth step of bringing the supply arm and the discharge arm into proximity to the storage unit by the rotating section; and a seventh step of mounting the second slide glass onto the storage unit by the discharge arm.

The conveying method ensures that when the treatment of the first slide glass is finished, the first slide glass can be discharged by the discharge arm having been in a stand-by state in the vicinity of the stage, and, subsequently, the second slide glass can be supplied by the supply arm. Thus, the conveying method ensures that the treatment of the second slide glass can immediately be started, while requiring only a little replacing time, after the treatment of the first slide glass is finished.

According to a further embodiment, there is provided a microscope system including: a storage unit operable to store two or more sheets of slide glasses each having fixed thereon an object of which a magnified image is to be formed; a stage operable to hold thereon only one of the sheets of slide glasses; a supply arm by which the one of the sheets of slide glasses is picked up from the storage unit and supplied onto the stage; a discharge arm by which the slide glass mounted on the stage is picked up and discharged into the storage unit;

a moving section operable to move the supply arm and the discharge arm as one body so as to bring the supply arm or the discharge arm into proximity to the storage unit or the stage; and a control unit operable to control the supply arm, the discharge arm and the moving section. In the microscope system, the control unit performs such a control that a second one of the slide glasses to be subjected to formation of the magnified image subsequently to a first one of the slide glasses mounted on the stage is picked up by the supply arm, thereafter the first slide glass is picked up from the stage by the discharge arm brought into proximity to the stage by the moving unit, and then the second slide glass is mounted onto the stage by the supply arm.

The microscope system ensures that when the treatment of the first slide glass is finished, the first slide glass can be discharged by the discharge arm having been in a stand-by state in the vicinity of the stage, and, subsequently, the second slide glass can be supplied by the supply arm. Thus, the microscope system ensures that the treatment of the second slide glass can immediately be started, while only requiring a little replacing time, after the treatment of the first slide glass is finished.

The embodiments ensure that when the treatment of the first slide glass is finished, the first slide glass can be discharged by the discharge arm having been in a stand-by state in the vicinity of the stage, and, subsequently, the second slide glass can be supplied by the supply arm. Thus, the embodiments ensure that the treatment of the second slide glass can immediately be started, while only requiring a little replacing time, after the treatment of the first slide glass is finished. Consequently, according to the embodiments, it is possible to realize a conveying device, a conveying method and a microscope system such that replacement of a slide glass can be carried out in a short time.

Additional features and advantages are described herein, and will be apparent from the following Detailed Description and the figures.

BRIEF DESCRIPTION OF THE FIGURES

FIGS. 4A to 4C are diagrams showing the configuration of the multi-sheet cassette;

FIGS. 5A and 5B are diagrams showing the center-of-gravity position of the multi-sheet cassette;

FIG. 11 is a diagrammatic perspective view showing the configuration of a supply arm and a discharge arm;

FIG. 13 is a diagrammatic perspective view for illustrating contraction of the supply arm;

DETAILED DESCRIPTION

Figure 1:
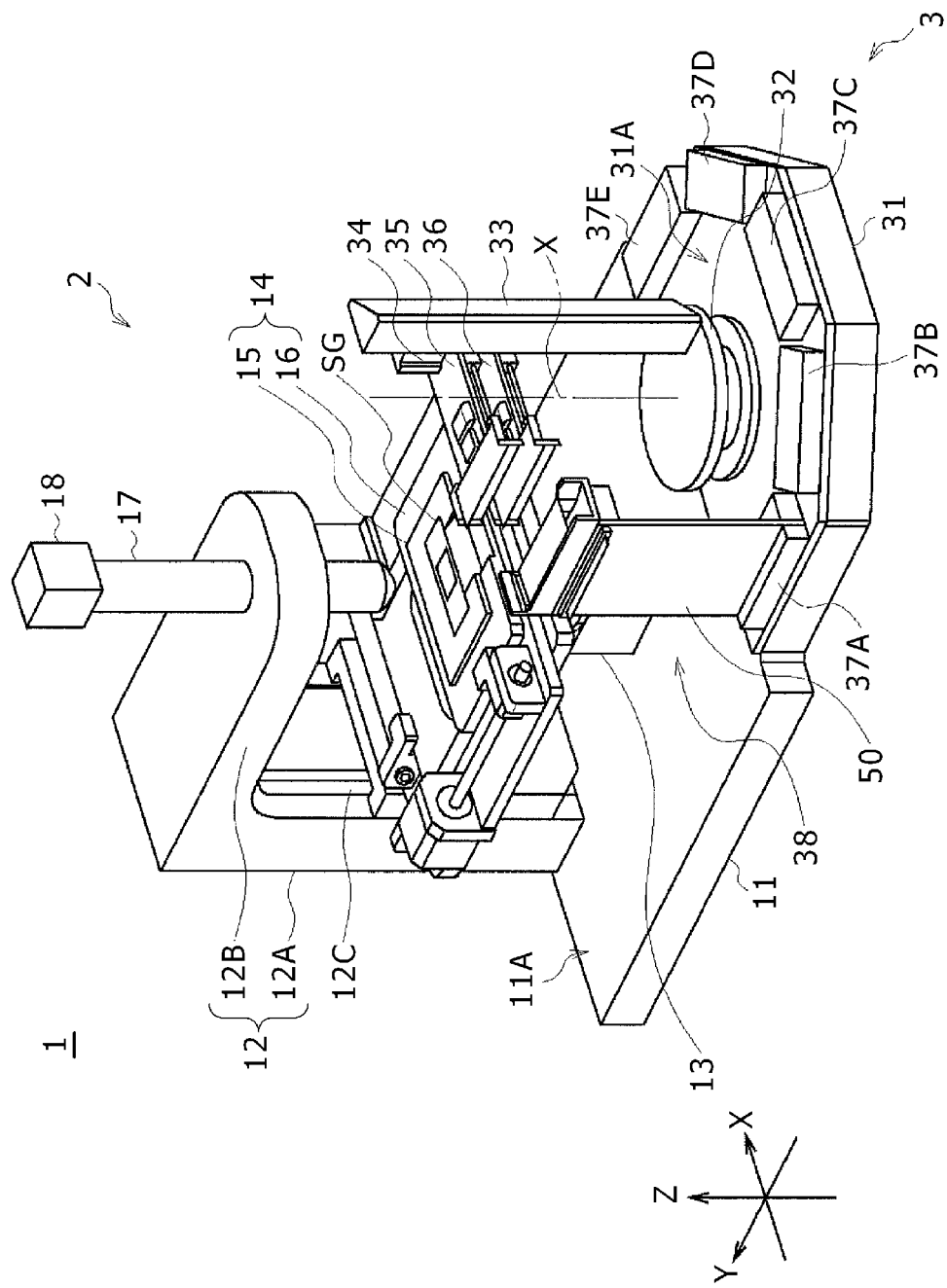
FIG. 1 is a diagrammatic perspective view showing the configuration of a microscope system.

Embodiments of the present application will be described below in detail with reference to the drawings.

1. First Embodiment
2. Other Embodiments
1. First Embodiment
1-1. General Configuration of Microscope System In FIG. 1, a microscope system 1 according to this embodiment includes a microscope unit 2, a conveying unit 3, and a controlling unit (not shown) 4.

The microscope unit 2 picks up an image, magnified in a predetermined scale factor, of a biological sample SPL disposed on a slide glass SG. The conveying unit 3 supplies a slide glass SG onto a stage of the microscope unit 2, and discharges the slide glass SG from the stage. The controlling unit 4 controls the components of the microscope unit 2 and the conveying unit 3, and picks up the image formed through photography by the microscope unit 2.

The slide glass SG has, immobilized thereon by a predetermined immobilizing technique, a biological sample SPL having a tissue section or smear cells of a connective tissue (e.g., blood) or an epithelial tissue or both of them. The tissue section or the smear cells may be stained, as required. Examples of the staining include not only general staining represented by HE (hematoxylin-eosin) staining, Giemsa staining, Papanicolaou staining, etc. but also fluorescent staining such as FISH (Fluorescence In-Situ Hybridization), enzyme-antibody method, etc.

Incidentally, the slide glass SG, in the state of having the biological sample SPL mounted thereon, is coated with an embedding agent, and, further, is covered with a cover glass.

Besides, in the microscope system 1, with respect to the slide glass SG, lengths to be used as references for the longer (major) edge and the shorter (minor) edge are prescribed. Furthermore, a longer edge upper limit and a longer edge lower limit as well as a shorter edge upper limit and a shorter edge lower limit are prescribed, by taking allowable errors into account in addition to the respective lengths of the longer edge and the shorter edge.

Hereinafter, the range from the longer edge lower limit to the longer edge upper limit will be referred to as "longer edge allowable range," and the range from the shorter edge lower limit to the shorter edge upper limit will be referred to as "shorter edge allowable range." Further, the situation in which the longer edge of the slide glass SG is within the longer edge allowable range and the shorter edge is within the shorter edge allowable range is expressed as "(to fall) within the allowable range," whereas the other situations are expressed as "not within the allowable range" or "(to fall) outside of the allowable range."

In the microscope unit 2, a frame section 12 is disposed at a predetermined position on the depth side on an upper surface 11A of a roughly flat plate-like base section 11 disposed substantially horizontally, and a transmitting illumination section 13 is disposed on the user's side of the frame section 12.

The frame section 12 has a prop section 12A extending in a direction (Z-axis direction) orthogonal to the upper surface 11A of the base section 11 and a support unit 12B extending in a direction toward the user's side (Y-axis direction) substantial horizontally in relation to the base section 11 from one end on the upper side of the prop section 12A, and is L-shaped in general form in side view.

A surface on the user's side of the prop section 12A is formed with a guide 12C along the Z-axis direction, and a stage unit 14 is provided which is movable in the Z-axis direction while being engaged with the guide 12C.

The stage unit 14 is provided with a stage 15 on which a slide glass SG is to be mounted and fixed, and a stage driving mechanism 16 which moves the stage 15 in the X-axis, Y-axis and Z-axis directions.

The stage 15 is provided with a plurality of movable-type clip members for fixing or releasing the slide glass SG mounted on the stage 15. The stage 15 is so configured that, if a slide glass SG falling within the allowable range is mounted properly, the slide glass SG can be properly fixed or released by the clip members.

The support unit 12B is provided, at a position substantially on a vertical line of the transmitting illumination section 13, with a lens system 17 having an optical axis coincident with the vertical line and with an image sensing element 18, sequentially in this order toward the upper side (the Z-axis direction side) of the stage 15.

The lens system 17 has a plurality of lenses including an objective lens and an image forming lens, and magnifies in a predetermined scale factor the image of the biological sample SPL arranged on the slide glass SG mounted on the stage 15 and illuminated by the transmitting illumination section 13. The image sensing element 18 is so configured that the image of the biological sample SPL magnified by the lens system 17 is formed on an image sensing plane, whereby the image can be picked up.

1-2. Configuration of Controlling Unit

The controlling unit 4 is so configured as to control the components of the microscope unit 2, to subject the image data on a subject (to be photographed) obtained by image sensing to a predetermined image processing or the like, and to store the thus processed image data into a predetermined storage unit.

Figure 2:
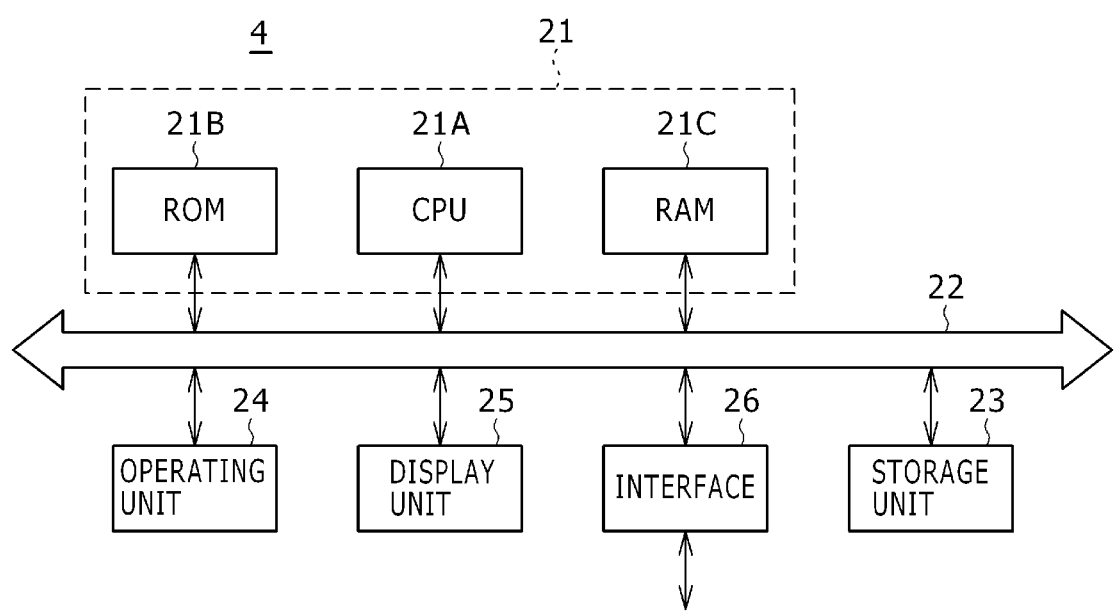
FIG. 2 is a block diagram showing the configuration of a controlling unit.

As shown in FIG. 2, the controlling unit 4 is composed mainly of a control unit 21 which has a CPU (Central Processing Unit) 21A for executing various arithmetic processes, a ROM (Read Only Memory) 21B having data preliminarily stored therein, and a RAM (Random Access Memory) 21C for momentarily storing data.

The control unit 21 is so configured that, while using the RAM 21C as a work area, the CPU 21A executes various programs read from the ROM 21B or the storage unit 23 through a bus 22, and stores various data into the storage unit 23.

The storage unit 23 has, for example, a hard disc drive, an optical disc drive, a flash memory or the like, and is so designed as to be capable of storing therein various large-capacity data such as high-resolution image data.

An operating unit 24 has, for example, a keyboard, various switches, a touch panel or the like, for accepting user's operation inputs and for supplying the control unit 21 with operation instructions representing the contents of the input operations.

A display unit 25 has, for example, a liquid crystal display, an EL (Electro Luminescence) display, a plasma display or the like, which can display various display screens and picked-up image data as images.

An interface 26 is so designed as to perform transmission and reception of various control signals, detection signals, various data or the like between itself and the stage 15, the stage driving mechanism 16 and the image sensing element 18 of the microscope unit 2 as well as the conveying unit 3 to be described later.

1-3. Configuration of Conveying Unit

The conveying unit 3 (FIG. 1) has a configuration based on a base section 31 connected to the base section 11 of the microscope unit 2 and extended in a substantially horizontal direction.

At a substantially central portion of an upper surface 31A of the base section 31, there is provided a roughly circular disk-shaped rotating base 32 capable of rotation about a center axis X substantially perpendicular to the upper surface 31A. From an upper surface 32A of the rotating base 32, a prop 33 substantially triangular prism-like in shape is extended in a direction substantially perpendicular to the upper surface 32A, namely, substantially along the Z-axis direction.

With a side surface of the prop 33 is engaged with a carriage 34 through a movement rail 33A extending along the Z-axis direction. The carriage 34 is driven through a driving mechanism (not shown), based on the control conducted by the controlling unit 4, whereby the carriage 34 can be moved upward or downward in the state of being engaged with the movement rail 33A.

The carriage 34 is fitted with a supply arm 35 for supplying a slide glass SG onto the stage 15 (FIG. 1) and a discharge arm 36 for discharging the slide glass SG from the stage 15 (this will be described in detail later).

On the other hand, pedestals 37A, 37B, 37C, 37D and 37E (hereinafter these are collectively referred to as pedestals 37) substantially rectangular parallelopiped in shape are arranged on the upper surface 31A of the base section 31 at five locations at an angular interval of about 45 degrees along the circumference of a circle having a radius greater than the radius of the rotating base 32, with the imaginary center line X as a center axis.

Each of the pedestals 37A to 37E is so arranged that its longer edge faces the rotation center of the rotating base 32, specifically, that the perpendicular to its longer edge at the center of the longer edge intersects the imaginary center line X.

Figure 3:
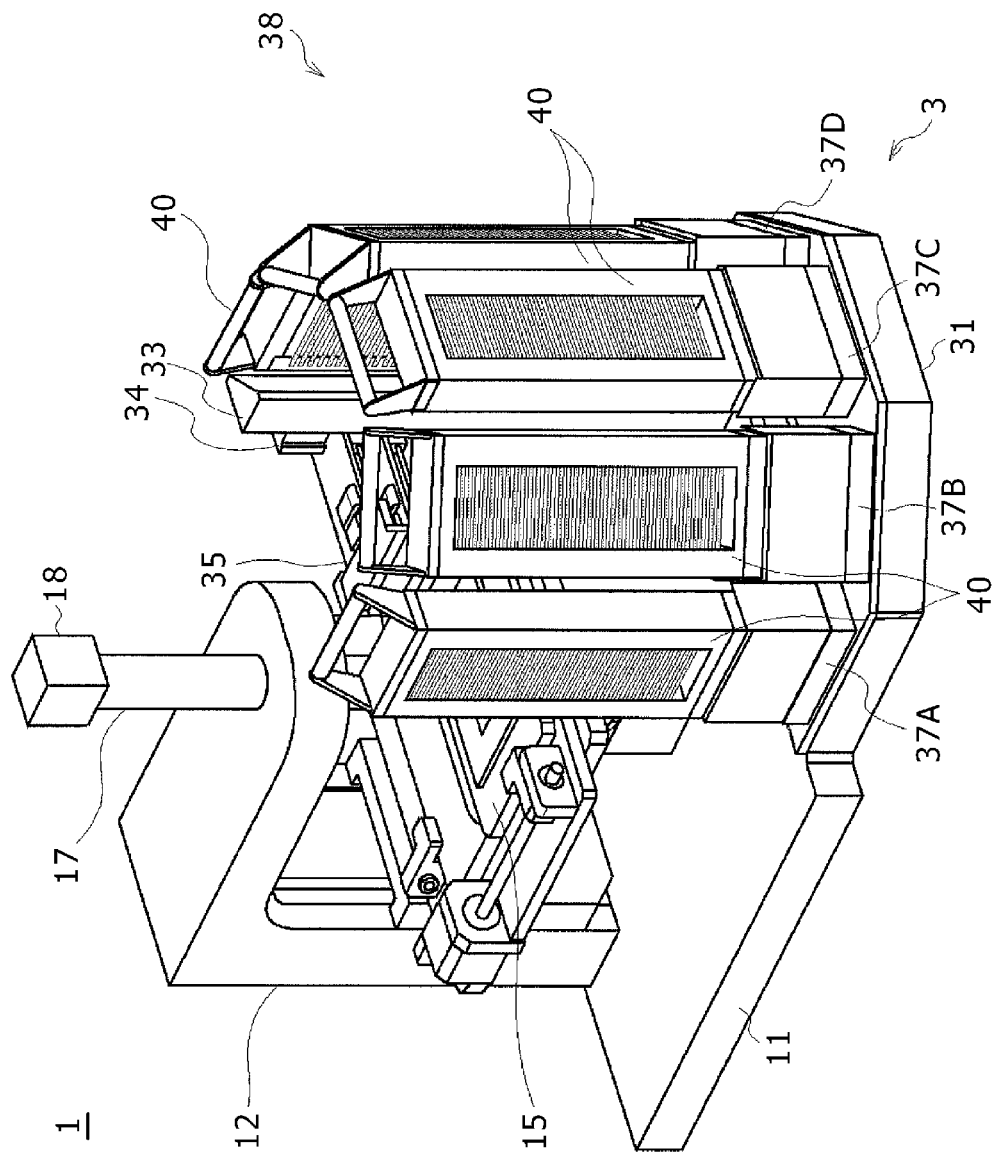
FIG. 3 is a diagrammatic perspective view showing the manner of mounting a multi-sheet cassette.

On the pedestals 37, as shown in FIG. 3 corresponding to FIG. 1, there can be respectively mounted multi-sheet cassettes 40 each serving as a storage device in which up to 60 sheets of slide glasses SG to be supplied onto the stage 15 can be stored. Incidentally, in the case of FIG. 3, the conveying unit 3 is provided with five multi-sheet cassettes 40 so that a total of 300 sheets of slide glasses SG can be stored.

Besides, as shown in FIG. 1, a one-sheet tray 50 as a storage device for storing one sheet of slide glass SG to be supplied onto the stage 15 can also be mounted to the pedestal 37.

Furthermore, the conveying unit 3 can store the slide glasses SG in such a combination manner that, for example, a one-sheet tray 50 is mounted to the pedestal 37A, whereas multi-sheet cassettes 40 are mounted respectively to the pedestals 37B to 37E.

For convenience of description, the multi-sheet cassettes 40 and the one-sheet tray 50 mounted respectively to the pedestals 37 will hereinafter be collectively referred to as storage unit 38.

In practice, the conveying unit 3 is so configured that the supply arm 35 or the discharge arm 36 can be slewed into a desired direction and be adjusted to a desired height, by a combination of a rotating operation of the rotating base 32 and a moving operation of the carriage 34, under the control of the controlling unit 4.

Thus, the conveying unit 3 is so configured that the supply arm 35 or the discharge arm 36 can be made to face the stage 15 (FIG. 1) or can be made to face one of slots in one of the multi-sheet cassettes 40 in the storage unit 38.

1-4. Configuration of Multi-Sheet Cassette

As shown in FIGS. 4A, 4B and 4C, the multi-sheet cassette 40 has a bottom surface section 41, side surface plates 42 and 43 and an top plate 44 which are combined in a box-like shape so as to form an interior space for storing the slide glasses SG therein.

Incidentally, FIG. 4A is a perspective view of the multi-sheet cassette 40 as viewed from a right front upper side, whereas FIGS. 4B and 4C are respectively a front view and a right side view of the same.

The bottom surface section 41 is roughly rectangular parallelopiped in shape, and can be engaged with the pedestal 37 of the conveying unit 3 through an engaging mechanism (not shown). In addition, the bottom surface section 41 has the side surface plates 42 and 43 screwed respectively to both left and right side surfaces thereof.

Each of the side surface plates 42 and 43 is elongated roughly rectangular parallelopiped in overall shape such that its longitudinal direction is oriented in a substantially vertical direction when it is mounted to the bottom surface section 41. In addition, each of the side surface plates 42 and 43 is provided, on the side to be the inside upon assemblage, with substantially horizontal slits for each holding the side of one end in the longitudinal direction of the slide glass SG, with the number of the slits being equal to the number of sheets of slide glasses SG stored in each multi-sheet cassette 40 (namely, 60 sheets) and with the slits being formed repeatedly in the vertical direction.

In other words, the multi-sheet cassette 40 is so designed that the slide glasses SG can each be held in the manner of bridging between the corresponding slits in the side surface plates 42 and 43. In this case, the spaces which are each defined by the slits in the multi-sheet cassettes 40 and each capable of containing one sheet of slide glass SG are so designed as to be able to contain a slide glass SG having the longer edge maximum length and the shorter edge maximum length. The space will be referred to as a slot.

Besides, the surfaces of the slits are formed to be smooth so as to reduce friction thereon. Therefore, in the multi-sheet cassette 40, it is possible, by only sliding the slide glass SG relative to the slits formed in the side surface plates 42 and 43, to smoothly load and unload the slide glass SG into and from the multi-sheet cassette 40.

Furthermore, the side surface plates 42 and 43 are fitted, on the depth side, with plate-like protective plates 42A and 43A for preventing the slide glasses SG from slipping off to the depth side of the slits. In other words, the multi-sheet cassette 40 is so designed that insertion or taking-out of the slide glasses SG can be conducted only on the front side on which the slits are opened.

A top plate 44 is configured in a flat rectangular parallelopiped shape as if obtained by thinning the bottom surface plate 41 in the vertical direction, and is so designed to have the side surface plates 42 and 43 screwed respectively to both left and right side surfaces thereof.

Further, the top plate 44 is fitted, on its left and right side surfaces, with a handle support plate 45 having a roughly triangular thin plate member and a handle support plate 46 formed in left-right symmetry with the handle support plate 45. Each of the handle support plates 45 and 46 is formed in such a shape that the upper-side vertex is deviated from the base toward the user's side.

Between the upper-side vertexes of the handle support plates 45 and 46, a roughly cylindrical grip section 47 interconnecting the vertexes is bridgingly provided.

Here, as shown in a schematic side view in FIG. 5A, the center of gravity of the multi-sheet cassette 40 is roughly at the position of a point P1, both in a state of being not loaded with the slide glasses SG (namely, in an empty state) and in a state of being fully loaded with sixty slide glasses SG.

In addition, the grip section 47 is so designed that the angle θ between the vertical line and an imaginary straight line L1 interconnecting the center-of-gravity point P1 of the multi-sheet cassette 40 as a whole and the center point P2 of the grip section 47 is in the range of 4 to 6 degrees.

Therefore, as shown in FIG. 5B, when the grip section 47 of the multi-sheet cassette 40 is gripped by the user or the like, the center-of-gravity point P1 is located substantially just under the center point P2 of the grip section 47, so that the multi-sheet cassette 40 is inclined to have its front-side surface oriented slightly upward.

Specifically, during when the multi-sheet cassette 40 is transported, simple gripping of the grip section 47 by the operator ensures that the depth side on which the protective plates 42A and 43A are attached can be oriented downward and the side on which the slits are opened can be oriented upward. Consequently, it is possible to greatly reduce the possibility that the slide glasses SG might fall during transportation of the multi-sheet cassette 40.

Besides, when the multi-sheet cassette 40 is mounted on a horizontal base or mounted to the pedestal 37, it is set substantially upright (vertical), so that the slits are returned to be horizontal. Accordingly, by simply applying a comparatively weak force to each slide glass SG in a horizontal direction, the slide glass SG can be inserted into the multi-sheet cassette 40 or taken out of the multi-sheet cassette 40 through sliding in the slit.

Incidentally, the angle θ of the multi-sheet cassette 40 is set to be not less than 4 degrees so as to prevent the slide glasses SG from slipping off when the grip section 47 is gripped by the operator or the like. In addition, the angle θ is set to be not more than 6 degrees so as to prevent positional deviation (shifting) of the cover glass on the slide glass SG immediately after preparation thereof.

1-5. Configuration of One-Sheet Tray

Figure 6:
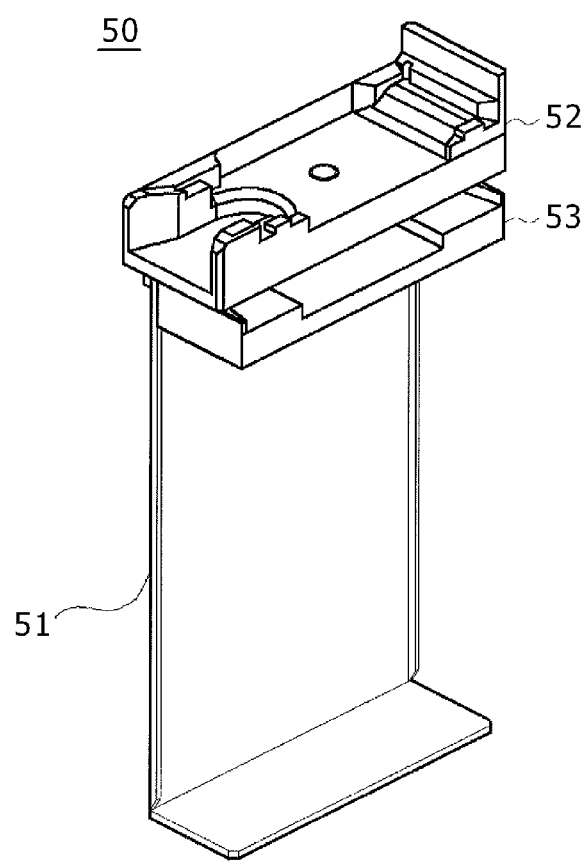
FIG. 6 is a diagram showing the configuration of a one-sheet tray.

As shown in FIG. 6, a one-sheet tray 50 has a configuration in which a supply tray 52 is provided in the vicinity of an upper end of a thin plate-like support plate 51, and a discharge tray 53 is provided under the supply tray 52.

1-5-1. Configuration of Supply Tray

Figure 7:
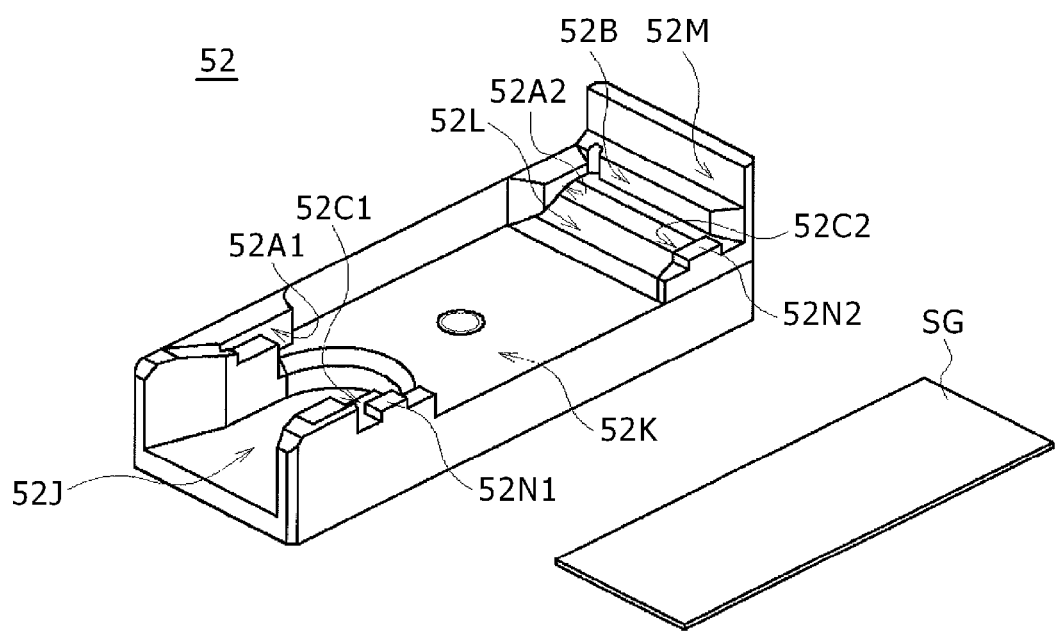
FIG. 7 is a diagrammatic perspective view showing the configuration of a supply tray.
Figure 8:
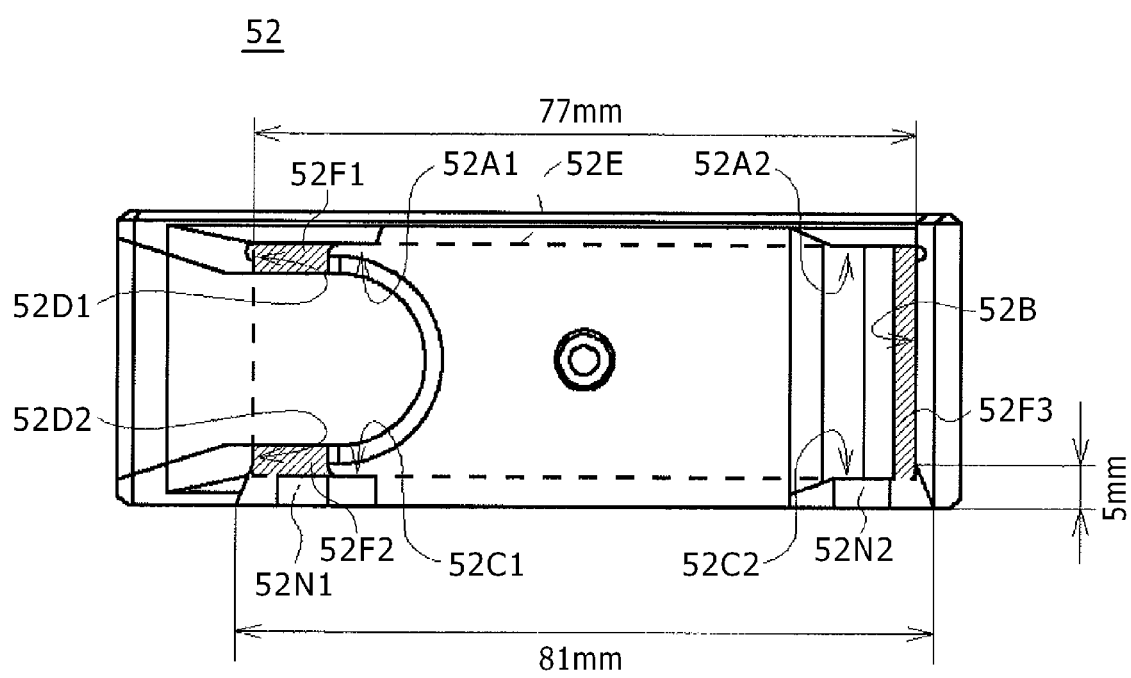
FIG. 8 is a diagrammatic top plan view showing the configuration of the supply tray.

As a perspective view is shown in FIG. 7 and a top plan view is shown in FIG. 8, the supply tray 52 is configured to be substantially rectangular parallelopiped in overall shape, and is shaped as if its upper side were cut in conformity with the slide glass SG and a space necessary for mounting the slide glass SG.

The supply tray 52 is so designed as to hold a slide glass SG in a holding space 52E (FIG. 8) surrounded by inside walls 52A1, 52A2, 52B, 52C1, 52C2, 52D1 and 52D2.

In this instance, the supply tray 52 support the slide glass SG on the lower side of the latter by support surfaces 52F1, 52F2 and 52F3 (hatched in FIG. 8). In addition, the supply tray 52 is opened on the upper side of the holding space 52E.

In practice, the supply tray 52 is so designed that the slide glass SG is mounted thereon from the upper side according to the holding space 52E by an operator's manual work, and, thereafter, the slide glass SG is gripped and taken out by the supply arm 35.

Besides, the supply tray 52 is provided with a space 52J ensuring that a finger for pinching the slide glass SG from the lower side can escape when the operator mounts the slide glass, and with a space 52K for insertion of a tip portion of the supply arm 35 (FIG. 1).

Further, the supply tray 52 is provided, on the opposite side to the space 52J with reference to the longitudinal direction, with an inclined surface section 52L permitting the operator to mount the slide glass SG so as to positionally adjust it to the holding space 52E while sliding its end surface in its longitudinal direction, and with an abutting plate 52M.

Meanwhile, the supply tray 52 is so designed that the longer edge and the shorter edge of the holding space 52E surrounded by the inside walls 52A1, 52A2, 52B, 52C1, 52C2, 52D1 and 52D2 are set to be respectively comparable to the longer edge upper limit and the shorter edge upper limit of the slide glass SG.

Specifically, the holding space 52E of the supply tray 52 is so designed that a slide glass SG falling outside of the allowable range, for example, a slide glass SG having a cover glass or an embedding agent protruding sideways or a slide glass SG having a longer edge greater than the longer edge upper limit, cannot be mounted in the holding space 52E.

Incidentally, the supply tray 52 ensures that a slide glass SG having a longer edge smaller than the longer edge upper limit or having a shorter edge smaller than the shorter edge upper limit would chatter in the holding space 52E, so that the operator can clearly recognize that the longer edge or the shorter edge of the slide glass is smaller than prescribed.

In addition, the size of the holding space 52E is so set as to prevent, as assuredly as possible, the formation of a superfluous space in the surroundings of the slide glass SG, thereby limiting the mounting range of the slide glass SG to a certain extent. With such a configuration, the supply tray 52 ensures that the slide glass SG is positioned in a comparatively narrow range and can be properly gripped by the supply arm 35 (FIG. 1).

Further, in the supply tray 52, the steps between partial upper surfaces 52N1 and 52N2 continuous with the inside walls 52C1 and 52C2 and the support surfaces 52F2 and 52F3 are restricted to be low. Incidentally, the steps are set to a height corresponding, for example, to the total thickness of one or two slide glasses SG.

This ensures in the supply tray 52 that a slide glass SG falling outside of the allowable range would not make proper contact with the support surfaces 52F1, 52F2 and 52F3, and a part thereof would ride onto the partial upper surface 52N1 or 52N2, whereby such a slide glass SG can be put into an instable state, so to speak, a "chattering" state.

With such a configuration, the supply tray 52 permits the operator to recognize through tactile sensation, visual sensation or auditory sensation that the slide glass SG is not properly contained in the holding space 52E, namely, that the slide glass SG is instable and is exceeding the prescribed size.

Further, the spacing between the support surfaces 52F1, 52F2 and the support surface 52F3 of the supply tray 52 is set to be comparable to the longer edge lower limit of the slide glass SG. With this configuration, the supply tray 52 ensures that a slide glass SG which has the length of the longer edge being below the longer edge lower limit and which may therefore slip off from the supply arm 35 or the stage 15 (FIG. 1) cannot be mounted properly.

In this instance, the supply tray 52 permits the operator to recognize through tactile sensation, visual sensation or auditory sensation that the slide glass SG has the longer edge less than the longer edge lower limit, based on the situation in which the slide glass SG is not properly supported by the support surfaces 52F1, 52F2 and 52F3 but is in an instable state.

Thus, the supply tray 52 is so configured that a slide glass SG falling outside of the allowable range cannot be properly mounted thereon. With such a configuration, the supply tray 52 permits the operator or the like to easily recognize a slide glass SG falling outside of the allowable range and to immediately understand that the image of the slide glass SG cannot be picked up by the microscope system 1.

1-5-2. Configuration of Discharge Tray

Figure 9A:
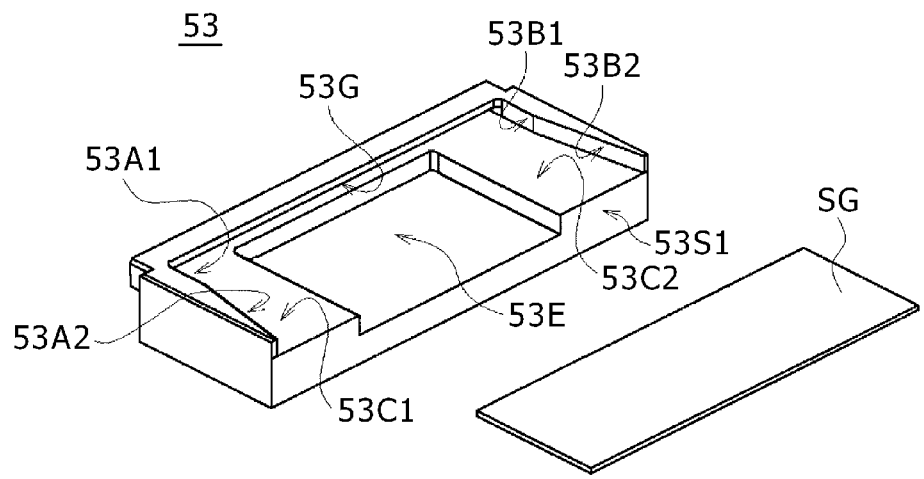
FIGS. 9A to 9C are diagrammatic perspective views showing the configuration of a discharge tray.
Figure 9B:
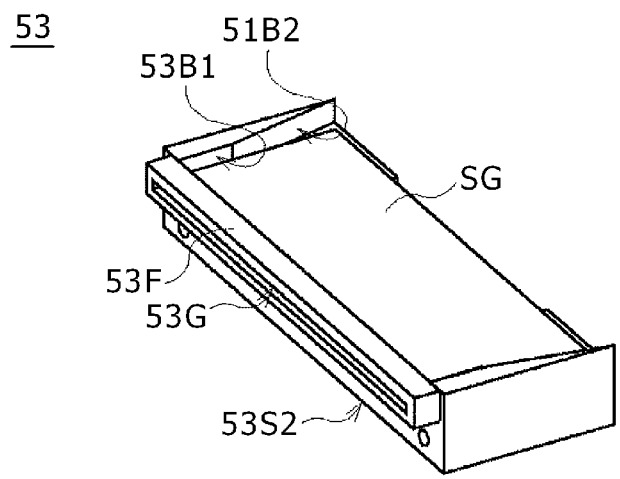
Figure 10:
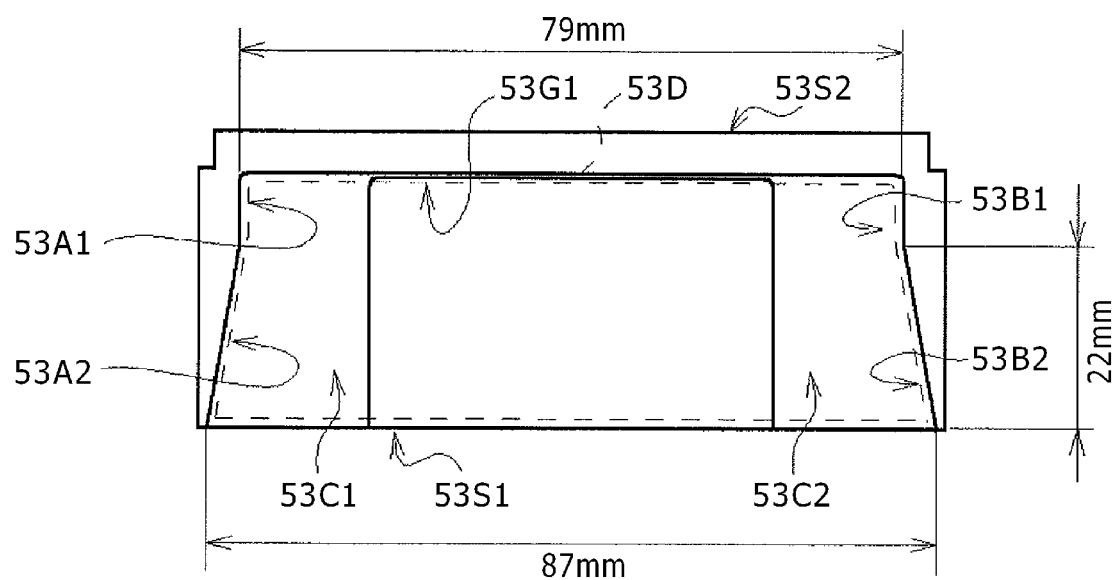
FIG. 10 is a diagrammatic top plan view showing the configuration of the discharge tray.

As perspective views are shown in FIGS. 9A and 9B and a top plan view is shown in FIG. 10, the discharge tray 53 is roughly rectangular parallelopiped in overall shape, and has a shape as if its upper side were cut in conformity with the slide glass SG and a space necessary for mounting the slide glass SG.

For convenience of description, hereinafter, of that side surface of the discharge tray 53 into which the discharge arm 36 is to be inserted will be referred to as an insertion surface 53S1, and the opposite side surface as a discharge surface 53S2.

The discharge tray 53 is so designed as to hold a slide glass SG in a holding space 53D which is defined between inside surfaces 53A1, 53A2 and inside surfaces 53B1, 53B2 corresponding to the shorter edge side of the slide glass SG, is opened at a portion corresponding to the longer edge side of the slide glass SG and is partitioned by inside bottom surfaces 53C1, 53C2.

While the inside surfaces 53A1 and 53B1 are set to be substantially parallel to each other, the inside surfaces 53A2 and 53B2 are inclined so that the spacing therebetween is broadened as one approaches the insertion surface 53S1.

In addition, between the inside bottom surfaces 53C1 and 53C2 is formed a space 53E for insertion therein of a tip portion of the discharge arm 36 (FIG. 1) from the insertion surface 53S1 side.

On the other hand, on the upper side of the discharge surface 53S2 is formed a projected section 53F which is projected as compared with the surroundings thereof. The projected section 53F has bored therein a hole 53G penetrating from the holding space 53D and having a passage section such as to permit the slide glass SG to pass therethrough perpendicularly to the longer edge of the slide glass SG.

In practice, when a slide glass SG is conveyed from the insertion surface 53S1 side of the discharge tray 53 by the discharge arm 36, the discharge tray 53 holds the slide glass SG in its holding space 53D.

Here, a state ideal for a slide glass SG at the time of insertion thereof into the discharge tray 53 by the discharge arm 36 is a state in which the advancing direction of the discharge arm 36 and the shorter edge of the slide glass SG are substantially parallel to each other whereas the insertion surface 53S1 and the longer edge of the slide glass SG are substantially parallel to each other. Hereinafter, this state will be referred to as the ideal insertion state.

Due to the influences of a gripping motion of the discharge arm 36 at the time of taking out the slide glass SG from the stage 15 or the like, however, the slide glass SG may be inserted into the discharge tray 53 while being in a state of being deviated from the ideal insertion state in the longer edge direction or in a state of being inclined (turned) in a horizontal direction from the ideal insertion state.

In relation to this point, the discharge tray 53 is so configured that the spacing between the inside surfaces 53A2 and 53B2 at the portion on the insertion surface side is sufficiently longer (wider) than the prescribed length of the slide glass SG and is made shorter (narrower) as one advances deeper into the inside. Accordingly, the discharge tray 53 permits assured insertion of the slide glass SG into the holding space 53D.

In this instance, the discharge tray 53 ensures that when the slide glass SG is inserted into the holding space 53D from the insertion surface 53S1 side, the slide glass SG is made to make contact with the inside surfaces 53A2 and 53B2 which are so formed that the spacing therebetween is gradually narrowed along the inside direction.

With the discharge tray 53 configured in this manner, a positional deviation or an inclination, if any, of the slide glass SG can be gradually corrected in such a manner that the shorter edge of the slide glass SG is gradually brought to a state of being substantially parallel to the advancing direction of the slide glass SG.

Figure 9C:
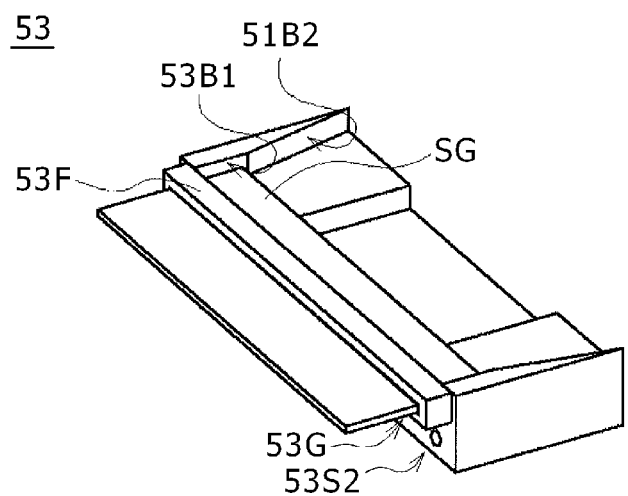

Thereafter, in the discharge tray 53, the longer edge on the insertion surface side of the slide glass SG held in the holding space 53D is pushed in by a tip portion of the discharge arm 36, whereby a part of the slide glass SG is exposed from the hole 53G, as shown in FIG. 9C.

With this configuration, the discharge tray 53 permits the operator to easily grip and take out the slide glass SG, which is located on the lower side of the supply tray 52 and is therefore hard to take out as it is.

Thus, in the one-sheet tray 50, a tray for supply and a tray for discharge are provided independently from each other, and, further, the supply tray 52 and the discharge tray 53 are set different in shape according to the purposes thereof.

1-6. Configuration of Supply Arm and Discharge Arm

Now, the supply arm 35 and the discharge arm 36 will be described below. The supply arm 35 and the discharge arm 36 are similar to each other in configuration, and are attached to the carriage 34 in the state of extending in the same direction and being overlappingly arranged on the upper and lower sides.

1-6-1. Configuration of Supply Arm

As shown in FIG. 11, the supply arm 35 includes an arm fixation section 60 to be fixed to the carriage 34, and an arm movement section 70 which is moved relative to the arm fixation section 60 and by which the slide glass SG can be gripped.

The arm fixation section 60 is composed chiefly of a roughly rectangular parallelopiped arm base 61 which has a flat shape being thin in the vertical direction. The arm base 61 is mounted to the carriage 34 (FIG. 1) through its mounting surface 61A, which is a side surface on the side of one end in regard of the longitudinal direction thereof.

Hereafter, in the arm base 61, the direction from the mounting surface 61A side toward the opposite side will be defined as a Q-axis direction, the direction from the lower side toward the upper side will be defined as an R-axis direction, and one direction orthogonal to both the Q-axis and the R-axis will be defined as a P-axis direction.

Near both side surface portions in regard of the P-axis direction of the arm base 61, roughly cylindrical moving shafts 62A and 62B are provided along the Q-axis direction.

In the inside of a roughly central portion of the arm base 61, a translation section 63 having a motor or the like is provided, and a rotational driving force thereof is transmitted to a gear 63A provided to protrude to the upper side (+R direction) beyond the upper surface of the arm base 61.

At a predetermined location on the upper surface of the arm base 61, a sensor 64 is provided for detecting that the arm movement section 70 is located at a predetermined position in a −Q direction.

In addition, to a side surface on the +Q side of the arm base 61, a fall-off preventive guide 65 shaped as if obtained by bending a plate-like member is mounted.

Of the fall-off preventive guide 65, a flat plate section 65A having a flat plate-like shape is mounted to the arm base 61 substantially in parallel to a side surface on the +Q side of the arm base 61, with its longitudinal direction coinciding with the P-axis direction.

At both end portions in regard of the P-axis direction of the flat plate section 65A, guide sections 65B and 65C for preventing the slide glass SG from falling off in the P-axis direction are provided.

The guide section 65B has a structure wherein a coupling plate 65B1 having a roughly rectangular shape, having a length of about two times the length of the flat plate section 65A in the R-axis direction and being short in the Q-axis direction is provided at the +P side end of the flat plate section 65A in the state of being flush with the flat plate section 65A at the −R side end surface and extending to be inclined slightly to the +P direction rather than the +Q direction, namely, to be opened outward.

At the upper half of the coupling plate 65B1, a rectangular guide plate 65B2 having a length comparable to the length of the flat plate section 65A in the R-axis direction and a length comparable to the length of the shorter edge of the slide glass SG in the Q-axis direction is provided to extend toward the −Q direction.

In addition, to a −Q side position of the +P side surface of the guide plate 65B2, an extension guide plate 65B3 composed of a rectangular member roughly the same as the guide plate 65B2 in shape is partly overlappingly attached by a screw (not shown) or the like. Further, the extension guide plate 65B3 is bent to the −P side (namely, the inner side), in the vicinity of a −Q side terminal portion of the guide plate 62B2.

The guide section 65C is configured substantially in symmetry with the guide section 65B about the Q axis and the R axis, and has a coupling plate 65C1, a guide plate 65C2 and an extension guide plate 65C3 which correspond to the coupling plate 65B1, the guide plate 65B2 and the extension guide plate 65B3, respectively.

Here, the spacing between the guide plates 65B2 and 65C2 is regulated to be comparable to the longer edge upper limit for the slide glass SG. Therefore, the space defined between the guide sections 65B and 65C serves as a space in which a slide glass SG falling within the allowable range can be held. Hereafter, this space will be referred to as the holding space 65D.

Due to the inclinations of the coupling plates 65B1 and 65C1, the holding space 65D is so shaped that, at its portion on the +Q side, it is broadened in the P-axis direction as one advances in the +Q direction.

On the other hand, the arm movement section 70 is composed chiefly of an arm sliding body 71 which is slid along the Q-axis direction relative to the arm base 61 and is thereby moved substantially in parallel to the upper surface of the arm base 61.

The arm sliding body 71 has a thin plate shape having lengths comparable to the lengths of the arm base 61 in the Q-axis direction and the P-axis direction, and its peripheral side portions are bent to the upper side (+R side) so as to secure strength.

The arm sliding body 71 is formed, on the +Q side, with a smooth mount surface 71BX on which to mount the slide glass SG. The mount surface 71BX is provided, at a +Q side end portion thereof, with fixing claws 71BY as fixing grip elements which rise up to the upper side (+R side).

In addition, the arm sliding body 71 is provided, in its portion ranging from the center toward the −Q side, with a roughly elliptic hole 71A having a hole diameter permitting the gear 63A to escape therethrough and having a major diameter along the Q-axis direction. The hole 71A is provided, on a +P-side side surface thereof, with a rack 71AX for meshing with the gear 63A.

Further, the arm sliding body 71 is fitted, under the −Q side thereof, with bearing sections 72A and 72B corresponding respectively to the moving shafts 62A and 62B.

In the supply arm 35 thus configured, the gear 63A is rotationally driven by the translation section 63 on the basis of the control by the controlling unit 4, whereby the arm movement section 70 can be slid along the Q-axis direction relative to the arm fixation section 60.

For example, through a contracting operation of the supply arm 35 wherein the arm movement section 70 is slid in the −Q direction in the condition where a slide glass SG is mounted on the mount surface 71BX, the slide glass SG can be moved so as to be drawn into the holding space 65D.

In this instance, the supply arm 35 ensures that, even if the slide glass SG is mounted at a position somewhat deviated in the P-axis direction, the position of the slide glass SG in regard of the P-axis direction can be corrected toward the center, by drawing the slide glass SG while keeping it in contact with the guide section 65B or 65C.

Further, the arm sliding body 71 is provided at its upper surface with a clamp unit 73 at a position deviated in the −Q direction from the fixing claws 71BY to leave therebetween a spacing comparable to the shorter edge upper limit for the slide glass SG, slightly on the +Q side relative to the center of the arm sliding body 71.

Figure 12A:
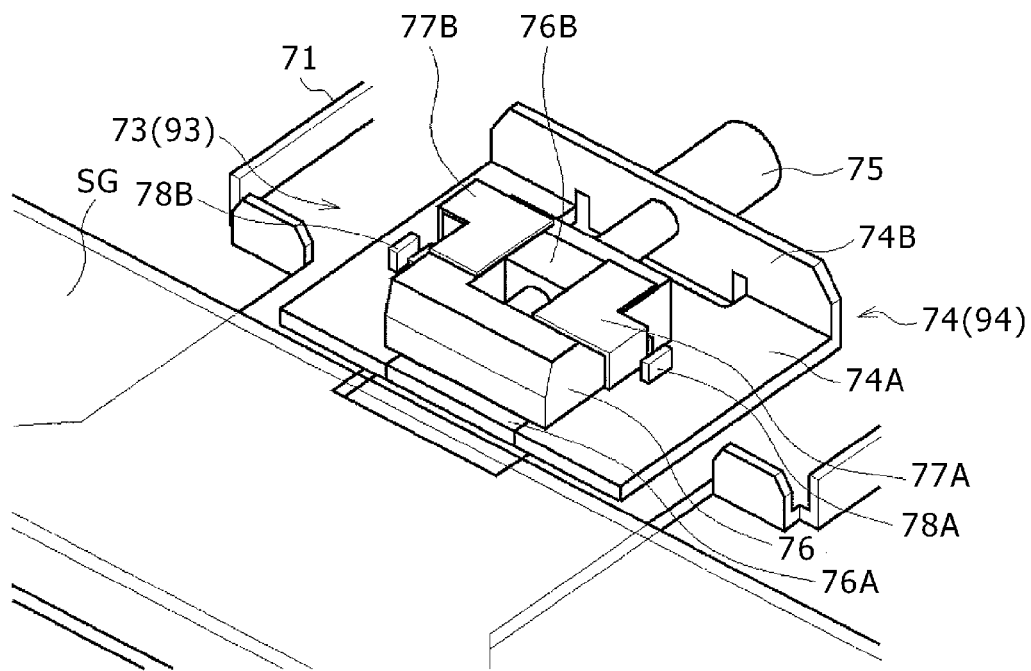
FIGS. 12A and 12B are diagrammatic perspective views for illustrating the configuration and movement of a clamp block.

As shown in FIG. 12A, the clamp unit 73 is composed of a combination of a plurality of component parts, with a mounting plate 74 as a chief member. The mounting plate 74 has a bottom plate section 74A roughly flat plate-like in overall shape and mounted to the upper surface of the arm sliding body 71, and a side plate section 74B extended toward the upper side (+R side) from an end portion on the −Q side of the bottom plate section 74A.

On the −Q side of the side plate section 74B, a clamp motor 75 is mounted. An output shaft of the clamp motor 75 is extended in the +Q direction to penetrate a hole bored in the side plate section 74B, and is formed with a spiral groove.

On the other hand, in an area ranging from the center to a +Q-side end portion of the upper surface of the bottom plate section 74A, a clamp block 76 as a moving grip element having a flat roughly rectangular parallelopiped shape is provided so that it can be slid along the Q-axis direction relative to the bottom plate section 74A. The clamp block 76 is provided with a hole penetrating the inside thereof from a −Q-side side surface thereof, and is provided therein with a bearing 76B for screw engagement with the output shaft of the clamp motor 75.

In addition, the clamp block 76 is provided, under the +Q-side side surface thereof, with a projected section 76A composed of a prism projected relative to the surroundings and elongated in the Q-axis direction. The length in the R-axis direction (namely, the thickness) of the projected section 76A is set to be comparable to or slightly smaller than the thickness of the slide glass SG exclusive of the cover glass.

In the clamp unit 73 thus configured, with the clamp motor 75 driven on the basis of the control by the controlling unit 4, the clamp block 76 can be moved in the +Q direction or the −Q direction.

Here, in the clamp unit 73, the spacing between the fixing claws 71BY and the projected section 76A of the clamp block 76 (hereafter, this spacing will be referred to as the grip spacing (or grip interval)) is varied between the prescribed length of the shorter edge of the slide glass SG and a length slightly extended from the prescribed length. In other words, in the clamp unit 73, the movable range of the clamp block 76 is set to be comparatively narrow. Therefore, in the clamp unit 73, the moving operation of the clamp block 76 can be completed in a short time.

In addition, the clamp unit 73 is so configured that the clamp block 76 is driven by a comparatively strong force.

In the case where the slide glass SG is practically gripped by the supply arm 35 (FIG. 11), the spacing between the projected section 76A and the fixing claws 71BY is widened preliminarily by moving the clamp block 76 in the −Q direction, as shown in FIG. 12A, before the slide glass SG is mounted on the mount surface 71BX. Hereafter, the operation of moving the clamp block 76 in the −Q direction will be referred to as the releasing operation.

Thereafter, the supply arm 35 moves the slide glass SG into the holding space 65, as shown in FIG. 13, by moving the arm movement section 70 in the −Q direction to effect contraction, in the condition where the slide glass SG is mounted on the mount surface 71BX.

Figure 12B:
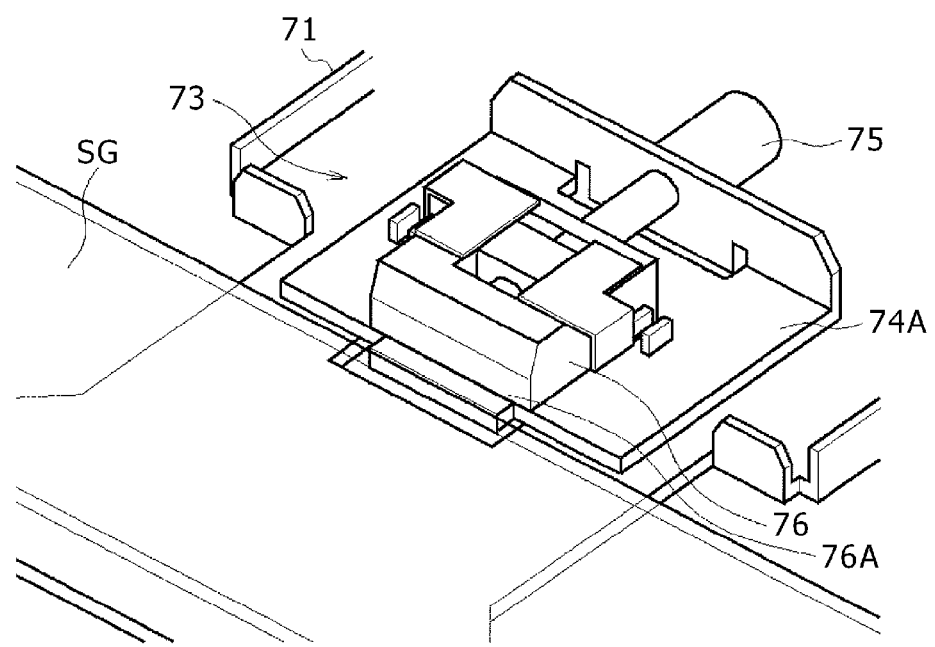

Subsequently, in the supply arm 35, the clamp block 76 is moved in the +Q direction with a predetermined torque, as shown in FIG. 12B. Hereafter, the operation of moving the clamp block 76 in the +Q direction will be referred to as the pressing operation.

By this operation, the supply arm 35 clamps the slide glass SG (which is held in the holding space 65D) between the projected section 76A of the clamp block 76 and the fixing claws 71BY, whereby the slide glass SG can be fixed on the supply arm 35.

In this instance, the projected section 76A abuts on the slide glass SG itself. Therefore, even if the cover glass on the slide glass SG is protruding sideways, the projected section 76A would not exert any pressing force on the cover glass and, therefore, would not break the cover glass.

Hereafter, the operation of the arm movement section 70 to fix the slide glass SG by clamping it between the projected section 76A of the clamp block 76 and the fixing claws 71BY will be referred to as the gripping operation.

Besides, in the following, the mechanism for gripping the slide glass SG which includes the mount surface 71BX, the fixing claws 71BY and the projected section 76A of the clamp block 76, on the tip side of the arm movement section 70, will be referred to as the gripping unit 70A.

Meanwhile, on the +P side and the −P side on the upper surface of the clamp block 76 (FIG. 12A), there are respectively provided detection section pieces 77A and 77B formed by bending sheet-like members into a roughly L shape in side view.

The detection section piece 77A is in a state wherein a part thereof is fixed to the upper surface of the clamp block 76, and a +P-side tip portion thereof is bent to the lower side (−R side) at a portion protruding in the +P direction beyond the +P-side side surface of the clamp block 76.

Besides, the detection section piece 77B is substantially the same as the detection section piece 77A in shape, and is mounted as if the detection section piece 77A were rotated by half turn about the R axis so that a −P-side tip portion thereof is protruded in the −P direction beyond the −P-side side surface of the clamp block 76.

Further, to those parts of the bottom plate section 74A which correspond respectively to the detection section pieces 77A and 77B, sensors 78A and 78B are mounted for respectively detecting that the detection section pieces 77A and 77B are located at predetermined positions, namely, that the grip spacing is equal to a predetermined spacing.

Incidentally, in the clamp unit 73, the mounting positions of the sensors 78A and 78B are so set as to make it possible to detect respectively that the grip spacing is less than the shorter edge lower limit for the slide glass SG and that the grip spacing is more than the shorter edge upper limit for the slide glass SG.

With the supply arm 35 thus configured, when the slide glass SG is gripped, it is possible to detect whether or not the length of the shorter edge of the slide glass SG is within the shorter edge allowable range.

In this manner, the supply arm 35 is so designed that the slide glass SG can be moved into the holding space 65D by the contracting operation of sliding the arm movement section 70 in the −Q direction and that the slide glass SG can be gripped by the gripping operation of the gripping unit 70A.

1-6-2. Basic Conveying Operation of Supply Arm

Figure 14:
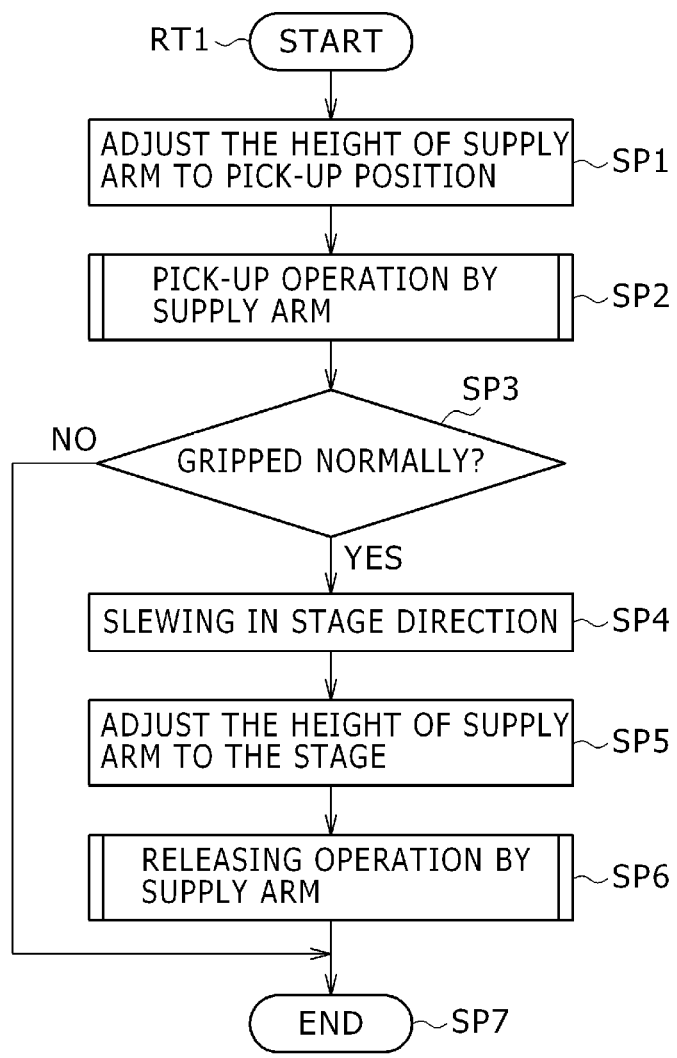
FIG. 14 is a flow chart showing the procedure of a basic conveying operation process of the supply arm.
Figure 15:
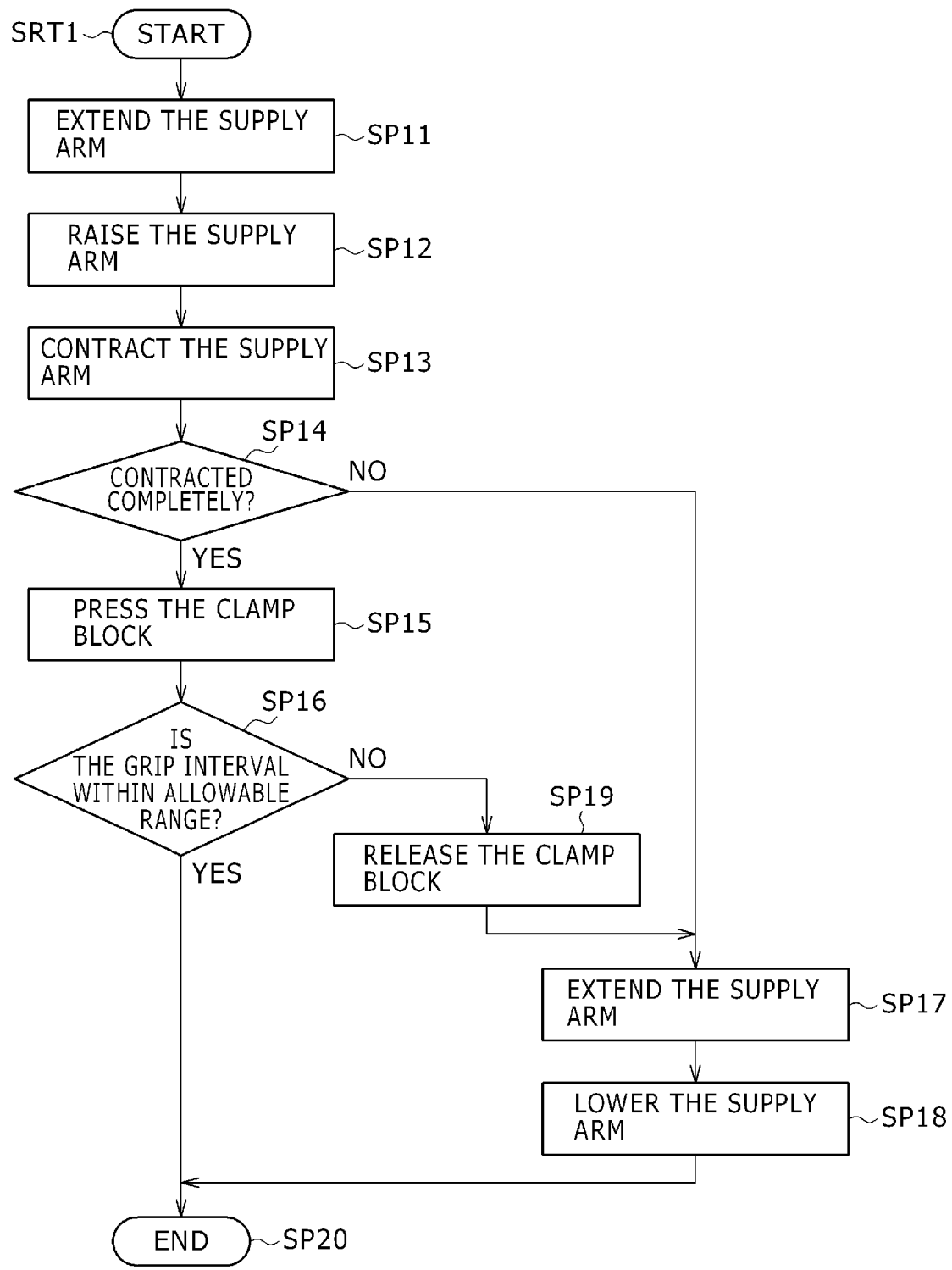
FIG. 15 is a flow chart showing the procedure of a pick-up operation process by the supply arm.
Figure 16:
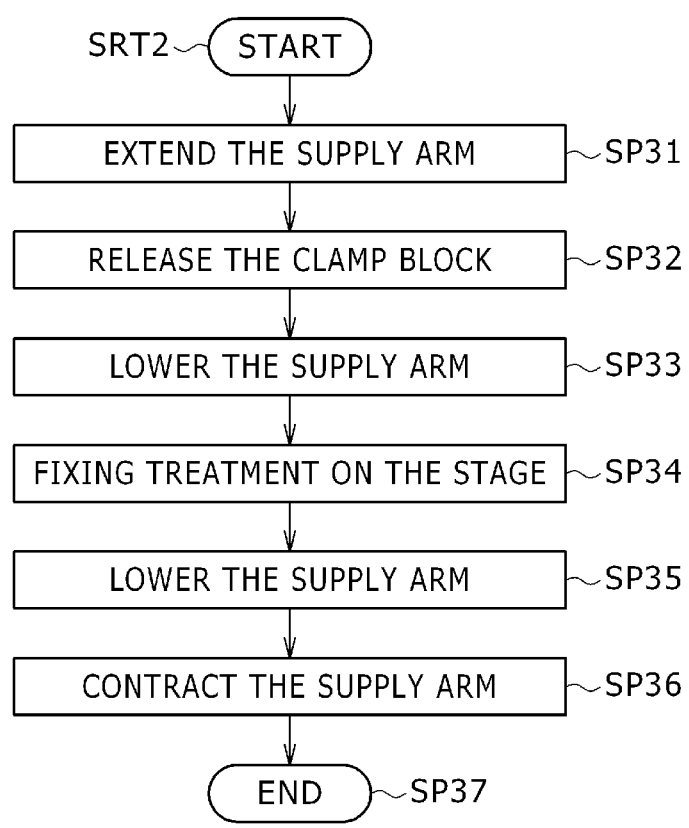
FIG. 16 is flow chart showing the procedure of a releasing operation process by the supply arm.

In practice, the controlling unit 4 (FIG. 2) basically executes a control according to the flow charts shown in FIGS. 14 to 16, in the case of conveying a slide glass SG by the supply arm 35.

Incidentally, here, description will be made by taking as an example the case of conveying onto the stage 15 a slide glass SG stored in the storage unit 38 having the multi-sheet cassette 40. Besides, in the following, the slide glass SG serving as an object (target) of conveyance will be referred to as the target slide glass (SGT).

For example, upon receiving a starting instruction for a conveying operation by the supply arm 35 through the operating unit 24, the control unit 21 of the controlling unit 4 starts routine RT1 (FIG. 14) and proceeds to step SP1.

In step SP1, the control unit 21 moves the carriage 34 in the vertical direction, so as to adjust the height of the supply arm 35 to the height of a storage part where the target slide glass SGT is stored, and proceeds to the next step SP2.

In this instance, the control unit 21 controls the height of the carriage 34 so that upper end portions of the fixing claws 71BY (FIG. 11) of the supply arm 35 are set slightly below the lower surface of the target slide glass SGT.

In step SP2, the control unit 21 proceeds to a sub-routine SRT1 (FIG. 15) in order to perform a pick-up operation process by the supply arm 35, and enters step SP11.

Figure 17:
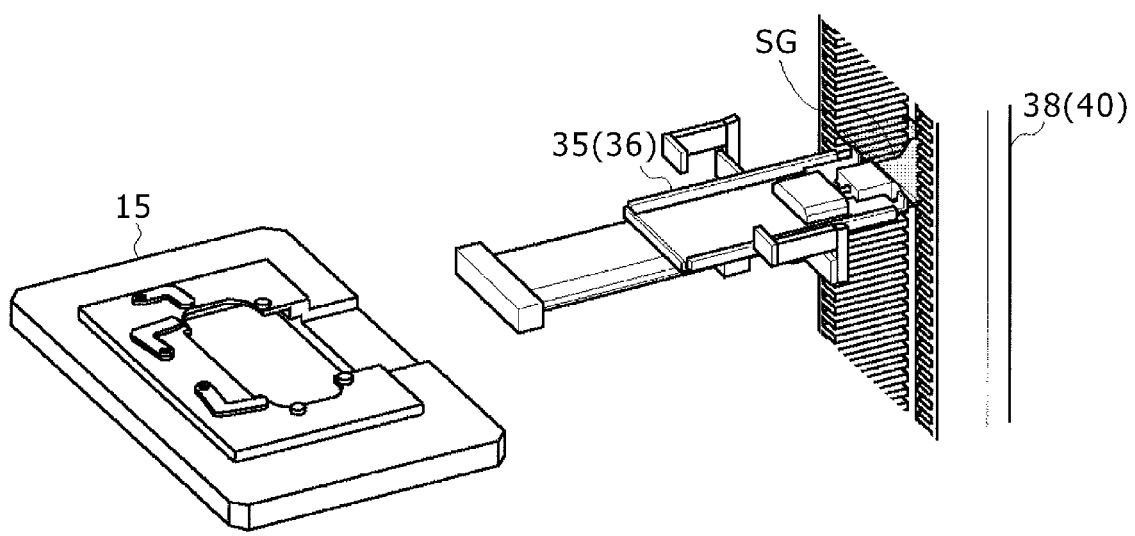
FIGS. 17 to 21 are diagrammatic perspective views showing basic conveying operations (1) to (5)

In step SP11, the control unit 21 controls the translation section 63 of the supply arm 35, to thereby effects an extending operation of sliding the arm movement section 70 (FIG. 11) in the +Q direction as shown in FIG. 17, and proceeds to the next step SP12.

In this case, the mount surface 71BX of the arm movement section 70 is located substantially just under the target slide glass SGT.

In step SP12, the control unit 21 moves the carriage 34 upward so as to raise the supply arm 35, and proceeds to the next step SP13.

In this instance, the supply arm 35 causes the target slide glass SGT to be mounted on the mount surface 71BX, and causes both end portions in regard of the longitudinal direction of the target slide glass SGT to be raised from the slit portions of the multi-sheet cassette 40.

In step SP13, the control unit 21 controls the translation section 63 of the supply arm 35 to perform a contracting operation, and proceeds to the next step SP14.

Figure 18:
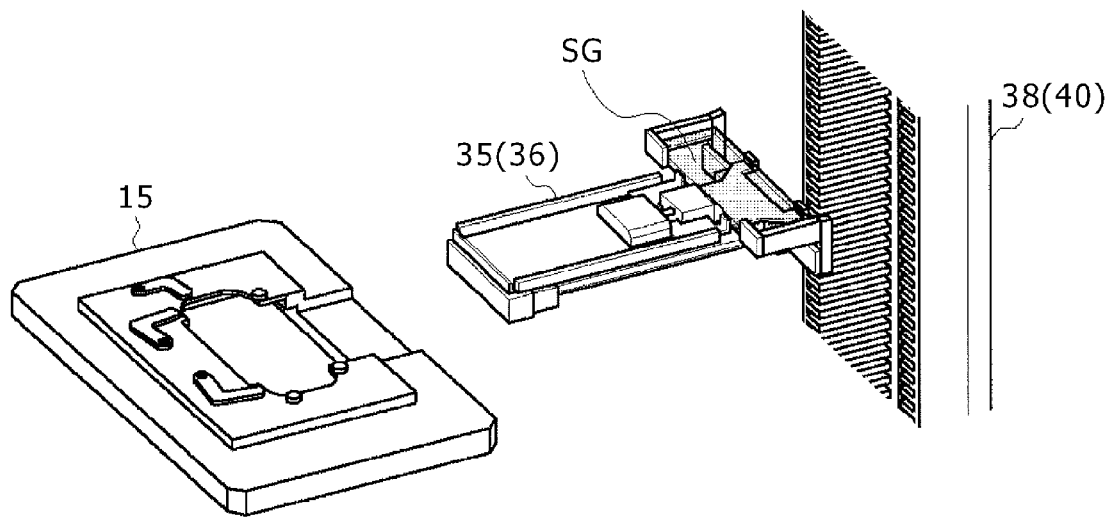

In this case, when the target slide glass SGT is not caught on the guide section 65B or 65C, the supply arm 35 contracts the arm movement section 70 completely, as shown in FIG. 18, thereby moving the target slide glass SGT into the holding space 65D.

On the other hand, when the target slide glass SGT is caught on the guide section 65B or 65C or the like, the supply arm 35 does not irrationally slide the arm movement section 70 but stops it at an intermediate position, in order to prevent the target slide glass SGT from being broken. In this case, the target slide glass SGT is not drawn into the holding space 65D.

In step SP14, the control unit 21 determines whether or not the arm movement section 70 of the supply arm 35 has successfully been contracted completely, based on the results of detection by the sensor 64.

When an affirmative determination is obtained in step SP14, it means that the target slide glass SGT has successfully been moved into the holding space 65D without being caught on the guide section 65B or 65C, in other words, that the length of the longer edge of the target slide glass SGT is not more than the longer edge upper limit. In this instance, in order to advance a conveying process of the target slide glass SGT, the control unit 21 proceeds to the next step SP15.

In step SP15, the control unit 21 controls the clamp motor 75 in the clamp unit 73 of the supply arm 35, to effect a pressing operation of moving the clamp block 76 in the +Q direction. By this, the control unit 21 causes the target slide glass SGT to be gripped between the projected section 76A of the clamp block 76 and the fixing claws 71BY, and proceeds to the next step SP16.

Incidentally, since the moving distance of the clamp block 76 in the clamp unit 73 is short, the gripping operation is completed in an extremely short time.

In this instance, the supply arm 35 can detect the grip spacing (grip interval), based on the functions of the sensors 78A and 78B in the clamp unit 73.

In step SP16, the control unit 21 determines whether or not the grip interval thus detected is within the shorter edge allowable range. When an affirmative determination is obtained here, it means that both the longer edge and the shorter edge of the target slide glass SGT being gripped are within the respective allowable ranges, in other words, that the target slide glass SGT can be properly disposed on the stage 15. In this instance, the control unit 21 proceeds to the next step SP20.

On the other hand, when a negative determination is obtained in step SP14, it means that the target slide glass SGT has not successfully been moved into the holding space 65D but has been caught on the guide section 65B or 65C, because the target slide glass SGT exceeds the longer edge upper limit or because of other reason. In this instance, the control unit 21 determines that the target slide glass SGT in question at present cannot be gripped and therefore cannot be conveyed onto the stage 15. Then, the control unit 21 proceeds to the next step SP17.

In step SP17, the control unit 21 controls the translation section 63 of the supply arm 35 so as to effect an extending operation of sliding the arm movement section 70 (FIG. 11) in the +Q direction, and proceeds to the next step SP18.

In this instance, the target slide glass SGT is in the state of being mounted on the mount surface 71BX in an original storage site in the storage unit 38, specifically, in the state of being lifted up from the slit sections of the multi-sheet cassette 40.

In step SP18, the control unit 21 moves the carriage 34 downward to thereby lower the supply arm 35, and proceeds to the next step SP20.

In this case, the target slide glass SGT is returned into a state in which both its end portions in regard of the longitudinal direction are supported by the slit portions of the multi-sheet cassette 40, in other words, into the same state as before the start of the pick-up operation.

On the other hand, when a negative determination is obtained in step SP16, it means that the length of the shorter edge of the target slide glass SGT falls outside of the allowable range and that the target slide glass SGT cannot be properly fixed onto the stage 15. In this instance, the control unit 21 determines that the target slide glass SGT should not be conveyed onto the stage 15, and proceeds to the next step SP19.

In step SP19, the control unit 21 controls the clamp motor 75 in the clamp unit 73, so as to effect a releasing operation of moving the clamp block 76 in the
−Q direction, and proceeds to the next step SP17.

In this case, the target slide glass SGT is in the state of not being gripped by the gripping unit 70A, in other words, in the state of being mounted on the mount surface 71BX.

Thereafter, like in the case where the negative determination is obtained in step SP14, the control unit 21 executes the processes of steps SP17 and SP18, to thereby return the target slide glass SGT into the same state as before the start of the pick-up operation, and proceeds to the next step SP20.

In step SP20, the control unit 21 transfers to the routine RT1 the determination data representing whether or not the target slide glass SGT has successfully been gripped normally, finishes the sub-routine SRT1, then returns to step SP2 in the original routine RT1 (FIG. 14), and proceeds to the next step SP3.

In step SP3, the control unit 21 determines whether or not the target slide glass SGT has successfully be gripped normally, based on the determination data brought from the sub-routine SRT1. When an affirmative determination is obtained here, it means that the conveying operation for the target slide glass SGT of concern at present should be continued. In this instance, the control unit 21 proceeds to the next step SP4.

Figure 19:
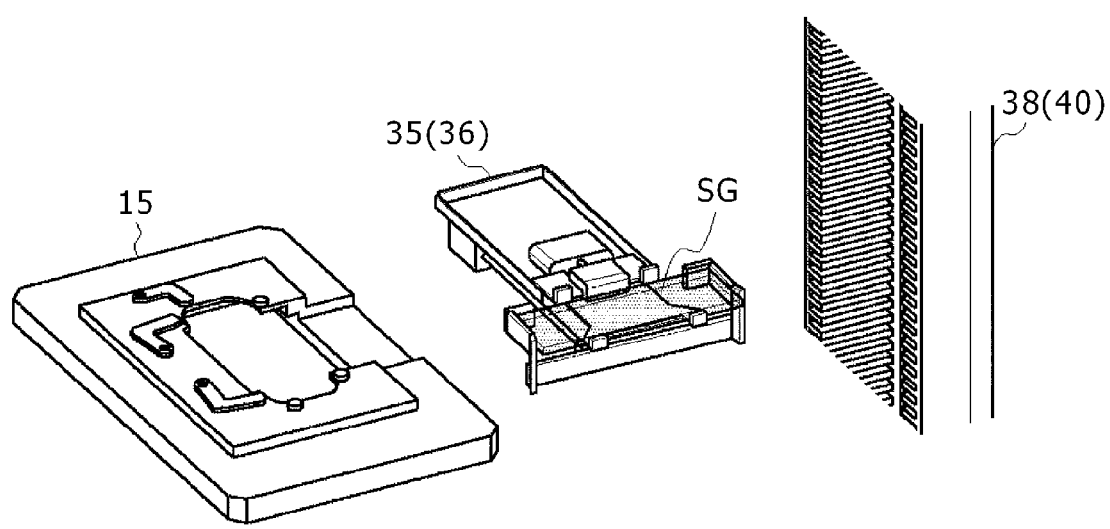

In step SP4, the control unit 21 controls the rotating base 32 so as to slew the supply arm 35 into a direction for facing the stage 15 (hereafter, this direction will be referred to as the stage direction), as shown in FIG. 19, and proceeds to the next step SP5.

In this instance, forces in various directions arising from actions of a centrifugal force and a moment of inertia attendant on the rotating motion, etc. are exerted on the slide glass SG. However, the supply arm 35 continues holding the target slide glass SGT in the holding space 65D, without dropping it, by the functions of the guide sections 65B and 65C as well as the fixing claws 71BY and the projected section 76A of the clamp block 76.

In step SP5, the control unit 21 controls of the carriage 34 so as to adjust the height of the supply arm 35 to the stage 15, and proceeds to the next step SP6.

Figure 20:
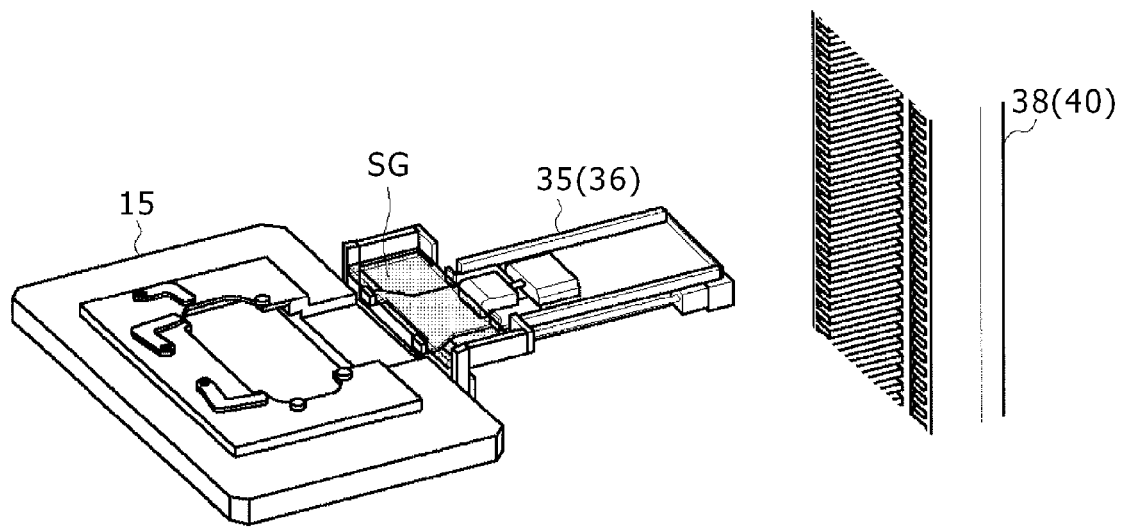

Incidentally, as shown in FIG. 20, the control unit 21 in this instance controls the height of the supply arm 35 so that the mount surface 71BX of the supply arm 35 is slightly higher than the upper surface of the stage 15.

In step SP6, the control unit 21 proceeds to sub-routine SRT2 (FIG. 16) in order to perform a releasing operation process by the supply arm 35, and enters step SP31.

Figure 21:
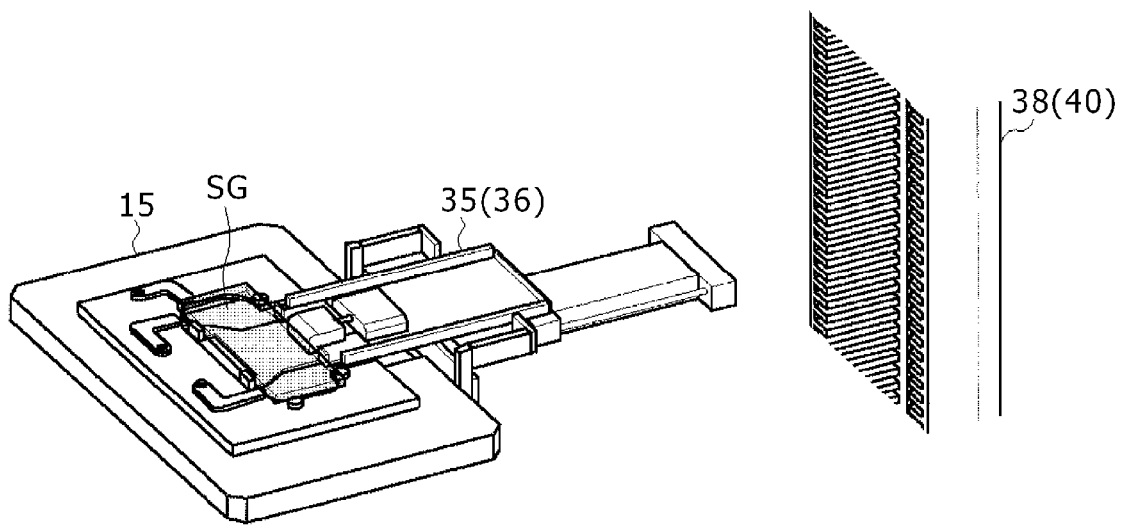

In step SP31, the control unit 21 controls the translation section 63 of the supply arm 35, so as to effect an extending operation of sliding the arm movement section 70 (FIG. 11) in the +Q direction, as shown in FIG. 21, and then proceeds to the next step SP32.

In this instance, the target slide glass SGT is located at a position substantially just above that position on the stage 15 at which the slide glass is to be mounted.

In step SP32, the control unit 21 controls the clamp motor 75 in the clamp unit 73 so as to perform a releasing operation of moving the clamp block 76 in the
−Q direction, and proceeds to the next step SP33.

In this instance, the target slide glass SGT is in the state of not being gripped by the gripping unit 70A, in other words, in the state of being mounted on the mount surface 71BX without being not fixed in any way.

In step SP33, the control unit 21 causes the carriage 34 to move downward so as to lower the supply arm 35, and then proceeds to the next step SP34.

In this instance, the target slide glass SGT is in a state wherein its central portion is supported by the mount surface 71BX of the supply arm 35 and both its end portions in regard of the longitudinal direction are supported by the stage 15.

In step SP34, the control unit 21 operates the clip members on the stage 15 to perform a fixing process of fixing the slide glass SG, and then proceeds to the next step SP35.

In step SP35, the control unit 21 causes the carriage 34 to move downward so as to lower the supply arm 35, and proceeds to the next step SP36.

In this instance, the supply arm 35 is put into a state wherein the mount surface 71BX is spaced from the target slide glass SGT fixed on the stage 15 and, further, upper end portions of the fixing claws 71BY are located below the lower surface of the target slide glass SGT.

In step SP36, the control unit 21 controls the translation section 63 of the supply arm 35 so as to perform a contracting operation, and proceeds to the next step SP37.

In this instance, the supply arm 35 finishes releasing the slide glass SG, thereby coming into so to speak an empty state.

In step SP37, the control unit 21 finishes the sub-routine SRT2, returns to step SP6 in the original routine RT1 (FIG. 14), and proceeds to the next step SP7. In step SP7, the control unit 21 finishes routine RT1, thereby completing the basic conveying operation of the supply arm 35.

On the other hand, when a negative determination is obtained in step SP3, it means that a conveying operation for the target slide glass SGT of concern at present cannot be continued. In this instance, the control unit 21 proceeds to step SP7, thereby to complete routine RT1.

Thus, in its basic conveying operation, the supply arm 35 is so controlled that it is detected whether or not the lengths of the longer edge and the shorter edge of the slide glass SG are within the respective allowable ranges, and performs the conveying operation only in the case where the lengths are within the allowable ranges.

Incidentally, the control unit 21 of the controlling unit 4 is so designed as to perform a similar conveying operation also in the case where a supply tray 52 of a one-sheet tray 50 provided as a storage unit 38 is used as a storage site.

1-6-3. Configuration of Discharge Arm

The discharge arm 36 (FIG. 11) is similar to the supply arm 35 in configuration, and has an arm fixation section 80 and an arm movement section 90 which correspond to the arm fixation section 60 and the arm movement section 70, respectively.

The arm fixation section 80 is configured in the same manner as the arm fixation section 60 of the supply arm 35, except for having a fall-off preventive guide 85 corresponding to the fall-off preventive guide 65.

The fall-off preventive guide 85 includes a flat plate section 85A and guide sections 85B and 85C corresponding respectively to the flat plate section 65A and the guide sections 65B and 65C of the fall-off preventive guide 65.

The flat plate section 85A is greater than the flat plate section 65A in length in the P-axis direction. The guide sections 85B and 85C are greater than the guide sections 65B and 65C in inclination angle, from the Q-axis direction toward the P-axis direction, of coupling plates 85B1 and 85C1 which correspond respectively to the coupling plates 65B1 and 65C1.

This ensures that, when the arm fixation section 80 is compared with the arm fixation section 60, a holding space 85D defined by the guide sections 85B and 85C is larger than the holding space 65D. In other words, the holding space 85D has a length in the Q-axis direction and a length in the P-axis direction which are greater than the longer edge upper limit and the shorter edge upper limit for the slide glass SG.

In addition, the arm movement section 90 is configured in the same manner as the arm movement section 70 of the supply arm 35, except for having a clamp unit 93 in place of the clamp unit 73 (FIG. 12A).

The clamp unit 93 is configured in the same manner as the clamp unit 73, except for having a mounting plate 94 in place of the mounting plate 74.

The mounting plate 94 has a structure in which the length in the Q-axis direction is reduced and the movable range of a clamp block 76 is enlarged in the –Q direction, as compared with the mounting plate 74. Consequently, in the arm movement section 90, the spacing from fixing claws 71BY to a projected section 76A of the clamp block 76 in a gripping unit 90A is enlarged, as compared with that in the arm movement section 70.

Consequently, in the clamp unit 93, the time required for a moving operation of the clamp block 76 is longer than that in the clamp unit 73.

Thus, the discharge arm 36 can perform an extending operation and a contracting operation in the same manner as the supply arm 35. In addition, the discharge arm 36 has the holding space 85D greater than the holding space 65D in the supply arm 35. Further, the moving range of the clamp block 76 in the clamp unit 93 of the discharge arm 36 is broadened, as compared with that in the supply arm 35.

1-6-4. Basic Conveying Operation of Discharge Arm

Figure 22:
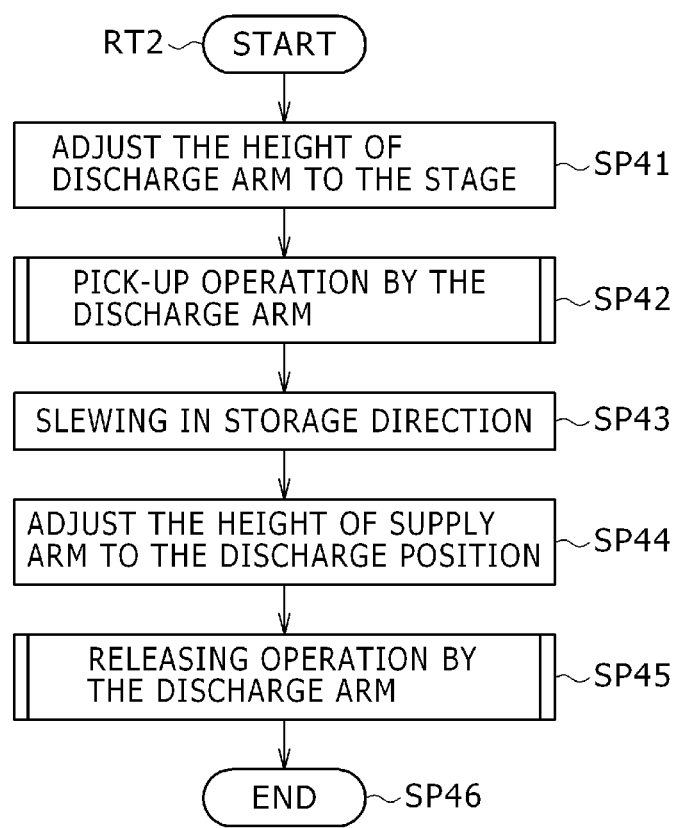
FIG. 22 is a flow chart showing the procedure of a basic conveying operation process of a discharge arm.
Figure 23:
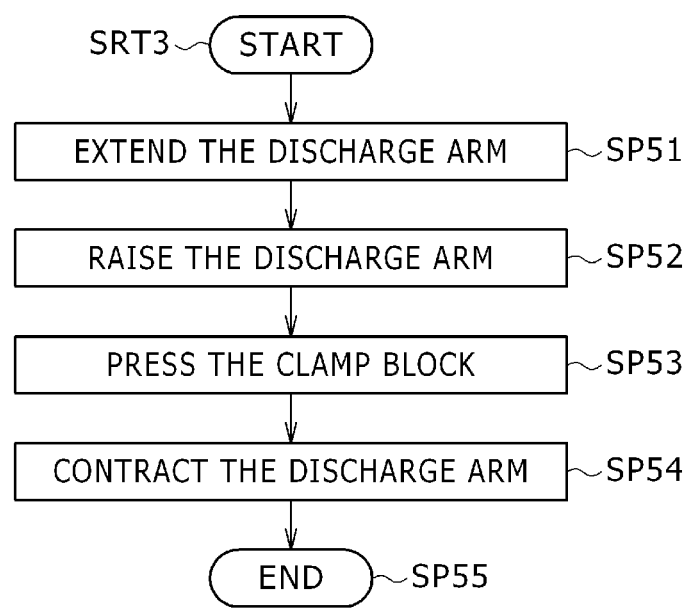
FIG. 23 is a flow chart showing the procedure of a pick-up operation process by the discharge arm.
Figure 24:
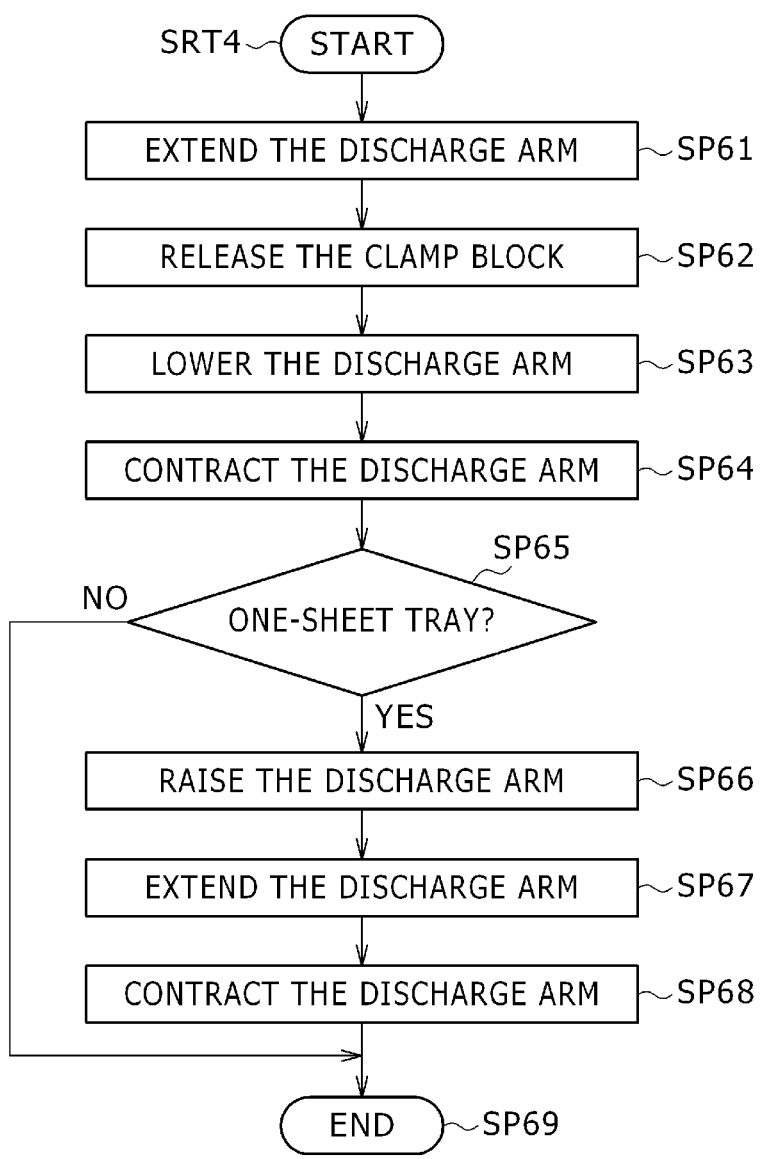
FIG. 24 is a flow chart showing the procedure of a releasing operation process by the discharge arm.

In practice, the controlling unit 4 (FIG. 2) executes a control according to the flow charts shown in FIGS. 22 to 24, in the case of conveying a slide glass SG by the discharge arm 36. The flow charts in FIGS. 22 to 24 basically correspond to the flow charts in FIGS. 14 to 16, respectively, but the procedures of processing in both cases are partly different.

Incidentally, here, description will be made by taking as an example the case of conveying a slide glass SG (target slide glass SGT) mounted on the stage 15 into the storage unit 38 having the multi-sheet cassette 40.

For example, upon receiving a starting instruction for a conveying operation by the discharge arm 36 through the operating unit 24, the control unit 21 of the controlling unit 4 starts routine RT2 and proceeds to step SP41.

In step SP41, the control unit 21 causes the carriage 34 to move in the vertical direction so as to adjust the height of the discharge arm 36 to the height of the stage 15 on which the target slide glass SGT is mounted, and proceeds to the next step SP42.

In this instance, the height of the discharge arm 36 is so adjusted that upper end portions of the fixing claws 71BY (FIG. 11) are set slightly below the lower surface of the target slide glass SGT.

In step SP42, the control unit 21 proceeds to a sub-routine SRT3 (FIG. 23) in order to perform a pick-up operation process by the discharge arm 36, and enters step SP51.

Incidentally, the sub-routine SRT3 shows a procedure of process as if derived from the sub-routine SRT1 (FIG. 15), which represents the procedure of the pick-up operation process by the supply arm 35, by omitting the determination process and the process of returning the target slide glass SGT into an original position.

Specifically, in step SP51, the control unit 21 controls the translation section 63 of a discharge arm 36 so as to perform an extending operation of sliding the arm movement section 90 (FIG. 11) in the +Q direction, and then proceeds to the next step SP52.

In this instance, the mount surface 71BX of the arm movement section 90 is located substantially just under the target slide glass SGT.

In step SP52, the control unit 21 causes the carriage 34 to move upward so as to raise the discharge arm 36, and proceeds to the next step SP53.

In this instance, the discharge arm 36 mounts the target slide glass SGT onto the mount surface 71BX, and lifts up both end portions in regard of the longitudinal direction of the target slide glass SGT from the stage 15.

In step SP53, the control unit 21 controls the translation section 63 of the discharge arm 36 to perform a contracting operation, and proceeds to step SP54.

In this instance, as shown in FIG. 21, the discharge arm 36 contracts the arm movement section 90 completely, to move the target slide glass SGT into the holding space 85D.

Incidentally, as above-mentioned, the discharge arm 36 has a structure wherein the length in the Q-axis direction and the length in the P-axis direction of the holding space 85D are set to be greater than the longer edge upper limit and the shorter edge upper limit for the slide glass SG, respectively. Therefore, even if the target slide glass SGT is inclined on the mount surface 71BX or is positionally deviated in the P-axis direction, the discharge arm 36 can picks up the target slide glass SGT into the holding space 85D.

In step SP54, the control unit 21 controls the clamp motor 75 in the clamp unit 93 of the discharge arm 36 so as to perform a pressing operation of moving the clamp block 76 in the +Q direction. By this, the control unit 21 causes the target slide glass SGT to be gripped between the projected section 76A of the clamp block 76 and the fixing claws 71BY, and proceeds to the next step SP55.

Incidentally, as above-mentioned, in the discharge arm 36, the moving range of the clamp block 76 in the clamp unit 93 is enlarged as compared with that in the clamp unit 73 of the supply arm 35. Therefore, even if the target slide glass SGT is inclined on the mount surface 71BX, the discharge arm 36 can appropriately grip the target slide glass SGT while correcting the inclination.

In step SP55, the control unit 21 finishes the sub-routine SRT3, returns to step SP42 in the original routine RT2 (FIG. 22), and then proceeds to the next step SP43.

In step SP43, the control unit 21 controls the rotating base 32 so as to slew the discharge arm 36 into a direction for facing the multi-sheet cassette 40 provided as the storage unit 38 (hereafter, this direction will be referred to as the storage direction), as shown in FIG. 19, and proceeds to the next step SP44.

In step SP44, the control unit 21 controls the carriage 34 so as to adjust the height of the discharge arm 36 to that slot in the multi-sheet cassette 40 in which to store the target slide glass SGT (hereafter, this place will be referred to as the discharge site), and proceeds to the next step SP45.

In step SP45, the control unit 21 proceeds to a sub-routine SRT4 (FIG. 24) in order to perform a releasing operation process by the discharge arm 36, and enters step SP61.

Incidentally, the sub-routine SRT4 shows a procedure of process as if derived from the sub-routine SRT2 (FIG. 16), representing the procedure of the releasing operation process by the supply arm 35, by omitting the step SP34 and uniting the process of step SP33 with the process of step SP35.

Specifically, in step SP61, the control unit 21 controls the translation section 63 of the discharge arm 36 so as to perform an extending operation of sliding the arm movement section 90 (FIG. 11) in the +Q direction, and then proceeds to step SP62.

In this instance, the target slide glass SGT is in the state of being gripped by the gripping unit 90A in the slot of the discharge site, as shown in FIG. 17.

In step SP62, like in step SP32, the control unit 21 controls the clamp motor 75 in the clamp unit 93 to perform a releasing operation of moving the clamp block 76 in the −Q direction, and proceeds to the next step SP63.

In this instance, the target slide glass SGT is in the state of not being gripped by the gripping unit 90A, in other words, in the state of being mounted on the mount surface 71BX without being fixed in any way.

In step SP63, the control unit 21 causes the carriage 34 to move downward so as to lower the discharge arm 36, and proceeds to the next step SP64.

In this instance, the target slide glass SGT is in a state wherein both its end portions in regard of the longitudinal direction are supported by the slit portions of the multi-sheet cassette 40 and it is spaced from the mount surface 71BX. In addition, the discharge arm 36 is in a state wherein upper end portions of the fixing claws 71BY are located below the lower surface of the target slide glass SGT.

In step SP64, the control unit 21 controls the translation section 63 of the discharge arm 36 so as to perform a contracting operation, and proceeds to the next step SP65.

In step SP65, the control unit 21 determines whether or not the discharge site at present is the discharge tray 53 of the one-sheet tray 50. In this case, the discharge site is a slot in the multi-sheet cassette 40; therefore, the control unit 21 obtains a negative determination, and proceeds to step SP69.

In step SP69, the control unit 21 finishes the sub-routine SRT4, returns to step SP45 in the original routine RT2 (FIG. 22), and proceeds to the next step SP46. In step SP46, the control unit 21 finishes the routine RT2, thereby finishing the basic conveying operation of the discharge arm 36.

Meanwhile, in the microscope system 1, in the case where the one-sheet tray 50 (FIG. 6) is used in place of the multi-sheet cassette 40 as the storage unit 38, the releasing operation for the slide glass SG can be carried out by using the discharge tray 53 as the discharge site.

In this instance, upon completion of step SP64 in the sub-routine SRT4, the control unit 21 causes the target slide glass SGT to be released into the holding space 53D, while supporting the target slide glass SGT by the inside bottom surfaces 53C1 and 53C2 of the discharge tray 53 (FIG. 9).

Further, upon obtaining an affirmative determination in step SP65, the control unit 21 proceeds to step SP66. In step SP66, the control unit 21 causes the carriage 34 to move upward so as to raise the discharge arm 36, and proceeds to the next step SP67.

In this instance, the discharge arm 36 adjusts the height of +Q-side surface portions of the fixing claws 71BY to the height of a side surface portion of the target slide glass SGT.

In step SP67, the control unit 21 controls the translation section 63 of the discharge arm 36 so as to perform an extending operation of sliding the arm movement section 90 (FIG. 11) by a predetermined distance in the +Q direction, and then proceeds to the next step SP68.

In this instance, the discharge arm 36 extends the arm movement section 90 to such an extent as to bring the fixing claws 71BY to a substantially central area of the holding space 53D, thereby bringing +Q-side surface portions of the fixing claws 71BY into contact with a side surface portion of the target slide glass SGT, and moves it in the manner of pushing it directly toward the discharge surface 53S2 side.

Consequently, a part of the target slide glass SGT is exposed from the hole 53G, as has been shown in FIG. 9C. Incidentally, the amount of exposure of the target slide glass SGT is set to such an extent that the operator can hold (pinch) the target slide glass SGT by fingers and that the target slide glass SGT would not fall off.

In step SP68, the control unit 21 performs a process similar to that of step SP64 to contract the discharge arm 36, thereby drawing out the gripping unit 90A completely from the discharge tray 53, and then proceeds to the next step SP69.

In step SP69, the control unit 21 finishes the sub-routine SRT4, thereby finishing the releasing (discharging) operation into the discharge tray 53 by the discharge arm 36.

Thus, the control unit 21 is so designed as to perform a pushing-out process as expressed in steps SP66 to SP69 in the case where the discharge site is the discharge tray 53 of the one-sheet tray 50.

1-6-5. Conveying Operation by Supply Arm and Discharge Arm

Meanwhile, in the microscope system 1, in the case of performing a continuous image sensing process of continuously sensing the images of a plurality of slide glasses SG, the slide glass SG on the stage 15 has to be sequentially replaced by the conveying unit 3.

In this instance, in the microscope system 1, a combined conveying operation is carried out such that the above-mentioned basic conveying operation of the supply arm 35 and the above-mentioned basic conveying operation of the discharge arm 36 are made to proceed concurrently.

Figure 25:
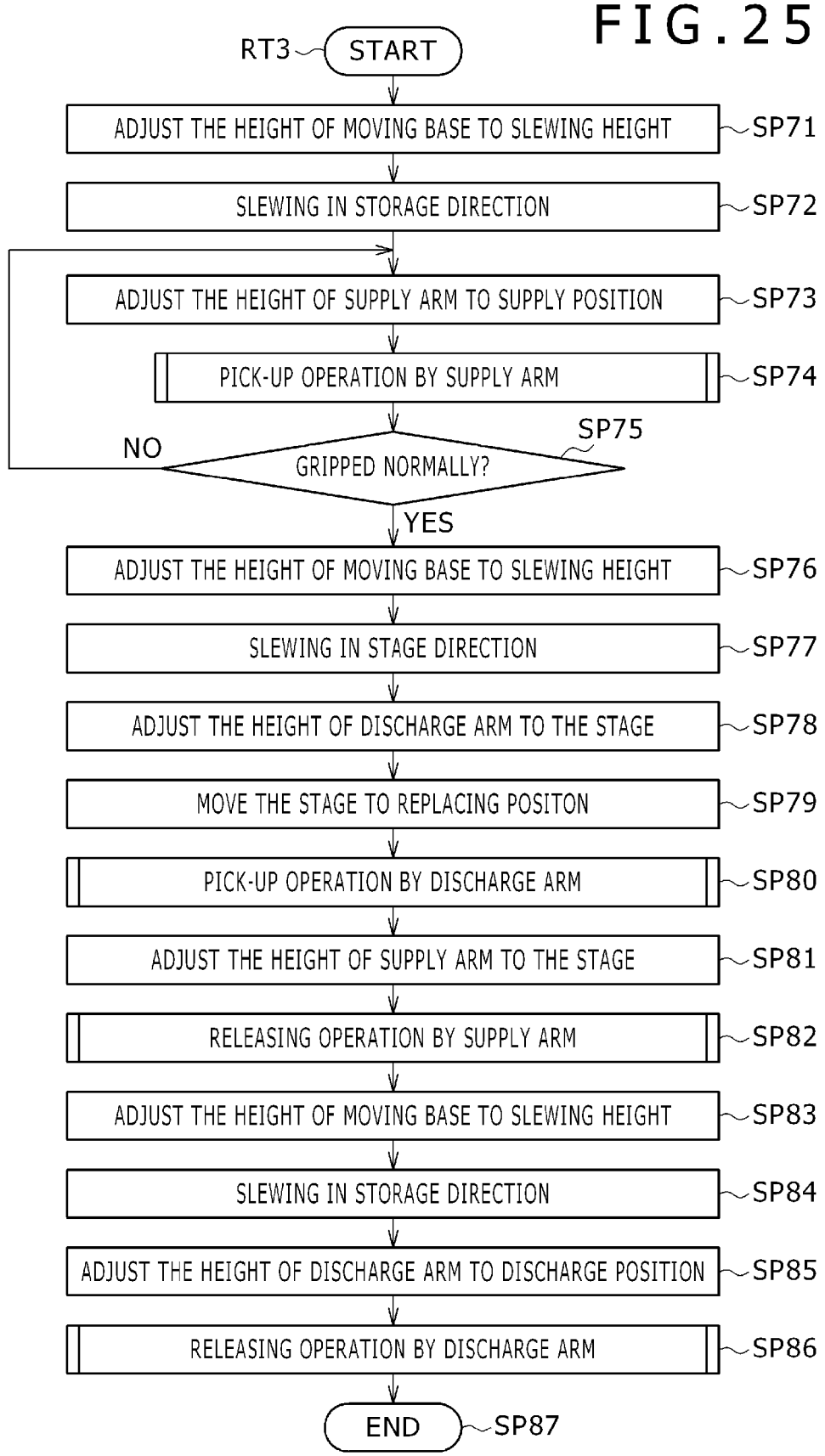
FIG. 25 is a flow chart showing the procedure of a conveying operation process by the supply arm and the discharge arm.

Here, the procedure of a conveying operation process conducted by use of the supply arm and the discharge arm will be described using the flow chart shown in FIG. 25 and the perspective views shown in FIGS. 26 to 46.

Figure 26:
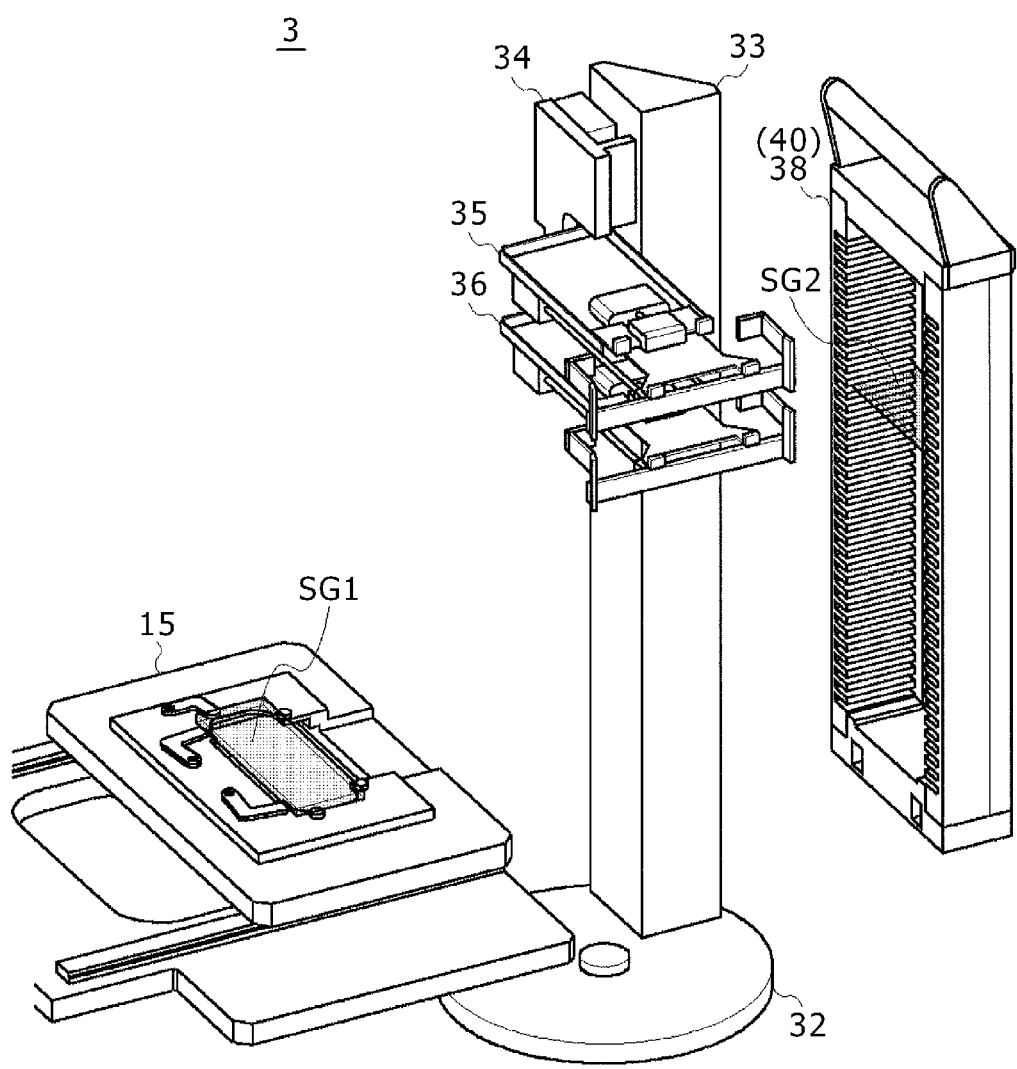
FIGS. 26 to 46 are diagrammatic perspective views showing conveying operations (1) to (21) by the supply arm and the discharge arm.
Figure 27:
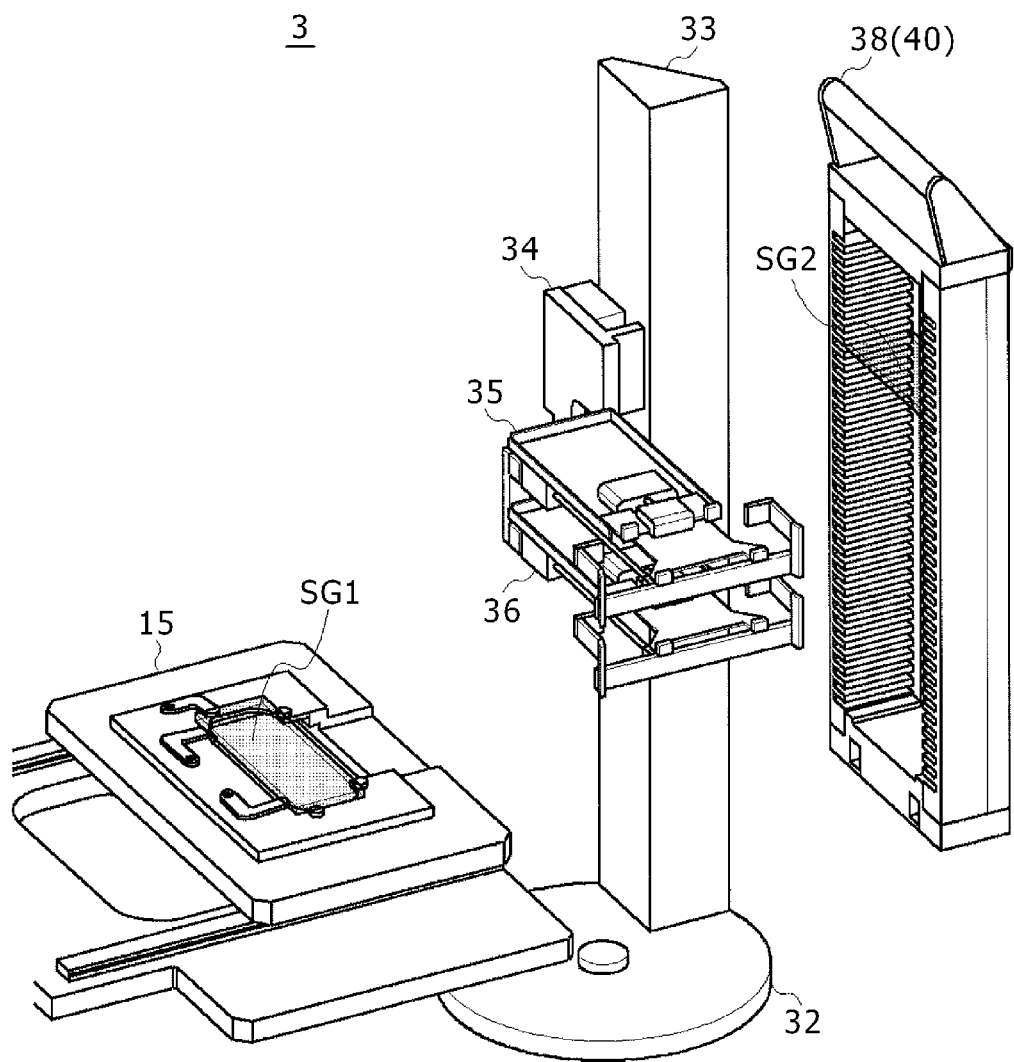

Incidentally, here, the slide glass SG to be subjected to image sensing (photography) first is referred to as slide glass SG1, and the slide glass SG to be subjected to image sensing (photography) next is referred to as slide glass SG2. The slide glass SG1 is assumed to have already been mounted on the stage 15, as shown in FIG. 26, and is being under an image sensing (photographing) treatment. In addition, the slide glass SG2 is assumed to be being stored in a predetermined slot in the multi-sheet cassette 40 provided as the storage unit 38 (hereafter, this slot will be referred to as the supply site).

Upon receiving a starting instruction for a continuous image sensing treatment through the operating unit 24, for example, the control unit 21 in the controlling unit 4 reads out a continuous image sensing program from the storage unit 23, and executes the program. In this instance, the control unit 21 carries out repeatedly a replacing process of replacing once the slide glass SG on the stage 15, according to the continuous image sensing program.

In the case of performing the replacing process, the control unit 21 reads out a predetermined replacing process program from the storage unit 23, to thereby start a routine RT3, and proceeds to step SP71.

In step SP71, the control unit 21 causes the carriage 34 to move in the vertical direction, so as to adjust the carriage 34 to a predetermined slewing height, and proceeds to the next step SP72.

Incidentally, the slewing height is preliminarily set as a height for obviating interference of the supply arm 35 and the like with other component parts of the microscope system 1 at the time of slewing the carriage 34, the supply arm 35 and the discharge arm 36 as one body by the rotating base 32.

In step SP72, the control unit 21 controls the rotating base 32 so as to slew the carriage 34, the supply arm 35 and the discharge arm 36 as one body into the storage direction, and then proceeds to the next step SP73.

Figure 28:
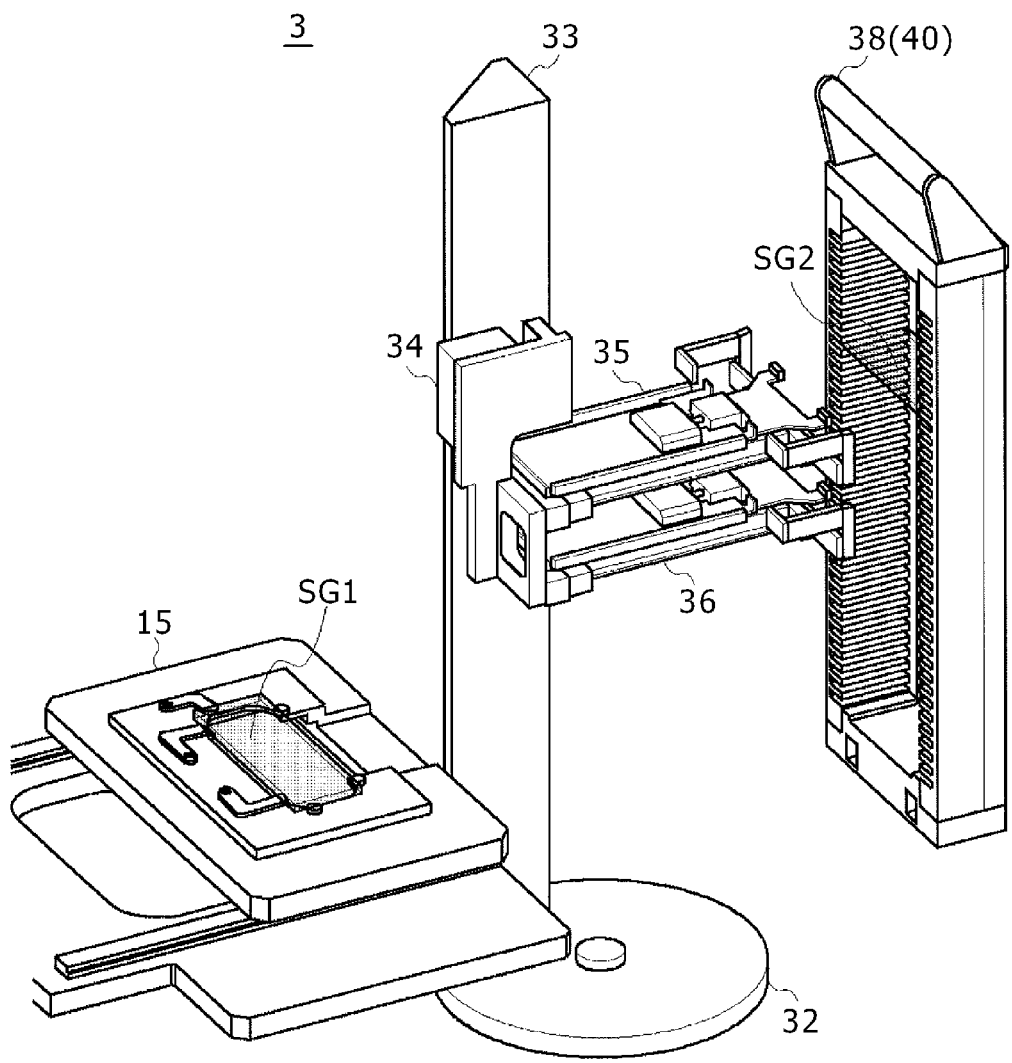

In step SP73, the control unit 21 causes the carriage 34 to move in the vertical direction, so as to adjust the supply arm 35 to the height of the supply site, as shown in FIG. 28, and proceeds to the next step SP74.

Figure 29:
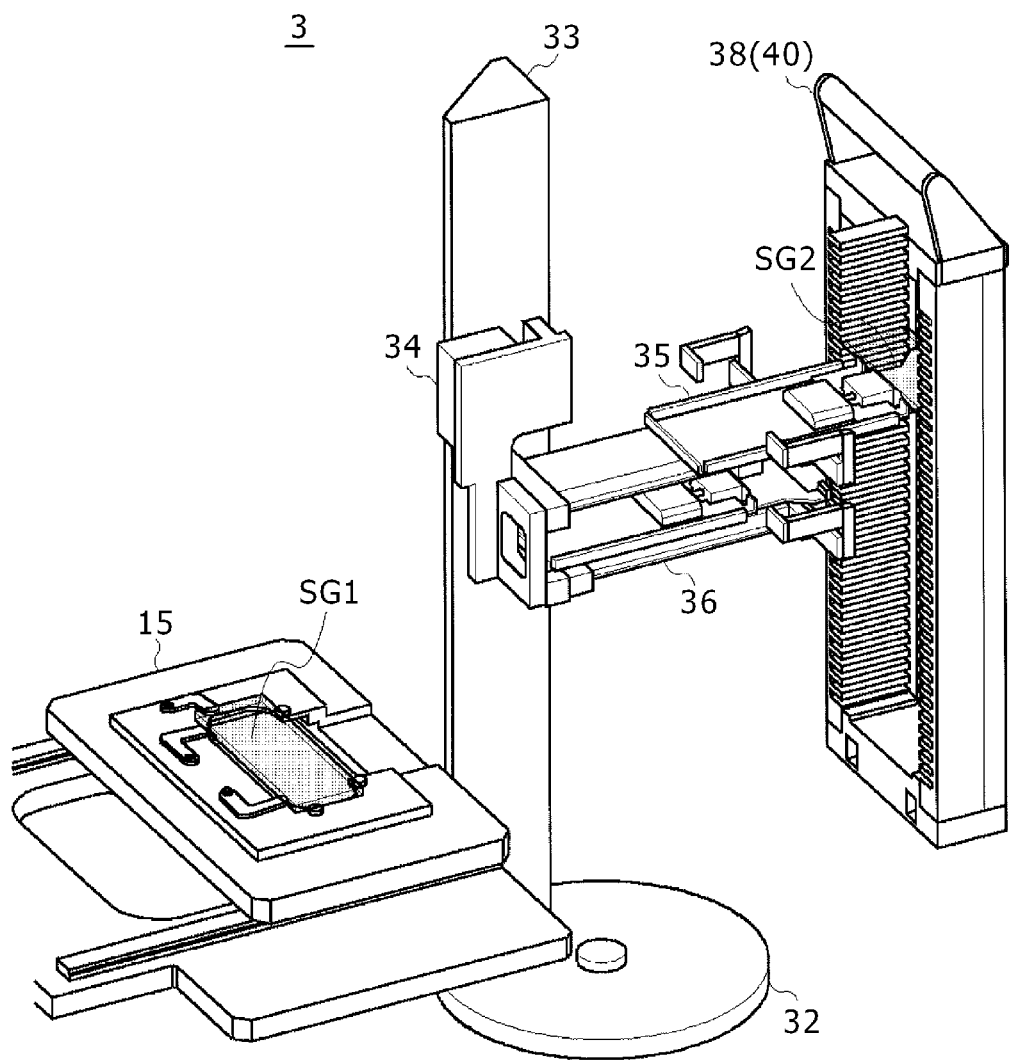
Figure 30:
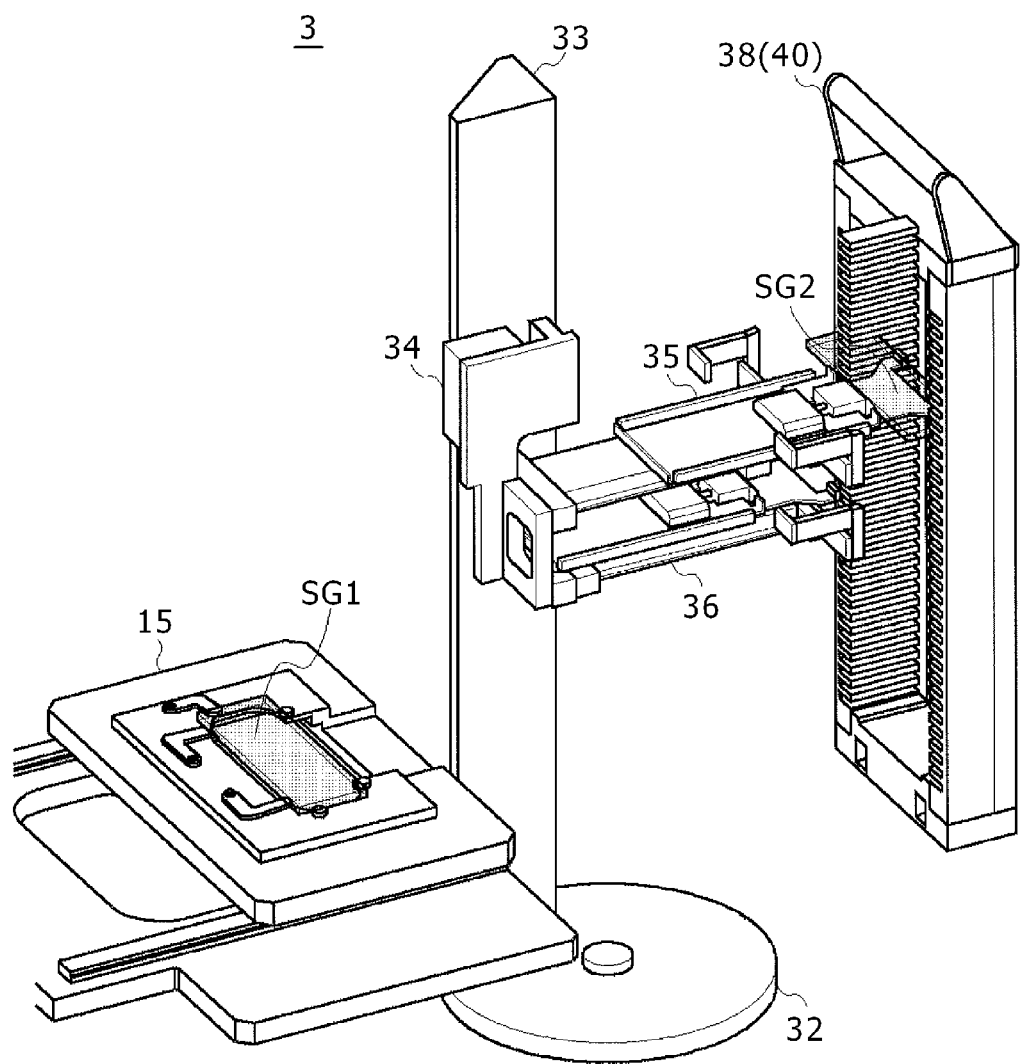

In step SP74, the control unit 21 carries out a series of pick-up operation process by the supply arm 35 as shown in the sub-routine SRT1 (FIG. 15). In this instance, the control unit 21 extends the supply arm 35 as shown in FIG. 29, then contracts the supply arm 35 with the slide glass SG2 mounted on the mount surface 71BX as shown in FIG. 30, and proceeds to the next step SP75.

In step SP75, the control unit 21 determines whether or not the slide glass SG2 has successfully been gripped normally, like in step SP3 of the routine RT1. When a negative determination is obtained here, it means that the lengths of the longer edge and the shorter edge of the slide glass SG2 fall outside of the allowable ranges, and that the slide glass SG2 should not or cannot be conveyed onto the stage 15. In this instance, the control unit 21 returns to step SP73, in order to try to pick up another slide glass SG.

Figure 31:
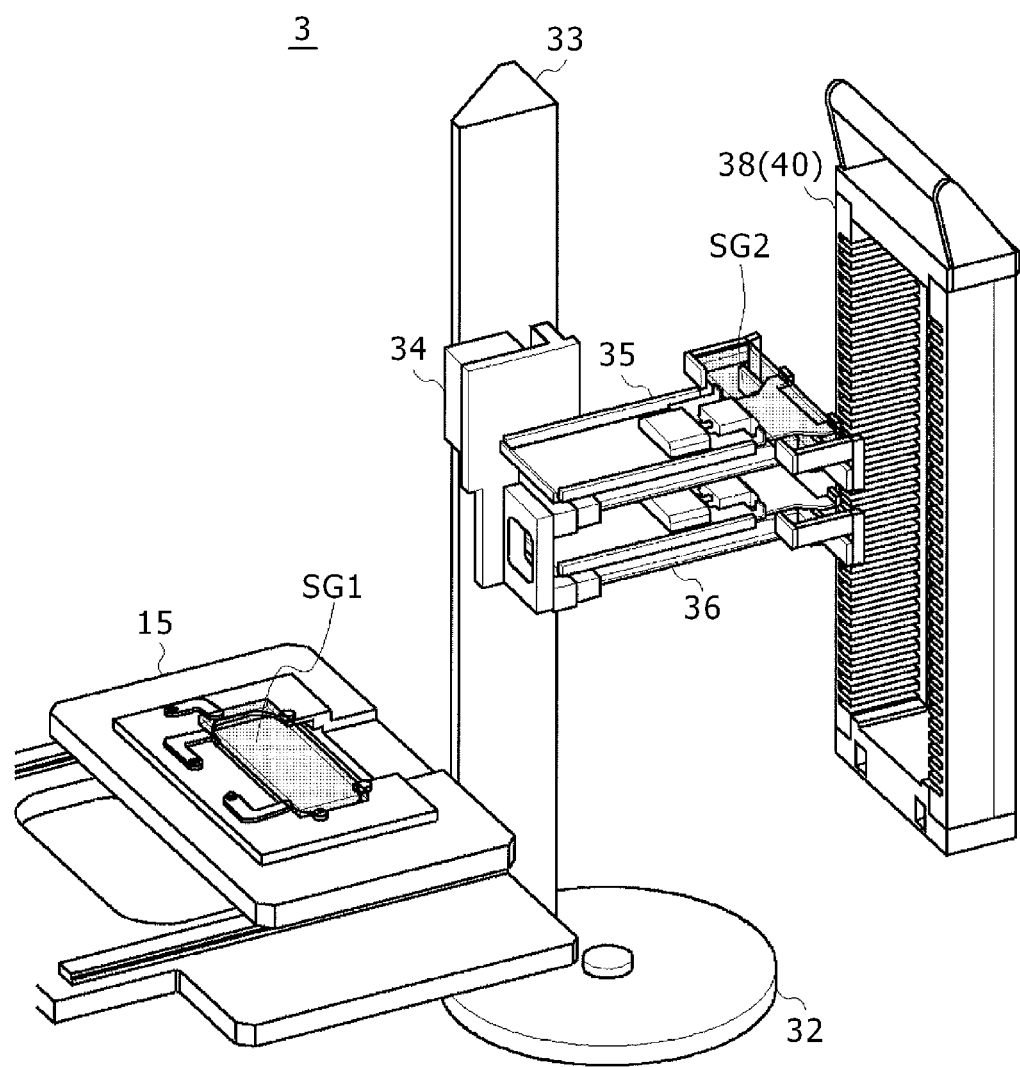

On the other hand, when an affirmative determination is obtained in step SP75, it means that the slide glass SG2 is properly gripped in the holding space 65D as shown in FIG. 31, in other words, the lengths of the longer edge and the shorter edge of the slide glass SG2 are within the allowable ranges. In this instance, the control unit 21 proceeds to the next step SP76, in order to convey the slide glass SG2 onto the stage 15.

Figure 32:
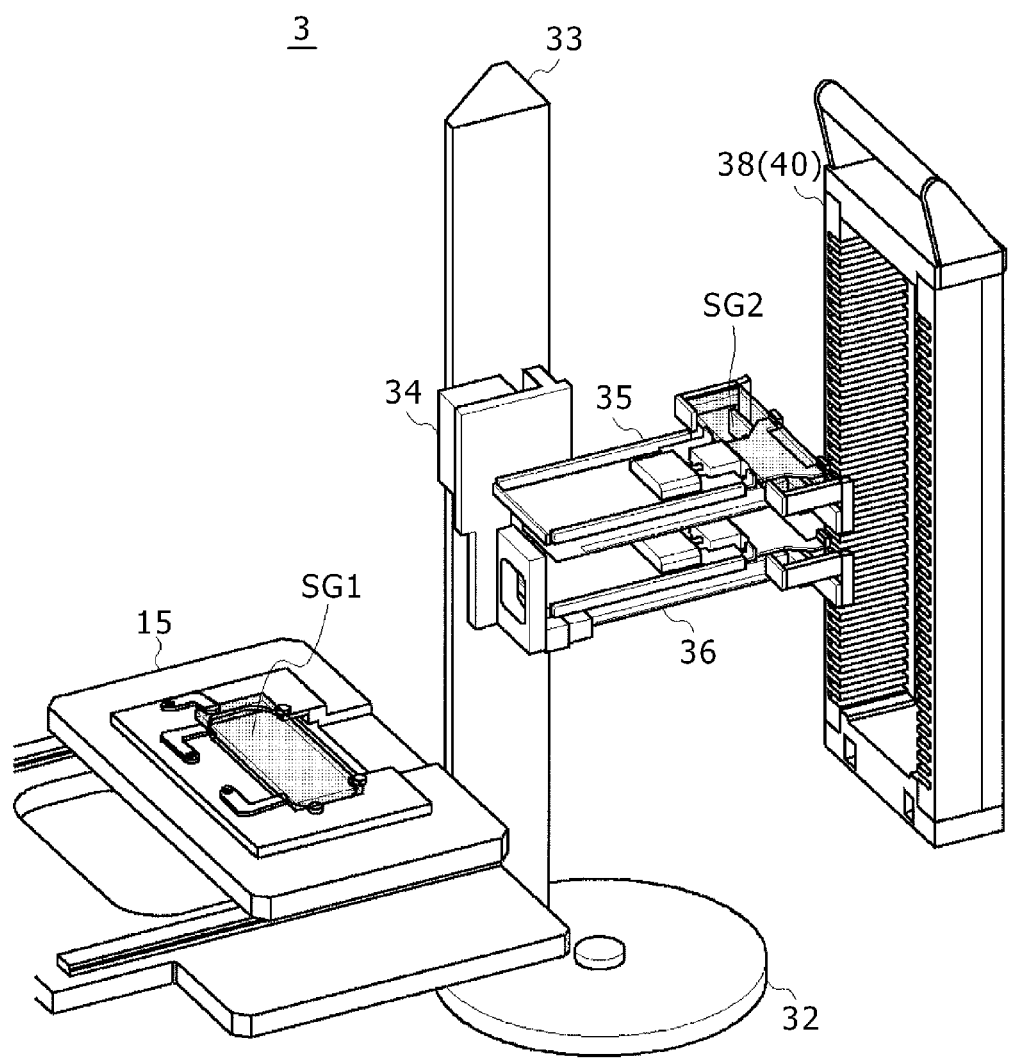

In step SP76, the control unit 21 causes the carriage 34 to move in the vertical direction, so as to adjust the carriage 34 to the slewing height, as shown in FIG. 32, and proceeds to the next step SP77.

Figure 33:
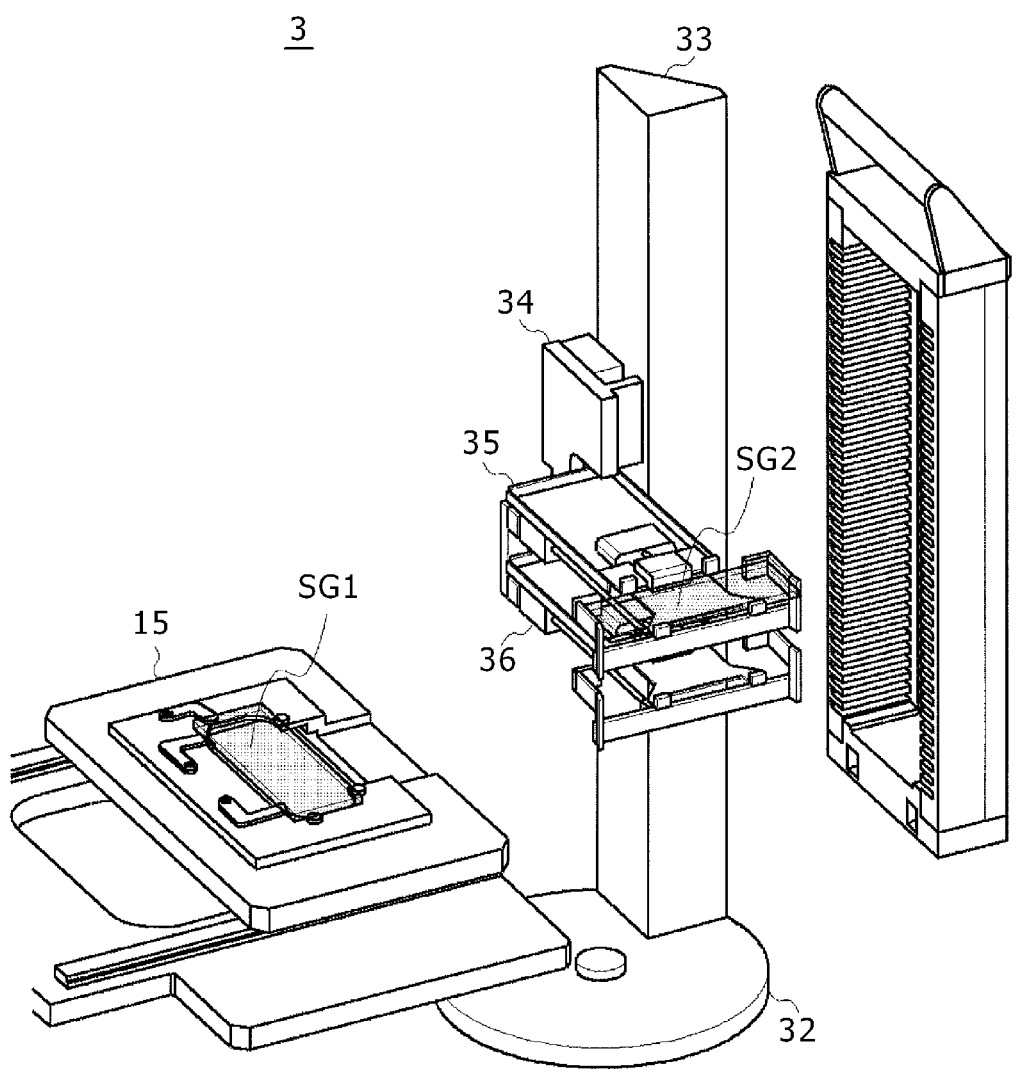
Figure 34:
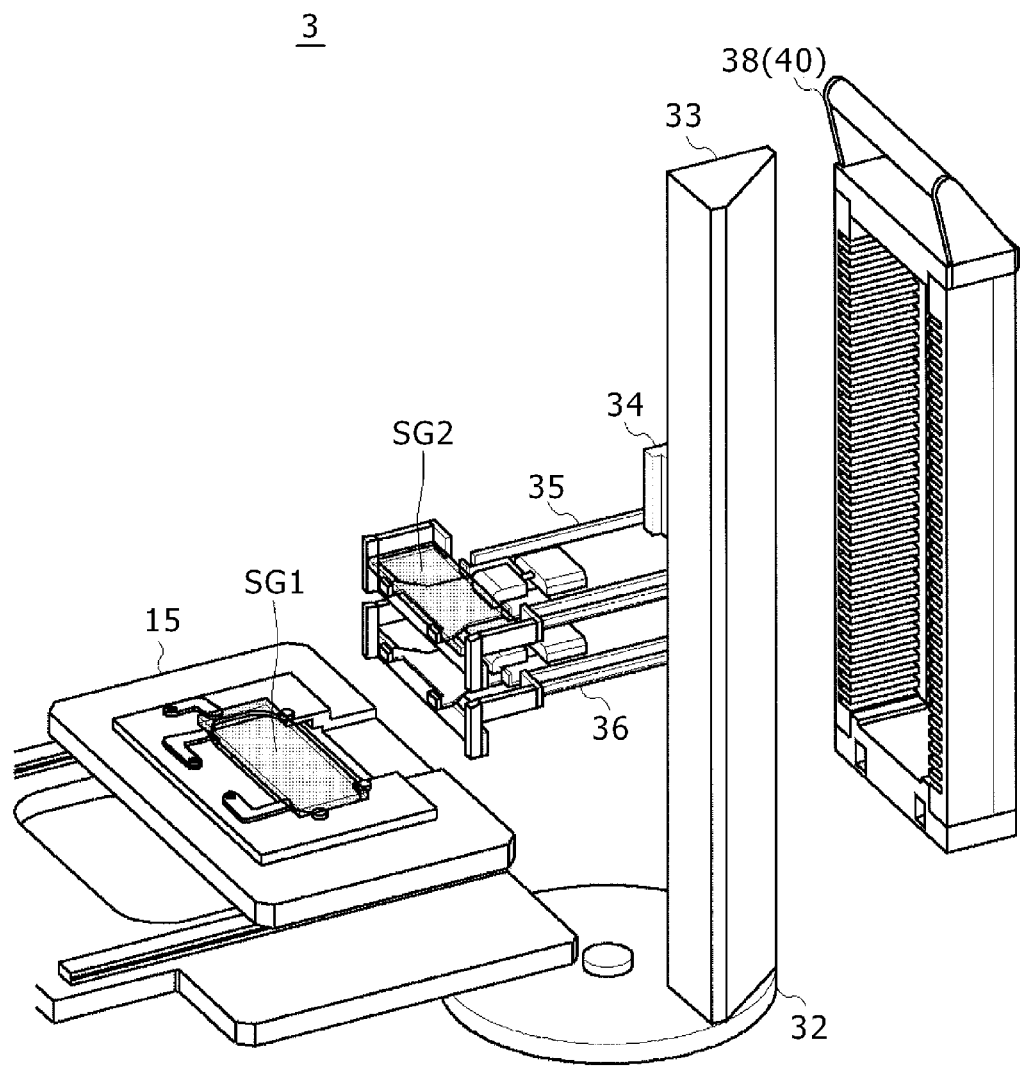

In step SP77, the control unit 21 controls the rotating base 32 so as to slew the supply arm 35 into the stage direction together with the carriage 34 and the discharge arm 36, as shown in FIGS. 33 and 34, and proceeds to the next step SP78.

Figure 35:
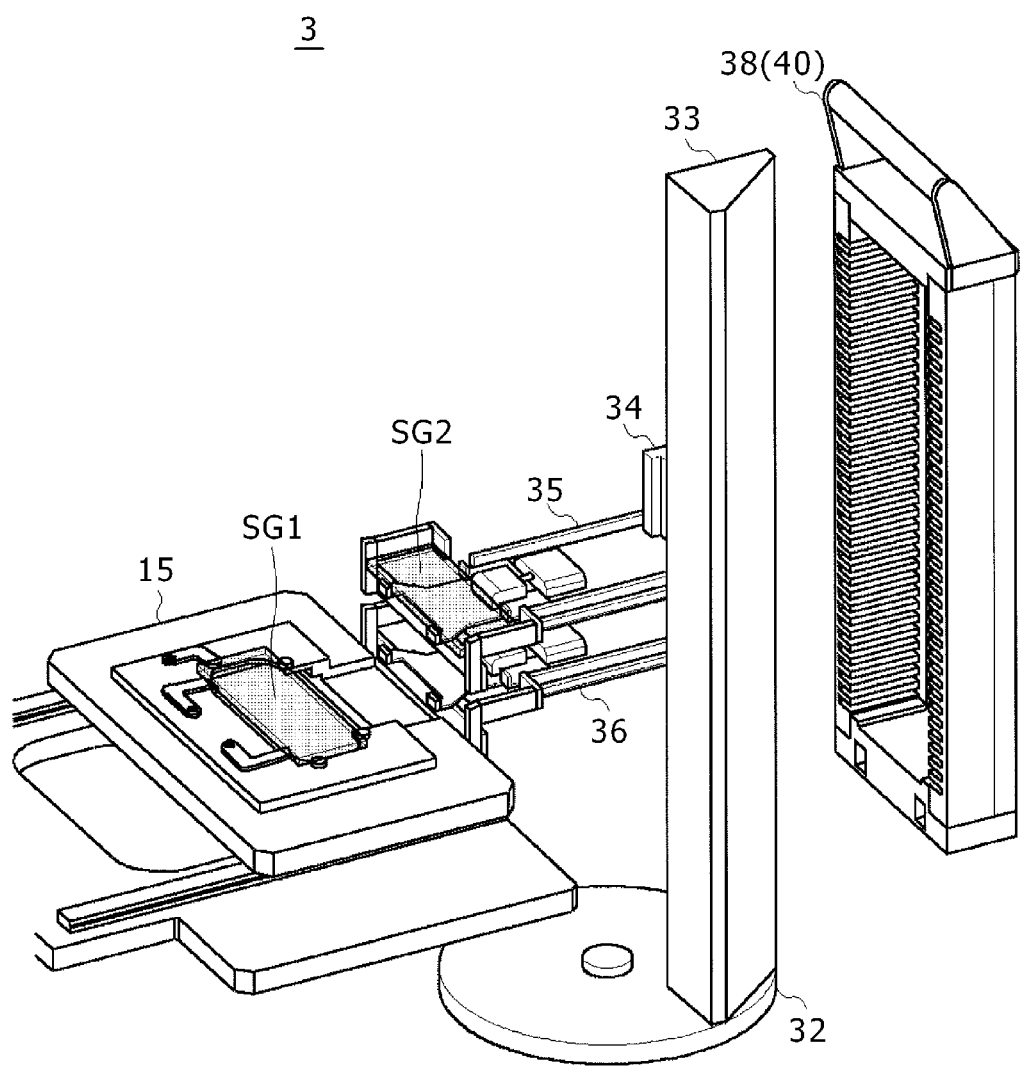

In step SP78, the control unit 21 causes the carriage 34 to move in the vertical direction so as to adjust the discharge arm 36 to the height of the stage 15, as shown in FIG. 35, and proceeds to the next step SP79.

In step SP79, the control unit 21, upon completion of the image sensing treatment of the slide glass SG1, moves the stage 15 to a predetermined replacement position as shown in FIG. 35, and proceeds to the next step SP80.

Figure 36:
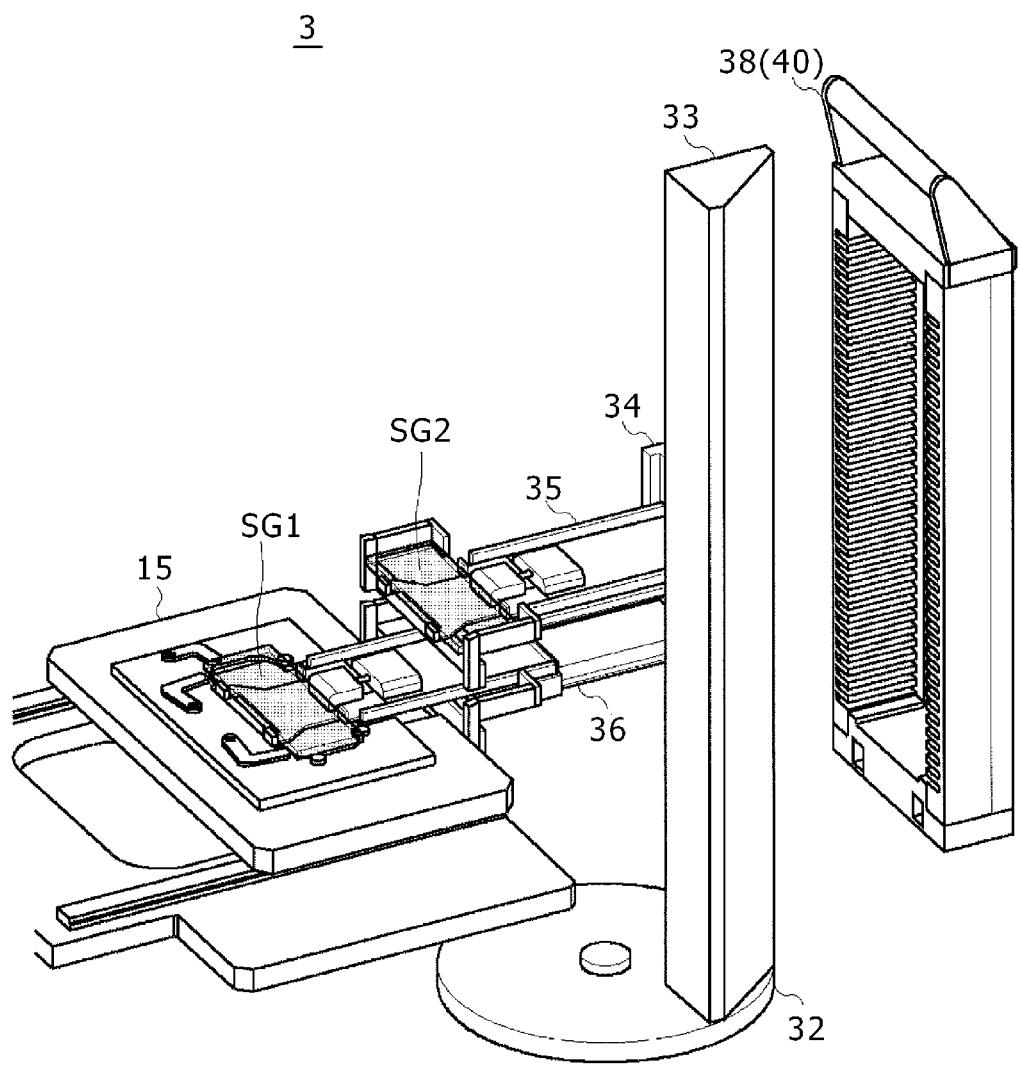
Figure 37:
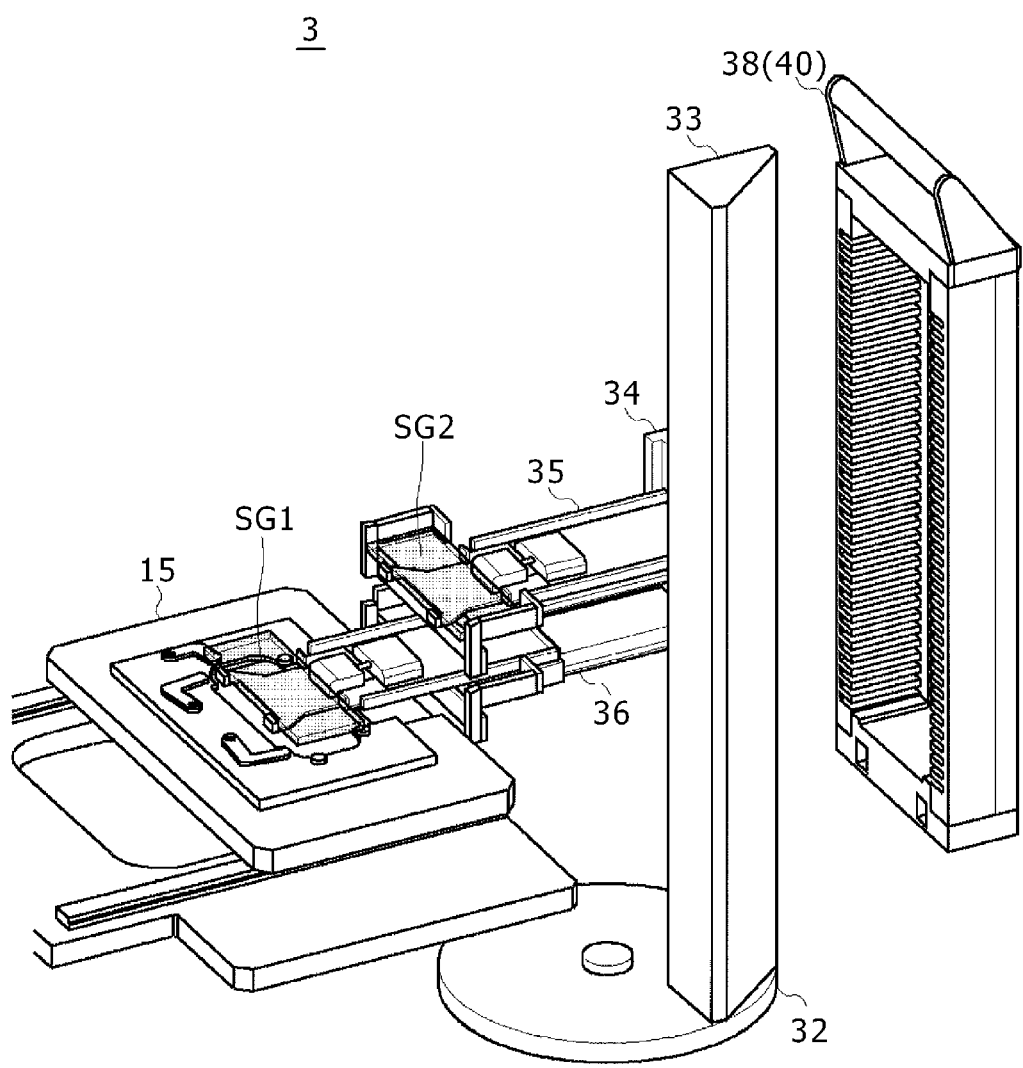
Figure 38:
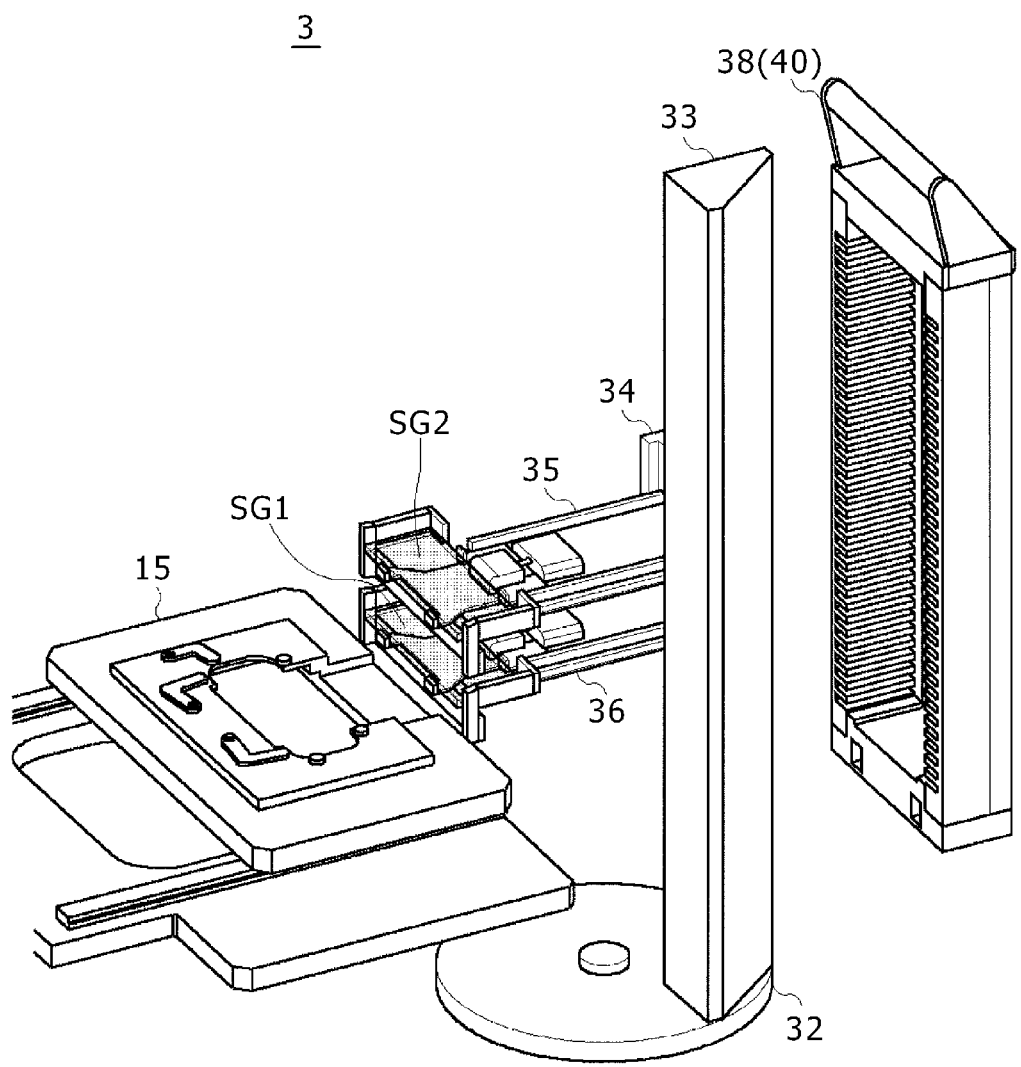

In step SP80, the control unit 21 carries out a series of pick-up operation process by the discharge arm 36 as shown in the sub-routine SRT3 (FIG. 23). In this case, the control unit 21 extends the discharge arm 36 as shown in FIG. 36, and raises the discharge arm 36 as shown in FIG. 37, to thereby mount the slide glass SG1 onto the mount surface 71BX. Further, the control unit 21 contracts the discharge arm 36 as shown in FIG. 38, thereby gripping the slide glass SG1 in the holding space 85D, and proceeds to the next step SP81.

Figure 39:
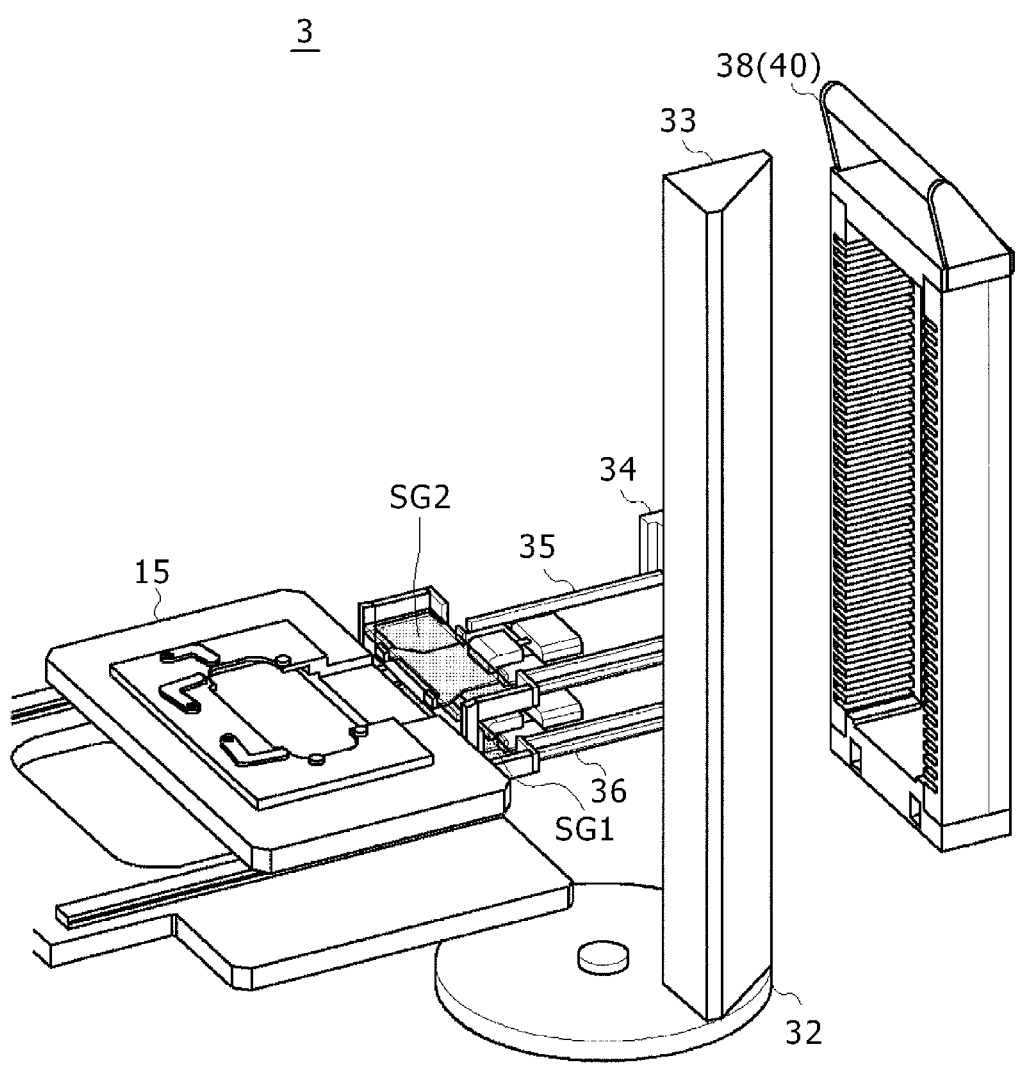

In step SP81, the control unit 21 causes the carriage 34 to move downward, so as to adjust the supply arm 35 to the height of the stage 15 as shown in FIG. 39, and proceeds to the next step SP82.

Figure 40:
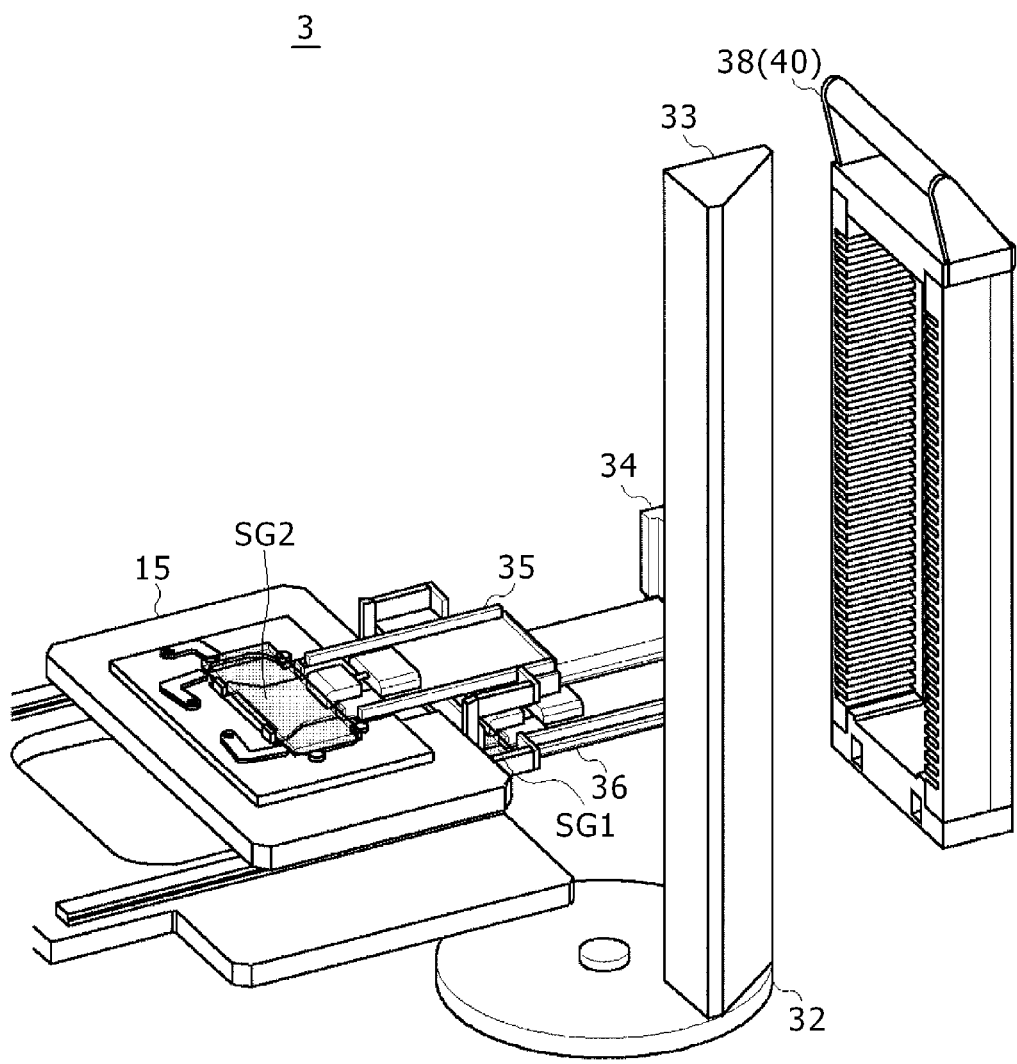
Figure 41:
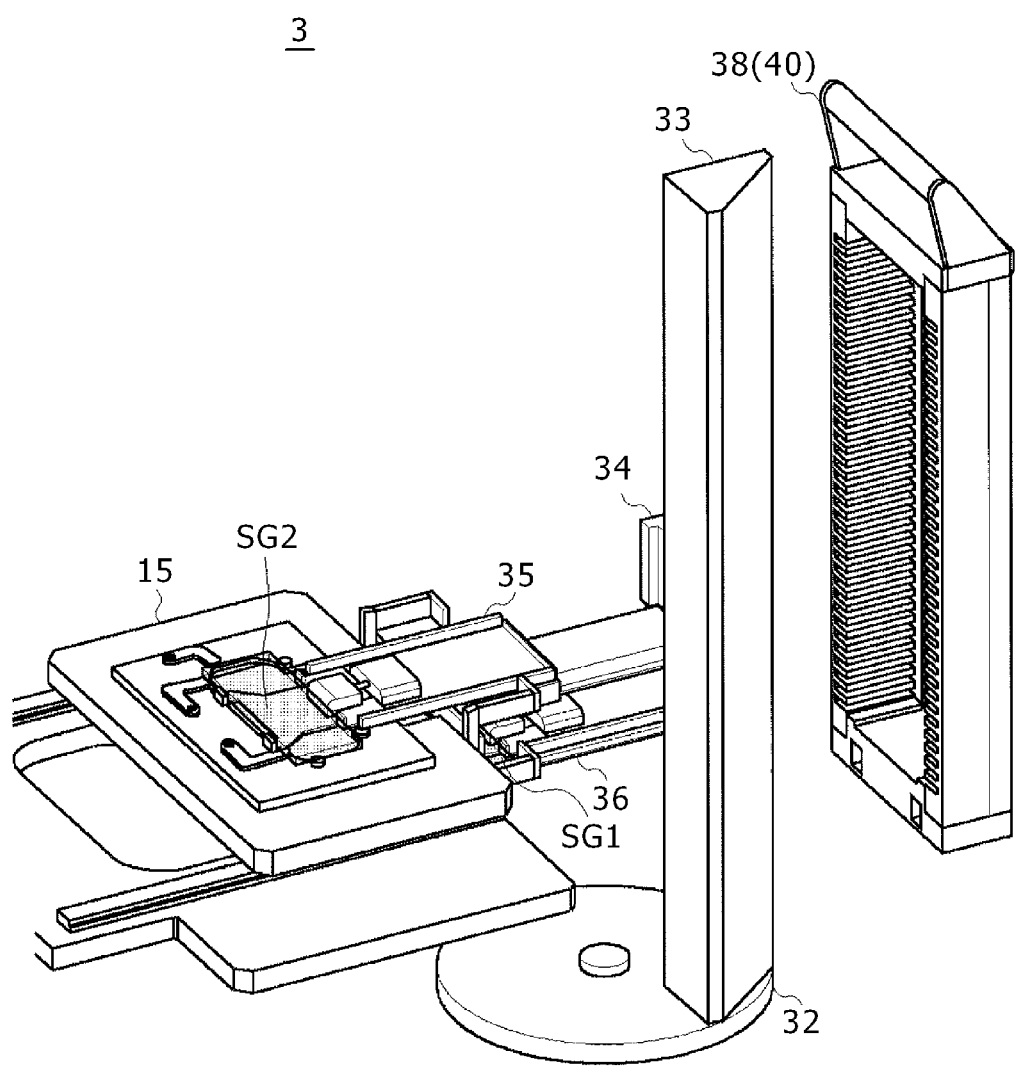
Figure 42:
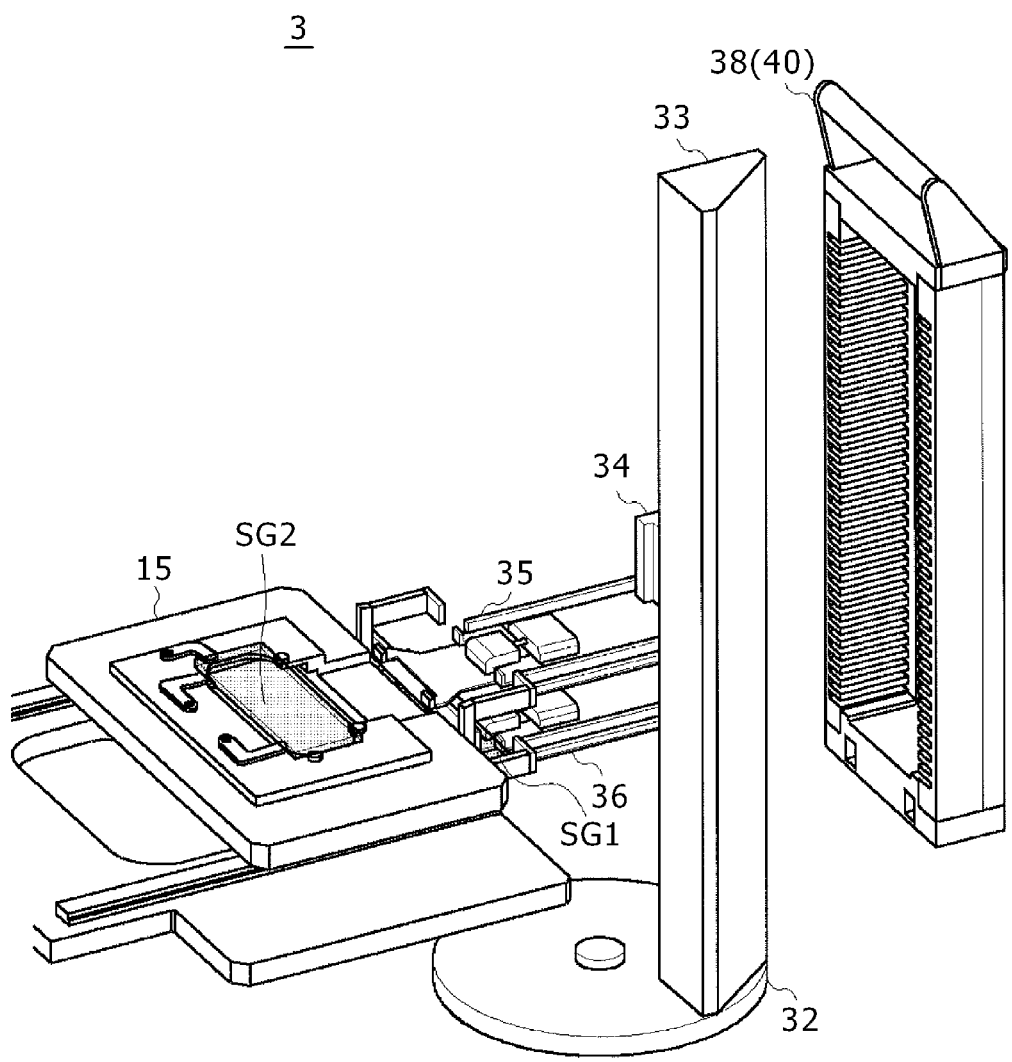

In step SP82, the control unit 21 performs a series of releasing operation process by the supply arm 35 as shown in the sub-routine SRT2 (FIG. 16). In this case, the control unit 21 extends the supply arm 35 as shown in FIG. 40, lowers the supply arm 35 as shown in FIG. 41 so as to mount the slide glass SG2 onto the stage 15, then contracts the supply arm 35 as shown in FIG. 42, and proceeds to the next step SP83.

In step SP83, the control unit 21 causes the carriage 34 to move in the vertical direction, so as to adjust the carriage 34 to the slewing height together with the supply arm 35 and the discharge arm 36, and proceeds to the next step SP84.

Figure 43:
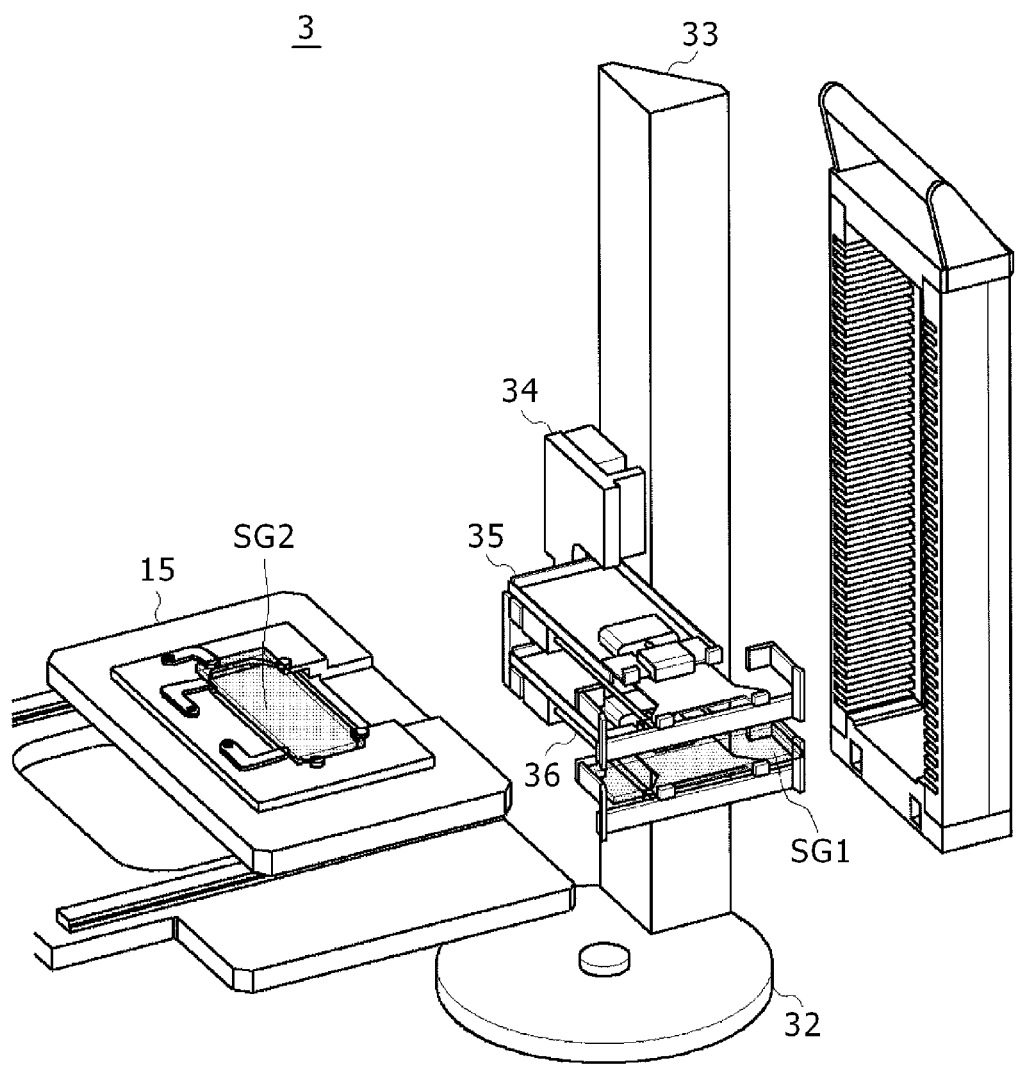
Figure 44:
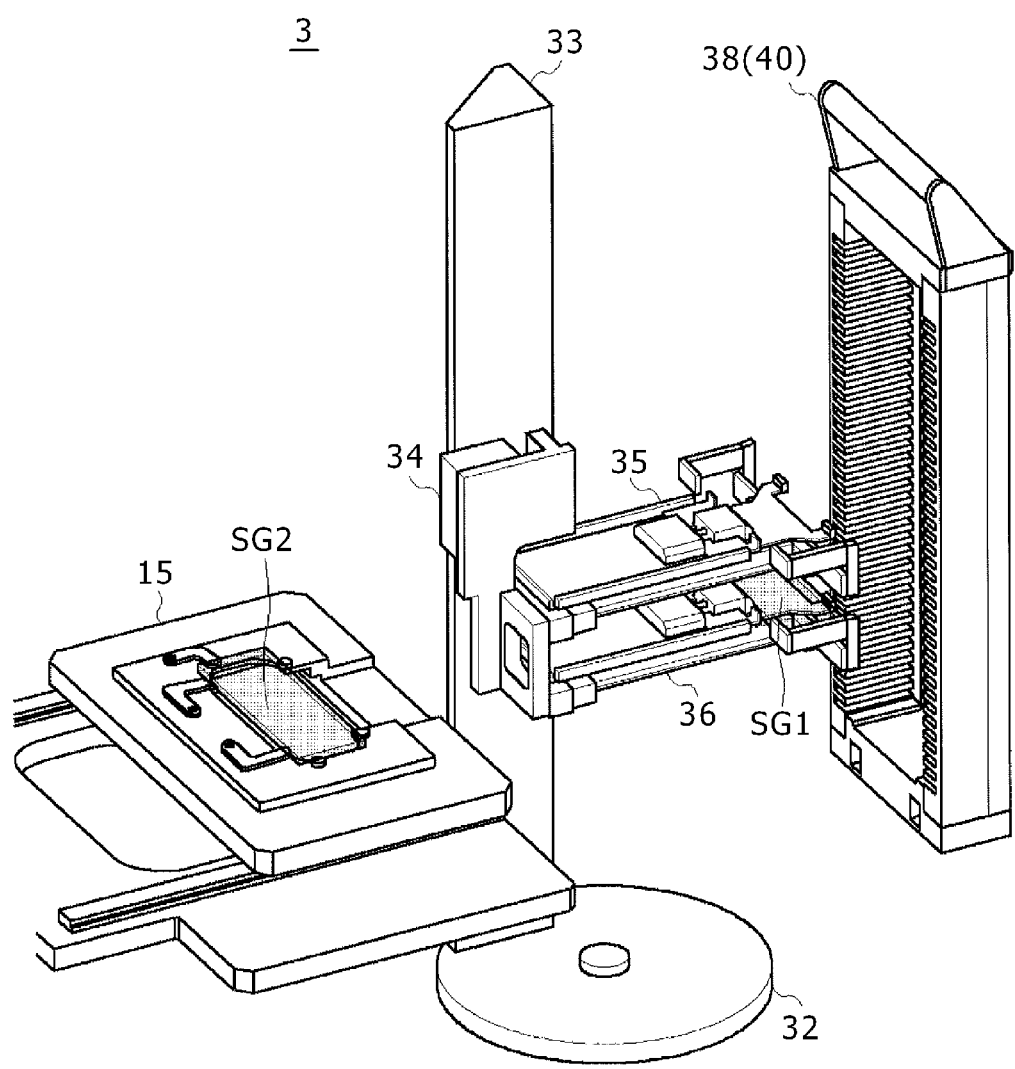

In step SP84, the control unit 21 controls the rotating base 32 so as to slew the carriage 34, the supply arm 35 and the discharge arm 36 as one body into the storage direction as shown in FIGS. 43 and 44, and proceeds to the next step SP85.

Figure 45:
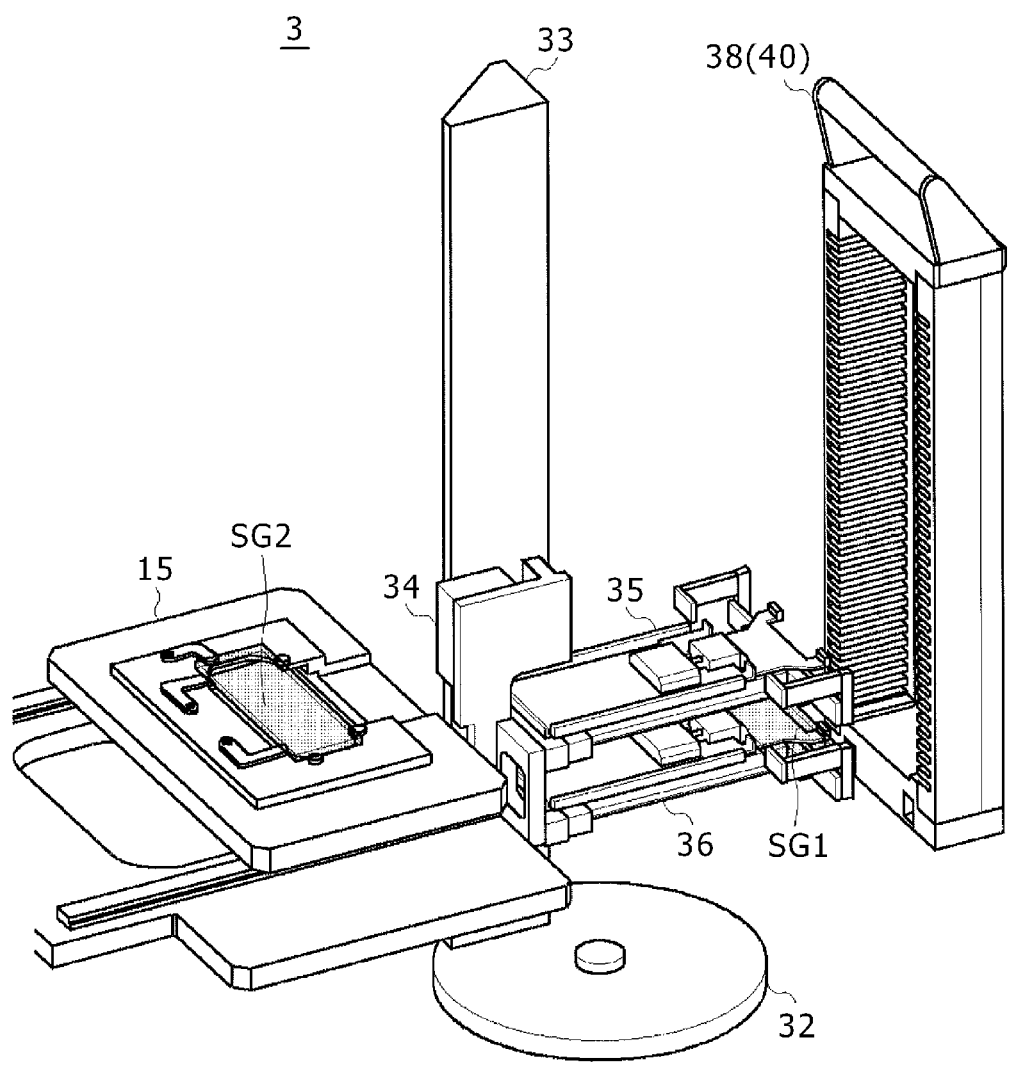

In step SP85, the control unit 21 causes the carriage 34 to move in the vertical direction so as to adjust the height of the discharge arm 36 to the discharge site, or the slot into which to discharge the slide glass SG1, in the multi-sheet cassette 40 as shown in FIG. 45, and then proceeds to the next step SP86.

Figure 46:
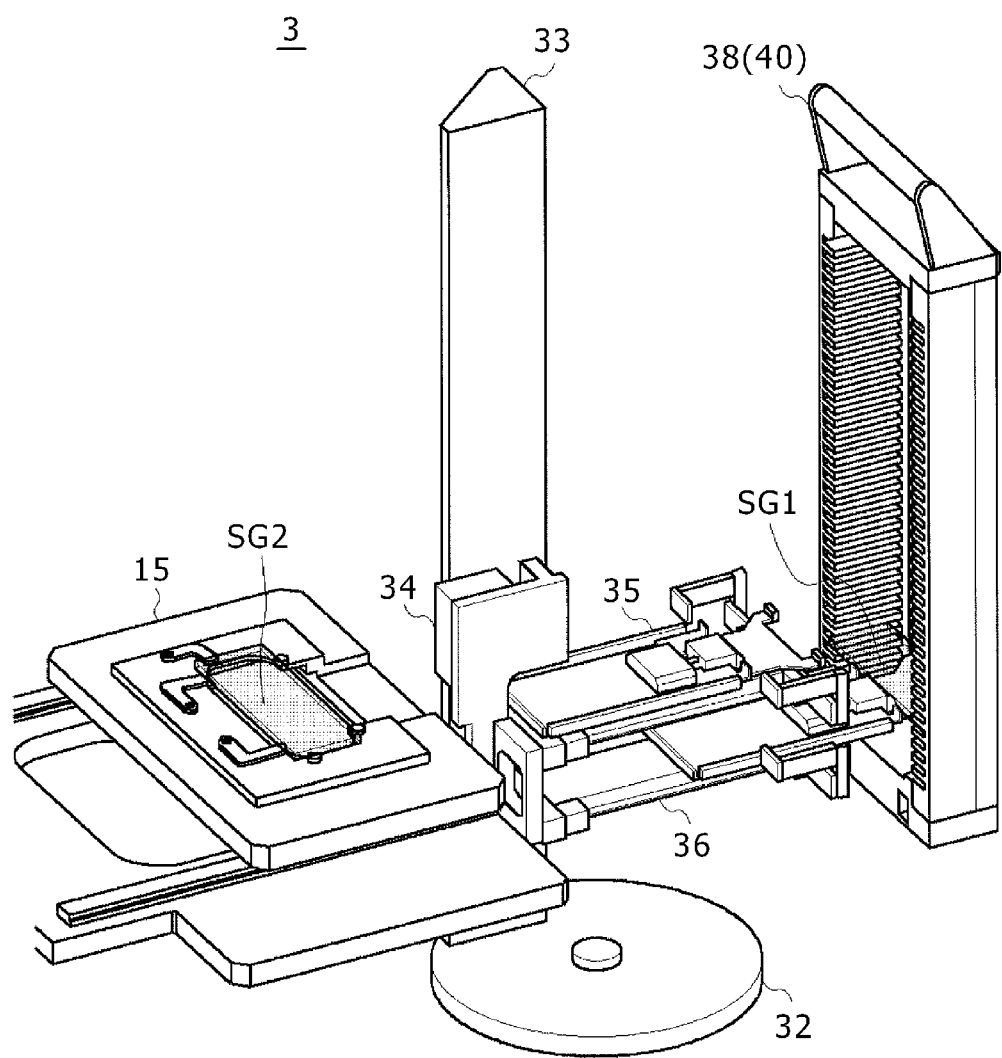

In step SP86, the control unit 21 carries out a series of releasing operation process by the discharge arm 36 as shown in the sub-routine SRT4 (FIG. 24). In this case, the control unit 21 extends the discharge arm 36, then lowers the discharge arm 36 as shown in FIG. 46 so as to support the slide glass SG1 by the multi-sheet cassette 40, further contracts the discharge arm 36, and proceeds to the next step SP87.

In step SP87, the control unit 21 finishes the routine RT3, thereby finishing the procedure of the series of conveying operation process by the supply arm 35 and the discharge arm 36.

1-7. Operation and Effect

In the conveying unit 3 of the microscope system 1 configured as above, the supply arm 35 for supplying the slide glass SG onto the stage 15 and the discharge arm 36 for discharging the slide glass SG from the stage 15 are set independent from each other, and are mounted to the carriage 34 in the manner of overlapping with each other on the upper and lower sides.

During the image sensing (photographing) treatment of a slide glass SG mounted on the stage 15, the control unit 21 of the controlling unit 4 causes the supply arm 35 to pick up and hold a new slide glass SG, and sets it in a stand-by state in the vicinity of the stage 15 together with the empty discharge arm 36.

Then, upon completion of the image sensing (photographing) treatment of the slide glass SG, the control unit 21 of the controlling unit 4 discharges the slide glass SG from the stage 15 by the discharge arm 36, and immediately dispose the new slide glass onto the stage 15 by the supply arm 35.

This ensures that, in the microscope system 1, the replacing process for the slide glass SG mounted on the stage 15 can be completed in an extremely short time.

Particularly, in the microscope system 1, the image sensing (photographing) treatment for producing image pickup data on the slide glass SG is a most time-consuming process, and the image sensing treatment cannot be carried out during the replacing process for the slide glass SG. In relation to this point, it is possible in the microscope system 1 to complete the replacing process for the slide glass SG in an extremely short time, and, therefore, it is possible to considerably shorten the stand-by time for the image sensing treatment and to enhance the working efficiency.

Consequently, in the microscope system 1, in the case of producing image pickup data on a large number (e.g., 300 sheets) of slide glasses SG, the required time can be greatly shortened, and the speed of production of all image pickup data can be enhanced drastically.

Besides, in the microscope system 1, the length in the Q-axis direction of the holding space 65D defined by the guide sections 65B and 65C of the supply arm 35 is adjusted to the longer edge upper limit for the slide glass SG, and the slide glasses SG which cannot be held in the holding space 65D are not picked up.

Further, in the microscope system 1, at the time of gripping the slide glass SG by the gripping unit 70A of the supply arm 35, the grip spacing is detected, and, if the grip spacing falls outside of the shorter edge allowable range, the slide glass SG is not picked up.

Thus, in the microscope system 1, the slide glass SG falling outside of the allowable range can be preliminarily excluded at the time stage of picking up the slide glass SG by the supply arm 35. Consequently, in the microscope system 1, it is possible to obviate a time-consuming operation such as "performing again a replacing treatment of the slide glass SG because the fact that the slide glass SG falls outside of the allowable range is not found until the time stage of mounting the slide glass SG onto the stage 15."

On the other hand, in the microscope system 1, the length in the Q-axis direction and the length in the P-axis direction of the holding space 85D in the discharge arm 36 provided separately from the supply arm 35 are set to be greater than the longer edge upper limit and the shorter edge upper limit for the slide glass SG. Consequently, in the microscope system 1, at the time of picking up from the stage 15 a slide glass SG which has undergone the image sensing (photographing) treatment or for which the fixing treatment has failed, the slide glass SG can be picked up assuredly even if the slide glass SG is positionally deviated or inclined from a properly mounted state.

For example, in the microscope system 1, an application mode is assumed in which a large number (e.g., 300 sheets) of slide glasses SG are preliminarily set in the storage unit 38, and image pickup data are sequentially produced in an unmanned manner by a continuous image sensing treatment in the night.

In such a case, if a slide glass SG is present which cannot be removed from the stage 15 by a series of conveying operation, the image sensing treatment of the subsequent other slide glasses SG cannot be continued, and the whole process is interrupted, so that the remaining image pickup data cannot be produced.

On the other hand, in the microscope system 1, slide glasses SG in various states can be picked up and discharged by the discharge arm 36, while preliminarily excluding the slide glasses SG falling outside of prescription by the supply arm 35. This makes it possible in the microscope system 1 to enhance reliability of the series of conveying operations, and to suppress to an extremely low level the possibility of interruption of the continuous image sensing process.

Besides, in the microscope system 1, the plurality of pedestals 37A to 37E are arranged along the circumference of a circle on the upper surface 31A of the base section 31, and the slide glasses SG are conveyed between the multi-sheet cassettes 40 or one-sheet trays 50 on the pedestals 37A to 37E and the stage 15 by the rotating operation of the rotating base 32.

Meanwhile, in a configuration in which a heavy structure is rectilinearly moved over a long distance as disclosed in Patent Document 1, it may be necessary to enhance the rigidity of each component or part or to suppress an acceleration to a low level, in order that the component or part can endure the moments generated due to acceleration and/or deceleration.

On the other hand, in the microscope system 1, heavy bodies can be concentrated on the center of rotation of a rotating motion, so that stable operations can be performed even in the case of high-speed conveying operations. This makes it possible in the microscope system 1 to easily enhance accuracy while adopting a simple configuration.

Figure 47A:
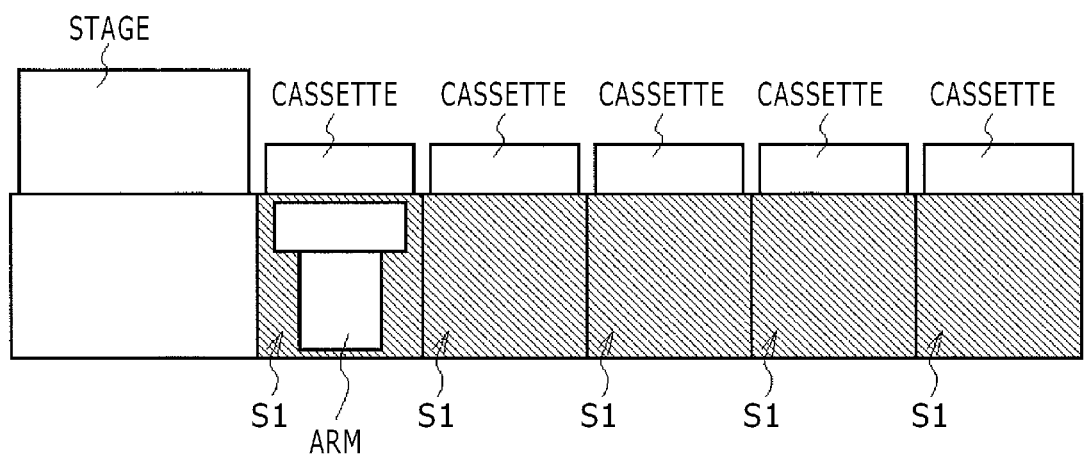
FIGS. 47A and 47B are diagrams for illustrating comparison of occupied areas.

In addition, in such a configuration as disclosed in Patent Document 1, as schematically shown in FIG. 47A, the occupied area necessary for arm movement on the basis of one multi-sheet cassette 40 is a roughly rectangular area S1.

Figure 47B:
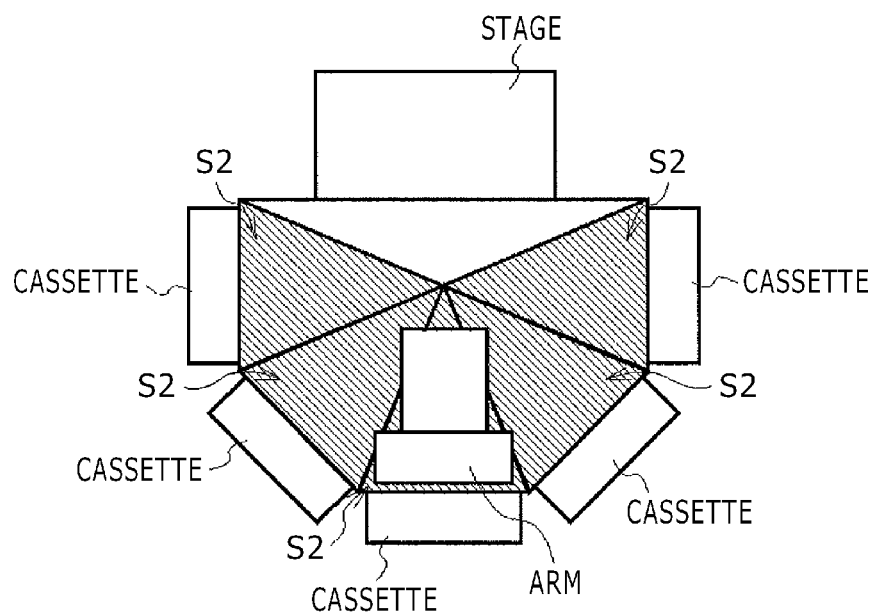

On the other hand, in the configuration in which a rotating motion is used as in the microscope system 1, as schematically shown in FIG. 47B, the occupied area necessary for arm movement on the basis of one multi-sheet cassette 40 is a roughly sector-shaped area S2. Thus, in the microscope system 1, the device configuration can be reduced in size.

In addition, in the one-sheet tray 50 (FIG. 6) of the microscope system 1, the supply tray 52 on which to mount a slide glass SG to be supplied onto the stage 15 and the discharge tray 53 on which to mount a slide glass SG having undergone an image sensing (photographing) treatment are provided separately from each other.

This ensures that, in the microscope system 1, a new slide glass SG to be photographed next can be disposed on the supply tray 52, without causing the operator to worry about the discharge place for a given slide glass SG, during the photographing treatment of the given slide glass SG.

In other words, in the microscope system 1, there is no possibility of generation of a waiting time such as that in "waiting for the discharge of a slide glass SG having undergone an image sensing (photographing) treatment, taking the slide glass SG, and mounting a new slide glass SG."

Further, in the supply tray 52 of the one-sheet tray 50, the lengths of the longer edge and the shorter edge of the holding space 52E (FIGS. 7 and 8) are set to be comparable to the longer edge upper limit and the shorter edge upper limit for the slide glass SG.

This ensures that, in the case where the operator cannot mount a slide glass SG in the holding space 52E, the supply tray 52 permits the operator to recognize that the length of the longer edge or the shorter edge of the slide glass SG falls outside of the allowable range and it may be impossible to properly mount the slide glass SG onto the stage 15.

On the other hand, in the discharge tray 53 of the one-sheet tray 50, the lengths of the longer edge and the shorter edge of the holding space 53D (FIGS. 9 and 10) are set to be sufficiently greater than the longer edge upper limit and the shorter edge upper limit for the slide glass SG.

This ensures in the discharge tray 53 that, even if the slide glass SG is gripped by the discharge arm 36 in the state of being positionally deviated or inclined, the risk of erroneous falling or breaking of the slide glass SG at the time of mounting the slide glass SG in the holding space 53D by the discharge arm 36 can be greatly lowered.

According to the above configuration, in the microscope system 1, the supply arm 35 for supplying a slide glass SG onto the stage 15 and the discharge arm 36 for discharging the slide glass SG from the stage 15 are provided independently from each other. Besides, in the microscope system 1, during the photographing (image pickup) treatment of a slide glass SG, a new slide glass SG is picked up and held by the supply arm 35, and the supply arm 35 is kept in a stand-by state in the vicinity of the stage 15 together with the empty discharge arm 36. In the microscope system 1, further, when the photographing (image pickup) treatment of the slide glass SG is completed, the slide glass SG is discharged from the stage 15 by the discharge arm 36, and the new slide glass SG is immediately disposed on the stage 15 by the supply arm 35. Consequently, in the microscope system 1, replacement of the slide glass SG can be completed in an extremely short time.

2. Other Embodiments

Incidentally, in the embodiment above, description has been made of the case where the supply arm 35 is provided with the fall-off preventive guide 65.

The present application is not limited to the above-described configuration; for example, in the case where the gripping force of the gripping unit 70A is sufficient or in other similar cases, the fall-off preventive guide 65 may be omitted.

In addition, in the embodiment above, description has been made of the case where the lengths of the longer edge and the shorter edge of the holding space 65D in the supply arm 35 are set to the longer edge upper limit and the shorter edge upper limit, respectively.

The present application is not restricted to this configuration; for example, in the case where the length in the longer edge direction of each slot in the multi-sheet cassette 40 is set to the longer edge upper limit or in other similar cases, the lengths of the longer edge and the shorter edge of the holding space 65D may be set to be greater than the longer edge upper limit and the shorter edge upper limit, respectively. Besides, in such a case, the size of the holding space 65D in the supply arm 35 may be set comparable to the size of the holding space 85D in the discharge arm 36.

Further, in the embodiment above, description has been made of the case wherein the length of the shorter edge of the slide glass SG gripped in the gripping operation of the supply arm 35 is obtained as a grip spacing (grip interval) and it is determined whether or not the grip spacing falls within the shorter edge allowable range.

The present application is not limited to this configuration, and a configuration may be adopted in which the grip spacing is not obtained in the gripping operation and it is not determined whether or not the grip spacing falls within the shorter edge allowable range.

Furthermore, in the embodiment above, description has been made of the case where the discharge arm 36 is provided with the fall-off preventive guide 85.

The present application is not restricted to this configuration; for example, in the case where the gripping force of the gripping unit 90A is sufficient or in other similar cases, the fall-off preventive guide 85 may be omitted.

Further, in the embodiment above, description has been made of the case wherein the slide glass SG is moved along the shorter edge direction during the extending operation and the contracting operation of the supply arm 35 and the discharge arm 36.

The present application is not limited to this configuration; for example, the slide glass SG may be moved along the longer edge direction during the extending operation and the contracting operation of the supply arm 35 and the discharge arm 36. In this case, the stage 15 and the multi-sheet cassette 40 and the one-sheet tray 50 in the storage unit 38 may also be shaped so that the slide glass SG is moved along the longer edge direction.

Furthermore, in the embodiment above, description has been made of the case wherein the supply arm 35 and the discharge arm 36 are fixed to the carriage 34 in the state of being oriented in the same direction and overlapping with each other on the upper and lower sides.

The present application is not restricted to this configuration. For example, the supply arm 35 and the discharge arm 36 may be fixed in the state of being oriented in different directions or being juxtaposed on the left and right sides, or may further be so set that their directions can be changed freely.

Further, in the embodiment above, description has been made of the case wherein the pedestals 37 are arranged along the circumference of a circle, and the supply arm 35 and the discharge arm 36 are oriented into the direction of the stage 15 or the multi-sheet cassette 40 or the one-sheet tray 50 by the rotating operation of the rotating base 32.

The present application is not limited to this configuration; for example, like in Patent Document 1, a configuration may be adopted wherein the pedestals 37 are arranged on a straight line along the X-axis direction and the prop 33 is moved rectilinearly in the X-axis direction.

Furthermore, in the embodiment above, description has been made of the case where the discharge tray 53 is provided with the hole 53G and a part of the slide glass SG is exposed from the hole 53G by the processes in steps SP66 to SP68 of the sub-routine SRT3 (FIG. 24).

The present application is not restricted to this configuration; for example, the spacing between the supply tray 52 and the discharge tray 53 may be broadened, the hole 53G may be omitted, and the processes in steps SP66 to SP68 may not be carried out. In such a case, it suffices for the operator to take out the slide glass SG directly from the holding space 53D.

Further, in the embodiment above, description has been made of the case wherein improper holding of the slide glass SG in the holding space 52E of the supply tray 52 is recognized by the operator through tactile sensation, visual sensation or auditory sensation.

The present application is not limited to this configuration; for example, a configuration may be adopted in which cross marks (+) are formed in the four corners in top plan view of the slide glass SG and an image of the supply tray 52 is picked up from above by a predetermined camera to thereby detect the held state of the slide glass SG. In this case, the tetragon obtained by interconnecting the center points of the cross marks on the image picked up by the camera is substantially a rectangle when the slide glass SG is held properly and the tetragon is a trapezoid or a parallelogram when the slide glass SG is not held properly. Therefore, it suffices to determine the held state of the slide glass SG by detecting the center points of the cross marks, through image processing or the like, and computing the lengths of the edges of the tetragon and/or the positional relationships between the center points.

Furthermore, in the embodiment above, description has been made of the case where the one-sheet tray 50 is provided with a single supply tray 52 and a single discharge tray 53.

The present application is not restricted to this configuration; for example, the one-sheet tray 50 may be provided with two or more supply trays 52, or two or more discharge trays 53, or with both two or more supply trays 52 and two or more discharge trays 53.

Further, in the embodiment above, description has been made of the case where the number of the pedestal 37 provided on the base section 31 is five.

The present application is not limited to this configuration, and the number of the pedestals 37 provided on the base section 31 is an arbitrary number such as three or six. In such a case, the distance from the center of rotation of the rotating base 32 to each of the pedestals varies according to the number of the pedestals 37, and, therefore, it is recommendable to determine the number of the pedestals while taking into account the balance thereof with, for example, the lengths of component sections of the supply arm 35 and the discharge arm 36.

Furthermore, in the embodiment above, description has been made of the case where the number of sheets of the slide glass SG which can be stored in the multi-sheet cassette 40 is sixty.

The present application is not restricted to this configuration, and the number of sheets of the slide glasses SG which can be stored in the multi-sheet cassette 40 may be an arbitrary number such as fifty or eighty. In this case, the height (the length in the Z-axis direction) of the multi-sheet cassette 40 varies according to the number of sheets of the slide glasses SG, and, therefore, it suffices to determine the height of the prop 33 according to this factor.

Further, in the embodiment above, description has been made of the case where the microscope unit 2 is combined with the conveying unit 3 and the controlling unit 4.

The present application is not limited to this configuration; for example, the conveying unit 3 and the controlling unit 4 may be put into combination with any of various treating devices for subjecting the slide glasses SG to a predetermined treatment one sheet at a time, such as a label adhering device for printing a label and adhering it to each slide glass SG.

Further, in the embodiment above, description has been made of the case wherein the microscope system 1 as a conveying device or a microscope system includes the storage unit 38 as a storage unit, the stage 15 as a stage, the supply arm 35 as a supply arm, the discharge arm 36 as a discharge arm, the rotating base 32 and the carriage 34 as a moving unit, and the controlling unit 4 as a control unit.

The present application, however, it not limited to this configuration, and the conveying device or the microscope system may include a storage unit, a stage, a supply arm, a discharge arm, a moving unit, and a control unit which are configured in other various manners.

The present application is also applicable to other various microscopes designed to magnify an image of a slide glass.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A conveying device comprising:
a storage unit storing two or more sheets of slide glasses to be subjected to a predetermined treatment;
a stage holding only one sheet of slide glass to be subjected to the treatment;
a supply arm by which one sheet of slide glass to be subjected to the treatment is picked up from the storage unit and supplied onto the stage, the supply arm including a supply fall-off preventive guide which prevents the slide glass from falling off and prevents picking-up of a slide glass which has a length in excess of an upper limit for length in a predetermined direction for a slide glass disposable on the stage;
a discharge arm by which the slide glass mounted on the stage is picked up and discharged in the storage unit;
a moving unit operable to move the supply arm and the discharge arm in an integral manner so as to bring the supply arm or the discharge arm into proximity to each of the storage unit and the stage, the moving unit including a carriage moved as one body with the supply arm and the discharge arm relative to a predetermined base; and
a control unit operable to control the supply arm, the discharge arm and the moving unit,
wherein the control unit performs such a control that a second one of the slide glasses to be subjected to the treatment subsequently to a first one of the slide glasses mounted on the stage is picked up by the supply arm, thereafter the first slide glass is picked up from the stage by the discharge arm brought into proximity to the stage by the moving unit, and then the second slide glass is mounted onto the stage by the supply arm,
wherein the supply arm includes a supply fixed arm section which has a supply holding space for holding the slide glass and which is fixed to the carriage, and a supply moving arm section which has a supply gripping unit for gripping the slide glass and which is moved in a predetermined moving direction relative to the supply fixed arm section, and
wherein the supply fall-off preventive guide includes two supply guide sections by which the length of the supply holding space in a direction substantially orthogonal to the moving direction is restricted to the upper limit.

2. The conveying device according to claim 1, wherein
the supply gripping unit includes a supply fixed gripping element fixed to the supply moving arm section, a supply moving gripping element which is moved in a predetermined gripping movement direction on the basis of a control by the control unit so as to grip the slide glass in the gripping movement direction, and a grip spacing detection section operable to detect a grip spacing between the supply fixed gripping element and the supply moving gripping element in the gripping movement direction; and
the control unit determines whether or not the slide glass is within a predetermined allowable range, based on the grip spacing detected when the slide glass is gripped by the supply gripping unit.

3. The conveying device according to claim 1, wherein the discharge arm includes a discharge fall-off preventive guide which prevents the slide glass from falling off.

4. The conveying device according to claim 3, wherein
the discharge arm includes a discharge fixed arm section which has a discharge holding space for holding the slide glass and which is fixed to the moving body, and a discharge moving arm section which has a discharge gripping unit for gripping the slide glass and which is moved in a predetermined moving direction relative to the discharge fixed arm section; and
the discharge fall-off preventive guide includes two discharge guide sections by which the length of the discharge holding space in a direction substantially orthogonal to the moving direction is restricted to a length longer than the upper limit.

5. The conveying device according to claim 1, wherein the moving unit includes
a base section which is fixed, and
a rotating section which is rotated about a predetermined rotation axis relative to the base section and by which a carriage moved as one body with the supply arm and the discharge arm is moved in a direction substantially parallel to the rotation axis.

6. The conveying device according to claim 5, wherein the storage unit has one or more storage devices in which one or more sheets of slide glasses are stored and which are arranged on the circumference of a circle having a center on the rotation axis relative to the base section.

7. A conveying method comprising:

bringing a supply arm operable to grip one sheet of slide glass from a storage unit storing two or more sheets of slide glasses to be subjected to a predetermined treatment, operable to supply the one sheet of slide glass onto a stage for holding only one sheet of slide glass thereon, and operable to prevent pick-up of a slide glass which has a length in excess of a restricted upper limit by restricting the upper limit with at least one supply guide section, and a discharge arm operable to pick up the slide glass mounted on the stage and discharge the slide glass into the storage unit, into proximity to the storage unit by moving the supply arm and the discharge arm with a carriage moved as one body relative to a predetermined base so as to bring the supply arm and the discharge arm into proximity to the storage unit or the stage;

picking up a second slide glass from the storage unit by the supply arm;

bringing the supply arm and the discharge arm into proximity to the stage using the carriage;

picking up a first slide glass from the stage by the discharge arm;

mounting the second slide glass onto the stage by the supply arm;

bringing the supply arm and the discharge arm into proximity to the storage unit using the carriage; and mounting the second slide glass onto the storage unit by the discharge arm.

8. The conveying method of claim 7, which includes preventing the one sheet of slide glass from falling off of the supply arm.

9. The conveying method of claim 7, wherein moving the supply arm and the discharge arm includes rotating the supply arm and the discharge arm as one body about a predetermined rotation axis.

10. The conveying method of claim 7, which includes restricting the upper limit in a direction substantially orthogonal to a moving direction.

11. The conveying method of claim 7, which includes holding the one sheet of slide glass in a supply holding space which is fixed to the carriage.

12. The conveying method of claim 7, which includes gripping the one sheet of slide glass with a supply gripping unit of the supply arm which is moved in a predetermined moving direction relative to a supply fixed arm section of the supply arm which has a supply holding space for holding the one sheet of slide glass.

\* \* \* \* \*